United States Patent [19]
Adachi et al.

[11] Patent Number: 5,531,664
[45] Date of Patent: Jul. 2, 1996

[54] BENDING ACTUATOR HAVING A COIL SHEATH WITH A FIXED DISTAL END AND A FREE PROXIMAL END

[75] Inventors: Hideyuki Adachi, Hachioji; Sakae Takehana, Machida; Yasuhiro Ueda, Kokubunji; Yasuo Hirata; Kazuhiro Takahashi, both of Hachioji, all of Japan

[73] Assignee: Olympus Optical Co., Ltd., Tokyo, Japan

[21] Appl. No.: 280,564

[22] Filed: Jul. 25, 1994

Related U.S. Application Data

[63] Continuation of Ser. No. 812,929, Dec. 24, 1991, abandoned.

[30] Foreign Application Priority Data

| Dec. 26, 1990 | [JP] | Japan | 2-406838 |
| May 24, 1991 | [JP] | Japan | 3-120181 |
| Sep. 17, 1991 | [JP] | Japan | 3-236239 |
| Nov. 14, 1991 | [JP] | Japan | 3-299021 |
| Nov. 14, 1991 | [JP] | Japan | 3-299022 |

[51] Int. Cl.$^6$ ............................ A61B 1/00; A61B 1/12
[52] U.S. Cl. .................... 600/149; 600/151; 600/152; 600/158
[58] Field of Search .................... 128/4–11, 772; 606/46, 78; 604/281, 95; 385/118; 337/140; 60/527; 901/19

[56] References Cited

U.S. PATENT DOCUMENTS

| 4,586,335 | 5/1986 | Hosoda et al. | 60/527 X |
| 4,751,821 | 6/1988 | Birchard | 60/527 X |
| 4,794,912 | 1/1989 | Lia . | |
| 4,799,474 | 1/1989 | Ueda | 128/4 |
| 4,846,573 | 7/1989 | Taylor et al. | 385/118 X |
| 4,884,557 | 12/1989 | Takehana et al. | 128/4 |
| 4,987,314 | 1/1991 | Gotanda et al. | 337/140 |
| 5,143,085 | 9/1992 | Wilson | 128/772 |
| 5,150,864 | 9/1992 | Roglin et al. | 244/219 |

FOREIGN PATENT DOCUMENTS 61-197770  9/1986  Japan .

*Primary Examiner*—Richard J. Apley
*Assistant Examiner*—John P. Leubecker
*Attorney, Agent, or Firm*—Armstrong, Westerman, Hattori, McLeland & Naughton

[57] ABSTRACT

A bending drive member to bend a bending member is arranged to extend in the direction of length of an elongate tube having flexibility, and attached to near the distal end of the tube with the distal end of the bending drive member being restricted in its position. The bending member drive member comprises a shape memory member formed by bundling together a plurality of wire-like shape memory materials each having a length, that spans from the position of one end to the other end, reversibly changed upon heating/cooling. The length of the shape memory member is changed dependent on a drive signal from a unit with a capability of heating. A non-compressive coil sheath through which the bending drive member extends is fixed at a distal end thereof to the elongate tube while the proximal end of the coil sheath is a free end with respect to the elongate tube.

15 Claims, 43 Drawing Sheets

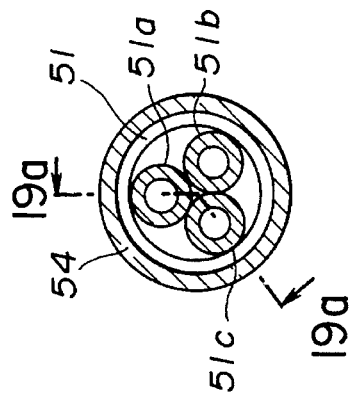
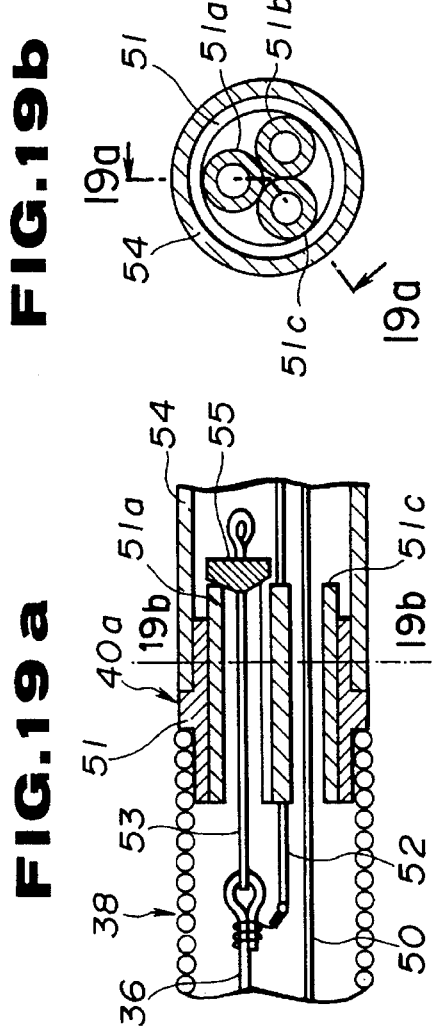
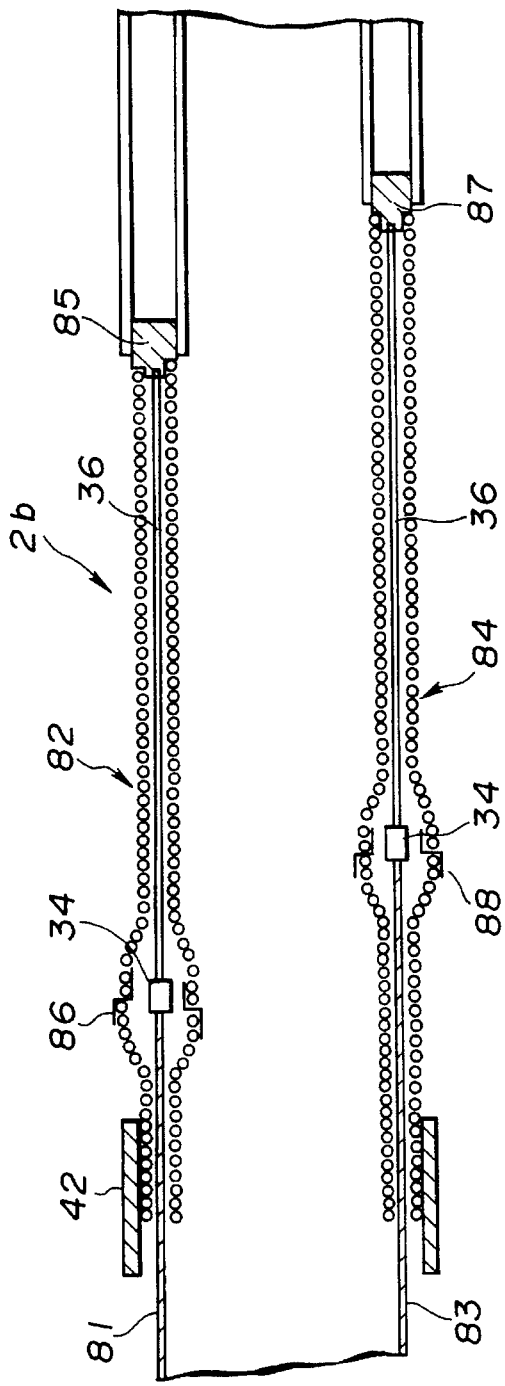

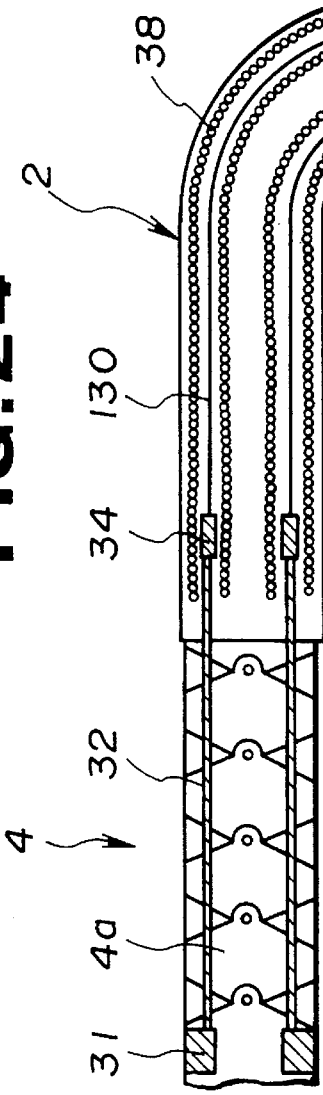

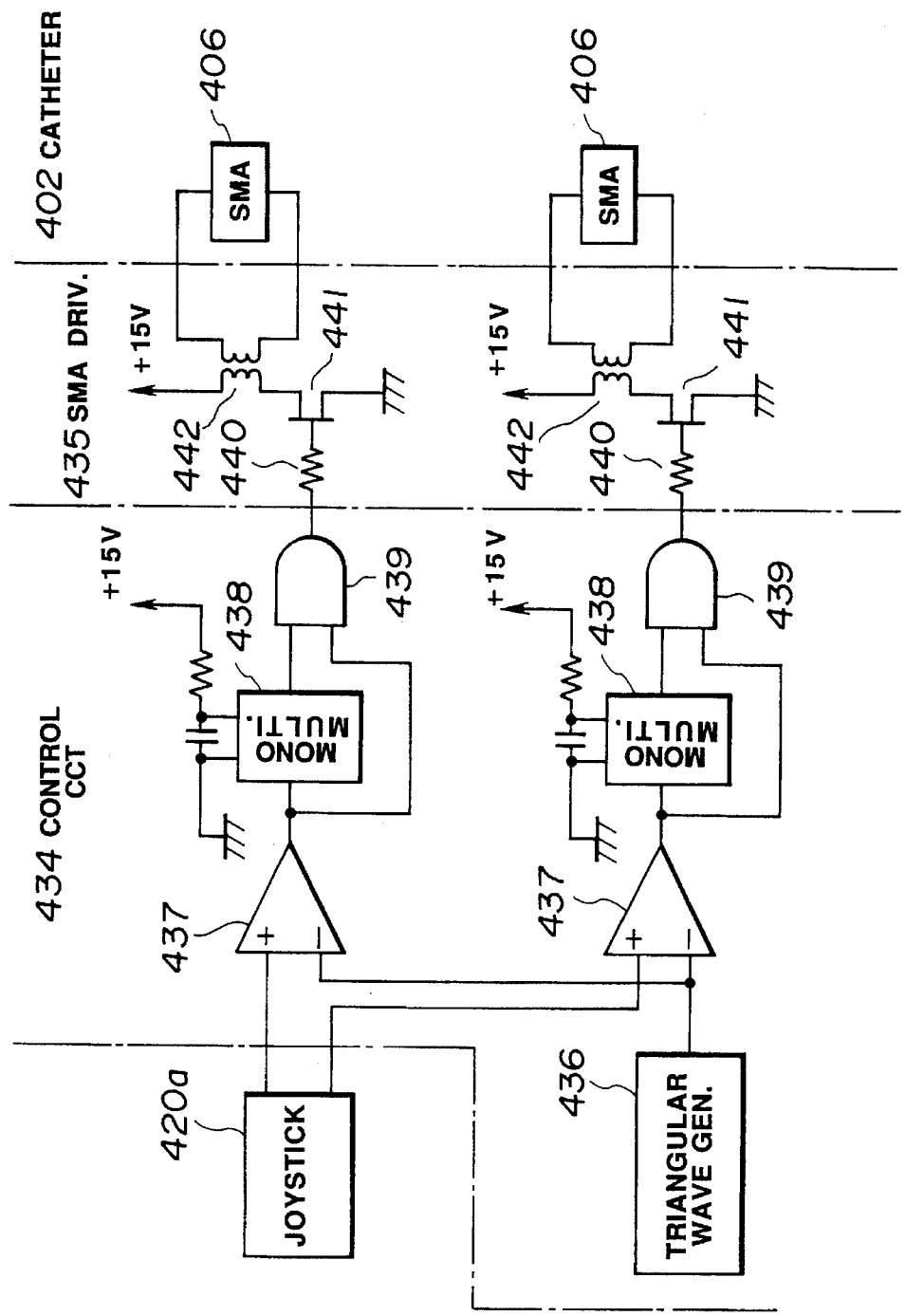

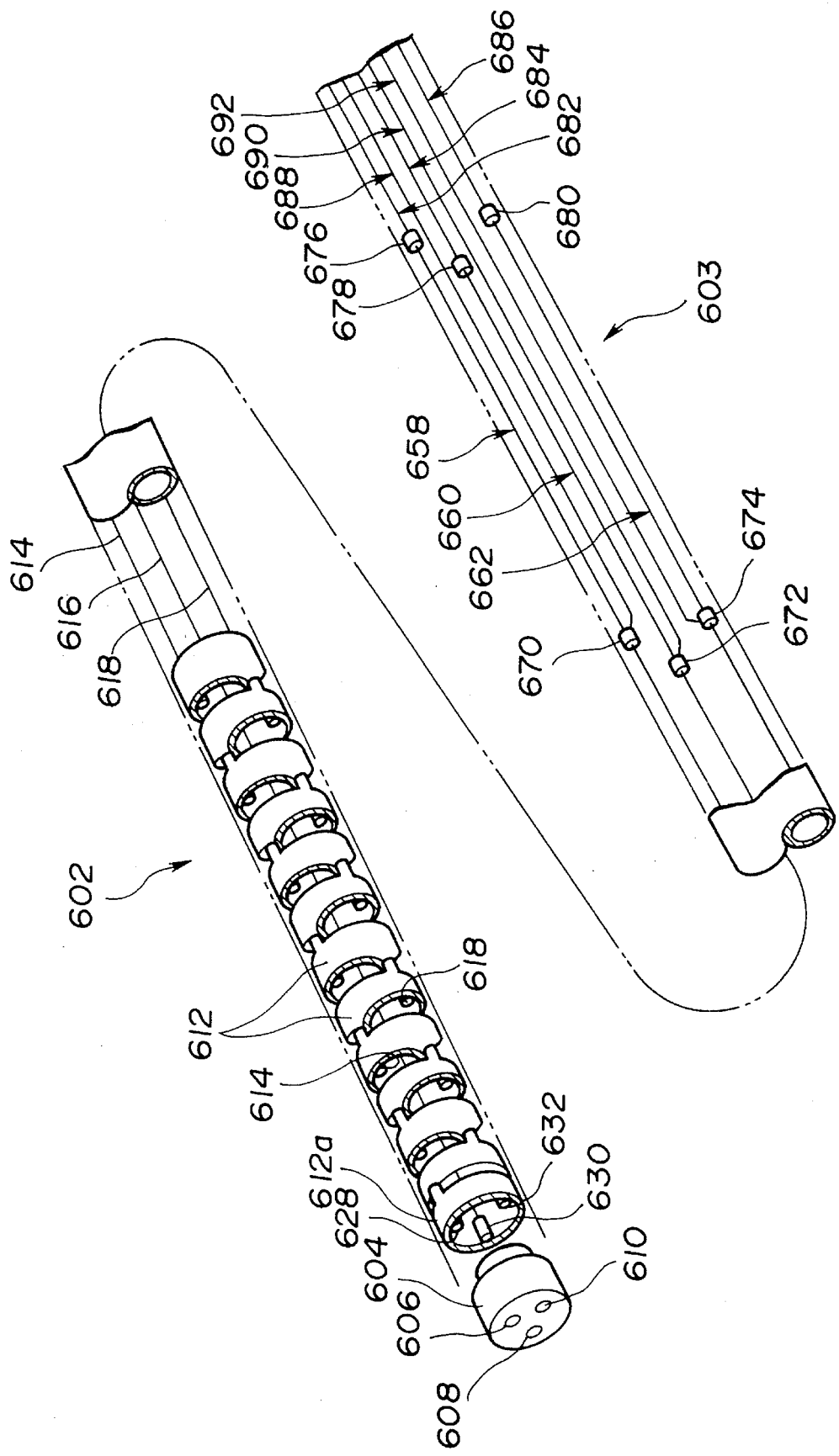

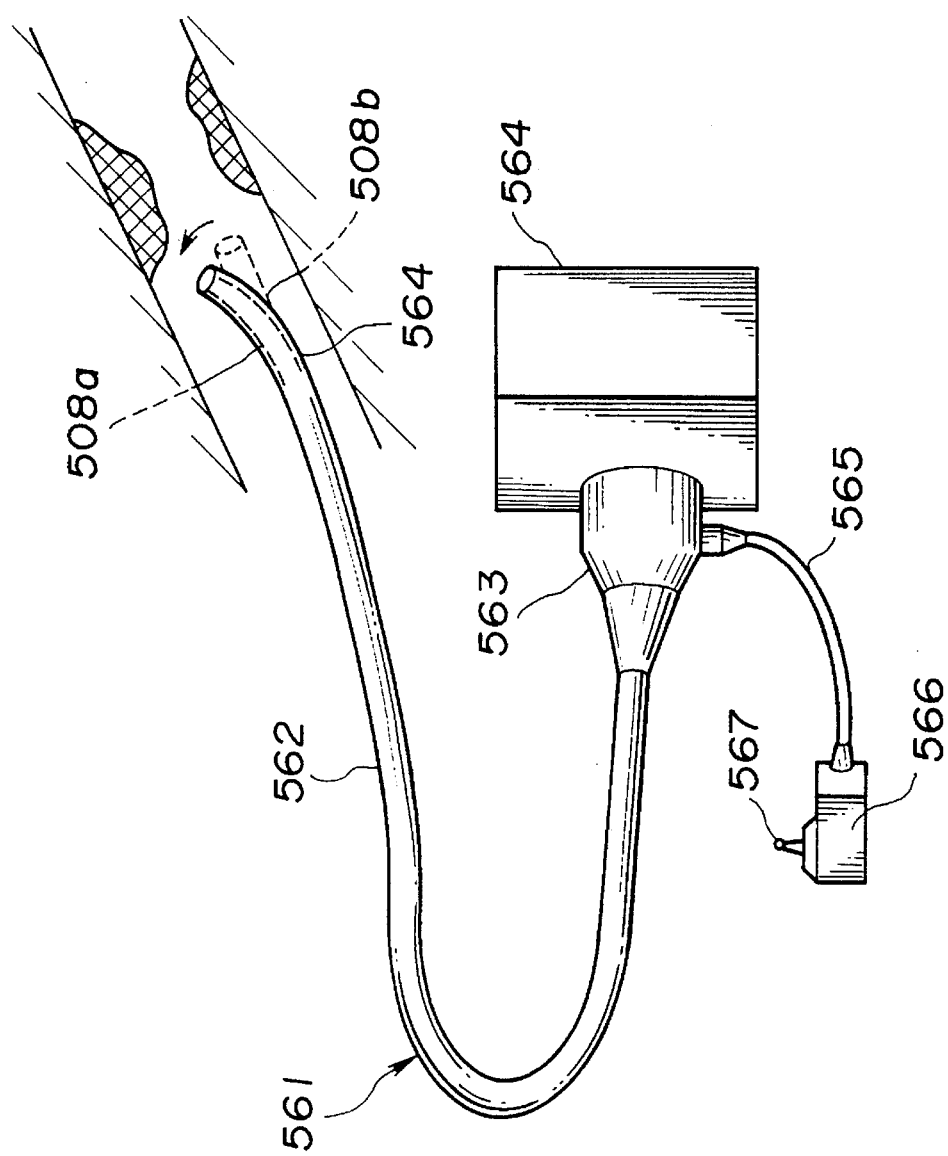

BENDING ACTUATOR HAVING A COIL SHEATH WITH A FIXED DISTAL END AND A FREE PROXIMAL END

This application is a continuation of application Ser. No. 07/812,929 filed Dec. 24, 1991, now abandoned.

BACKGROUND OF THE INVENTION

1. Field of the Invention

The present invention relates to a probe device with a bending actuator in which a distal end portion is formed of an axially expanding and contracting shape memory alloy.

2. Description of the Related Art

Generally, endoscopes and other like devices having probes such as insert tubes (or insert portions), which can be inserted to the subject's interior for the purpose of inspecting the interior of subjects such as chemical plants and living bodies, are widely used for non-destructively inspecting the subject's interior.

Ducts, tracts or cavities leading to the subject's interior are sharply curved in general in many cases. Accordingly, when a location to be inspected is at a deep position, it is difficult to introduce the distal end side of a probe up to such a location. This results in that the inspection takes plenty of time and, if the subject is a living body, the living body is subjected to substantial discomfort.

In the related art, there have been disclosed several examples of a device having a bending actuator, i.e., a bending drive mechanism, in which the distal end side of a probe is formed into a bendable portion capable of being driven to bend as desired when the probe is operated from the side near an operator (i.e., the proximal end side), thereby facilitating introduction of the probe into the subject's interior.

For example, U.S. Pat. No. 4,794,912 discloses a borescope or endoscope provided with a fluid dynamic muscle. This prior art is designed to produce a drive force in the axial direction by a bag of which volume can be diminished using a fluid. However, producing the axial drive force requires a reduction in the dimensions of the bag not only in the axial direction but also in a direction perpendicular to the axial direction. Accordingly, when this prior art is used with probes in those applications where the probes are desired to be small and thin in diameter in order so that the probes can be inserted to even thin ducts or tracts, or the friction generated upon insertion of the probes can be reduced (particularly, to make a living body feel less pain), there occurs a disadvantage of rendering outer diameters of the probes too large.

Further, U.S. Pat. No. 4,794,912 discloses an endoscope having a bendable portion formed of a shape memory alloy which is driven to bend as desired. With this prior art, because the shape memory alloy is used in the form of a single cable, it is required to increase a diameter of the cable for providing a drive force necessary. In this case, a reduction in flexibility of the probe portion including the shape memory alloy built therein adds the friction resistance produced upon the probe portion being inserted to sharply curved ducts or tracts, and thus makes the inserting operation difficult.

Meanwhile, Japanese Patent Laid-Open No. 61-197,770 discloses a shape deformable member in which at least two shape memory alloys having different temperatures of transformation are combined with each other in such twisted fashion as being capable of deforming into three or more shapes. In this prior art, a linear shape deformable member shown in FIG. 2(a) of the drawings in the cited Japanese Patent Laid-Open can be deformed by heating into a coiled shape with a large spiral pitch as shown in FIG. 2(c) and a coiled shape with a small spiral pitch as shown in FIG. 2(c). Also, another shape deformable member formed by bonding two plate-like shape memory alloys having different temperatures of transformation together (see FIG. 6(a) in the cited Japanese Patent Laid-Open) can be deformed by heating to bend from a linear shape through different amounts in a direction vertical to the plate surface (see FIGS. 6(b) and 6(c)).

The last mentioned prior art teaches that use of shape memory alloys having different temperatures of transformation enables the shape deformable member to deform into three or more shapes which cannot be realized in the case of using shape memory alloys having the same temperature of transformation. Therefore, when that prior art is employed for deformation into a number of shapes, it is necessary to use a number of shape memory alloys having different temperatures of transformation. This means that in the application field of inserting tubes which need to be set to any desired bending amounts, use of a large number of shape memory alloys is necessary in order to change the axial length of the shape deformable member in a substantially continuous manner.

Since drive forces required for the bendable portions of probes to bend as desired are generally different dependent on probe diameters, kinds of members built in insert tubes, and so forth, the cross-sectional area of the shape deformable member must be varied to set an appropriate drive force for each of the probes. Application of the last mentioned prior art to such a case results in the disadvantage of requiring the preparation of quite a large number of shape memory alloys with several different diameters for each alloy, as components used for construction of the shape deformable member, and also an arrangement of those shape memory alloys so that the total cross-sectional area becomes equal to a cross-sectional area determined from the viewpoint of producing a necessary drive force, which remarkably pushes up the cost when the above prior art is used with a bending drive member.

SUMMARY OF THE INVENTION

An object of the present invention is to provide a probe device equipped with a bending actuator which can be set into any desired bent condition at a reduced cost.

Another object of the present invention is to provide an endoscope which can realize an insert (probe) having a bending actuator formed in such a manner as to be able to reduce a diameter and set any desired bent condition.

A probe device equipped with a bending actuator according to the present invention comprises a flexible elongate tube, a bending drive member attached near the distal end of the tube with at least one end thereof being restricted in its position, for bending the distal end side of the tube, a shape memory member formed by bundling together a plurality of wire-like shape memory materials each having a length, that spans from the position of one end to the other end thereof, reversibly changed upon heating/cooling, heating means electrically conducted with the shape memory member to supply a drive signal for at least heating the shape memory member, and control means for controlling the heating means and setting the length of the shape memory member to any of a plurality of different values within a temperature range of transformation where the length of at least one of the wire-like shape memory materials jointly making up the shape memory member is reversibly changed.

A bendable probe according to the present invention comprises a bending drive member having one end fixed to the distal end of a flexible tube and the other end as a free end and being able to change an overall length thereof, and a joint member being fixed at the distal end thereof to the inner surface of the flexible tube and at the proximal end thereof to the free end of the bending drive member, and being pliable in the radial direction but non-compressive in the direction of length thereof.

BRIEF DESCRIPTION OF THE DRAWINGS

FIGS. 1 to 19 are concerned with a first embodiment of the present invention in which;

FIG. 1 is a diagram showing the entire configuration of an endoscope device for industrial purposes, FIG. 2 is a sectional view showing the distal end side of a flexible tube, FIG. 4 is an enlarged view showing the construction of a wire joint member, FIG. 6 is a block diagram showing a bending control mechanism of the endoscope for industrial purposes, FIG. 7 is a side view showing the structure of an SMA (shape memory alloy) wire, FIG. 9 is an explanatory view showing extended and contracted conditions of a strand dependent on temperatures, FIG. 10 is an explanatory view showing how the SMA wire shown in FIG. 7 deforms upon heating, FIG. 11 is a characteristic graph showing the relationship of length versus temperature of the SMA wire strand, FIG. 12 is a block diagram showing primary components of a bending controller, FIG. 13 is a characteristic graph showing the relationship of change in resistance versus temperature of the SMA wire, FIG. 14 is an explanatory view for explaining bending operation of the distal end side of the flexible tube, FIG. 15 is a sectional view showing a modification in which the SMA wire is in the spring form, FIG. 17 is a perspective view showing the structure of a modification of a non-compressive member, FIG. 18 is a sectional view showing the structure of a modification of means for fixing the coil sheath, FIG. 19a is a sectional view taken along the line 19b—19b in FIG. 19b, showing a joint portion at the proximal end of the SMA wire, and FIG. 19b is a sectional view taken along the line 19a—19b in FIG. 19a;

FIG. 20 is a sectional view showing the distal end side of a flexible tube in a second embodiment of the present invention;

FIG. 24 is a sectional view showing an axial section of a flexible tube in a fifth embodiment of the present invention;

FIG. 25 is a sectional view taken along the line 25—25 in FIG. 24;

FIGS. 28 to 30 are concerned with a seventh embodiment of the present invention in which;

FIG. 28 is a diagram showing the entire configuration of an endoscope device for industrial purposes, FIGS. 30a–20b are a set of explanatory views for explaining a storage condition of the exhaust plug provided in the drum during a storage period;

FIGS. 34 to 38 are concerned with a ninth embodiment of the present invention in which;

FIG. 34 is a diagram showing the entire configuration of an endoscope device according to the ninth embodiment, FIG. 35 is a sectional view showing part of the bendable portion in enlarged scale, FIG. 36 is a functional block view of a bending controller, FIG. 37 is a practical circuit diagram of a driver and a resistance value detector circuit, and FIG. 38 is a characteristic graph showing the relationship of heating temperature versus resistance value of a shape memory alloy;

FIGS. 43 to 48 are concerned with a tenth embodiment of the present invention in which;

FIG. 43 is an explanatory view showing the entire configuration of a catheter device according to the tenth embodiment;

FIG. 44 is an explanatory view showing the construction of the distal end side of the catheter, FIG. 45 is a sectional view taken along the plane containing a shape memory alloy in FIG. 44, FIG. 46 is a block diagram showing the configuration of a bending drive unit, FIG. 47 is a circuit diagram showing the detailed configuration of a control circuit and a shape memory alloy driver in FIG. 46, and FIG. 48 is a circuit diagram showing another example of the shape memory alloy driver;

FIGS. 49 to 51 are concerned with an eleventh embodiment of the present invention in which;

FIG. 49 is a sectional diagram showing the construction of the distal end portion of an insert of an endoscope according to the eleventh embodiment, FIG. 50 is a block diagram showing the configuration of a bending drive unit, and FIG. 51 is a circuit diagram showing the detailed configuration of a shape memory alloy driver in FIG. 50;

FIGS. 52 to 57 are concerned with a twelfth embodiment of the present invention in which;

FIG. 52 is a view showing the schematic configuration of a flexible tube in the twelfth embodiment, FIG. 55 is a chart for explaining operation to drive three SMA wires, FIG. 56 is a block diagram showing the configuration of a driver, and FIG. 57 is a block diagram showing another configuration of the driver;

FIGS. 58 to 64 are concerned with a thirteenth embodiment of the present invention in which;

FIG. 58 is a view showing the schematic configuration of a blood vessel endoscope device of the thirteenth embodiment, FIG. 59 is a sectional view of the distal end portion of a catheter, FIG. 60 is a view as viewed in the direction of the line 60—60 in FIG. 59, FIG. 61 is a view as viewed in the direction of the line 61—61 in FIG. 60, FIG. 62 is a view as viewed in the direction of the line 62—62 in FIG. 60, FIG. 63 is a block diagram showing the configuration of a power supply controller, and FIG. 64 is a perspective view showing the distal end portion of the catheter;

FIGS. 65 to 67 are concerned with a fourteenth embodiment of the present invention in which;

FIG. 65 is a front view showing the distal end of a catheter,

FIG. 66 is a sectional view taken along the line 66—66 in FIG. 65, and

FIG. 67 is a sectional view taken along the line 67—67 in FIG. 65;

FIGS. 68 to 70 are concerned with a fifteenth embodiment of the present invention in which;

FIG. 68 is a front view showing the distal end of a catheter,

FIG. 69 is a sectional view taken along the line 69—69 in FIG. 68, and

FIG. 70 is a sectional view taken along the line 70—70 in FIG. 68;

FIG. 74 is a perspective view showing a laser probe according to a nineteenth embodiment of the present invention.

DETAILED DESCRIPTION OF THE PREFERRED EMBODIMENTS

Hereinafter, preferred embodiments of the present invention will be described with reference to the drawings.

Figure 1:
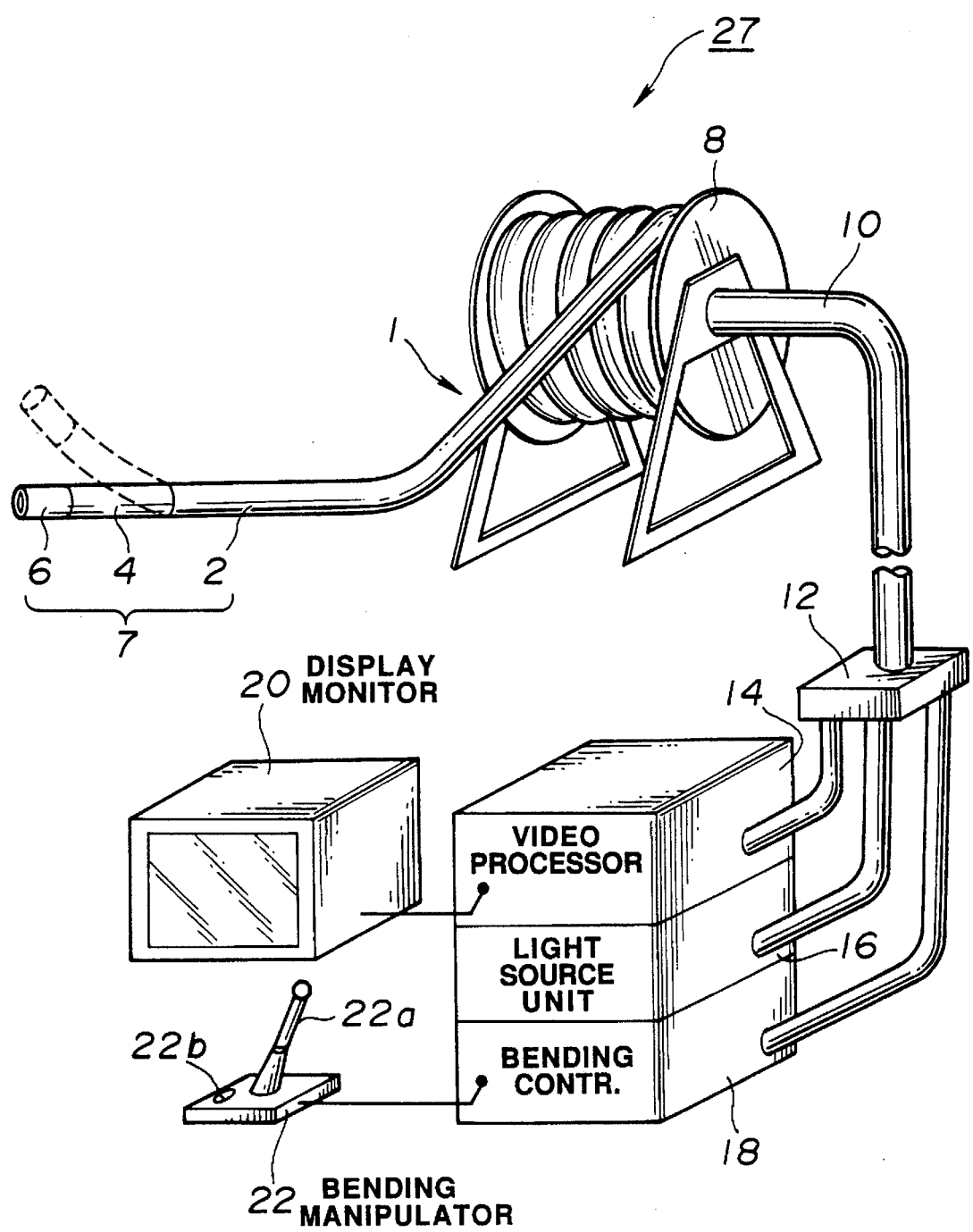

As shown in FIG. 1, an endoscope device 27 for industrial purposes, in the form of a probe device, according to a first embodiment comprises an endoscope 1 used to inspect the interior of plants, a light source unit 16 for supplying a ray of illumination light to the industrial-purposed endoscope 1, a video processor 14 for processing signals from image sensing means built in the distal end side of the industrial-purposed endoscope 1, a monitor 20 for displaying a video signal outputted from the video processor 14, a bending manipulator 22 for manipulating a bendable portion 4, provided in the industrial-purposed endoscope 1, to bend as desired, and a bending controller 18 for making control to drive and bend the bendable portion 4 dependent on manual operation of the bending manipulator 22.

The endoscope 1 has an insert 7 serving as a probe which is directly inserted to the interior of plants and so forth. The insert 7 comprises a long flexible tube portion 2, the bendable portion 4 provided to extend from the distal end of the flexible tube portion 2, and a hard distal end portion 6 provided to extend from the distal end of the bendable portion 4 and including an optical system attached therein. The flexible tube portion 2 is wound around a rotatable drum 8.

A universal cord 10 connected to the flexible tube portion 2 is extended from the center of the drum 8 to the exterior thereof. Via a connector 12, the universal cord 10 is connected to the video processor 14 for carrying out signal processing, the light source unit 16 for supplying a ray of illumination light, and the bending controller 18 for carrying out bending control.

A display monitor 20 is connected to the video processor 14 so that an image sensed by the industrial-purposed endoscope 1 is converted by the video processor 14 into a standard video signal and then displayed by the display monitor 20. The bending manipulator 22 is connected to the bending controller 18 so that the bendable portion 4 is operated to bend as desired. The bending manipulator 22 includes a joystick 22a for instructing an operation to bend the bendable portion 4 and a bending indicator switch 22b.

Figure 2:
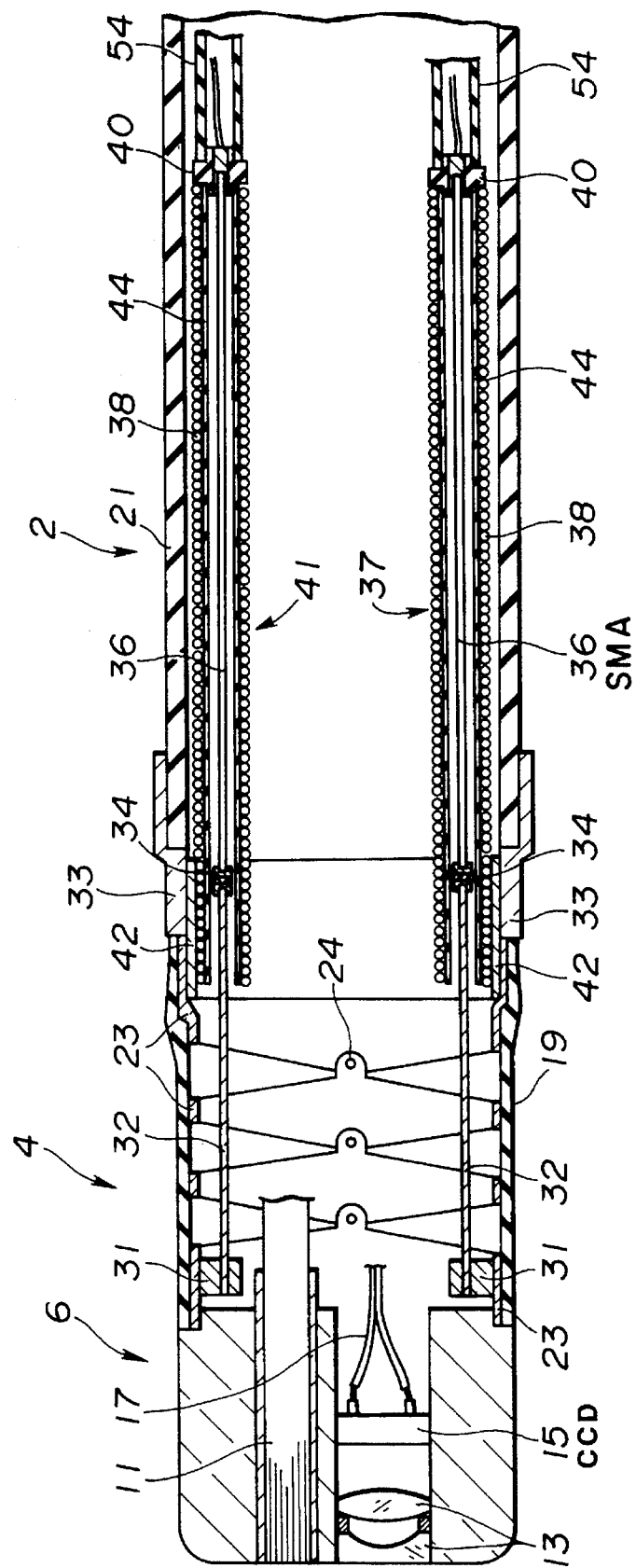

As shown in FIG. 2, the front end of a flexible tube 19 forming an outer peripheral wall of the bendable portion 4 is fixed to the proximal end of a hard member forming the distal end portion 6. Inside the tube 19, a plurality of ring-like bending pieces 23 which jointly constitute the bendable portion 4, are joined to each other in the direction of length of the tube 19. In the illustrated case, every two adjacent ring-like bending pieces 23 are rotatably joined to each other by a pivotally supporting member 24 like a rivet such that the tube 19 is able to bend while being kept from collapsing. The bendable portion 4 can be bent by a pair of bending actuator mechanisms 37, 41 as bending drive members for bending the bendable portion 4 up and down.

Further, a hard joint ring 42 is fixed, at one side thereof, to the rear end of the rearmost bending piece 23 which is housed and secured inside the proximal end of the tube 19 covering the bendable portion 4 and, at the other side thereof, to a hard ring-like mouthpiece 33 for the flexible tube portion, the mouthpiece 33 being secured to the distal end of a flexible tube 21 which forms an outer peripheral wall of the flexible tube portion 2. Accordingly, the proximal end of the bendable portion 4 is coupled to the distal end of the flexible tube portion 2 via the joint ring 42.

The hard distal end portion 6 has two holes formed therein to extend in the direction of length and serve as an illumination window and an observation window. The distal end of a light guide 11 for transmitting a ray of illumination light therethrough is fixed in one of the holes via a mouthpiece, and an object lens 13 is fixed in the other hole with a CCD 15, as a solid state image sensor, fixed in the focal plane of the object lens 13.

The light guide 11 extends through both the insert 2 and the universal cord 10. A light guide connector 12a branched from the connector 12 is connected to the light source unit 16 so that a ray of illumination light is supplied from the light source unit 16 to the light guide connector 12a. The ray of illumination light supplied to the light guide connector 12a is transmitted through the light guide 11 and emitted from the distal end surface of the light guide 11 for illuminating a subject in the front.

An optical image of the illuminated subject is focused by the object lens 13, attached to the observation window of the distal end portion 6, on the image sensing plane of the CCD 15. The focused optical image is subjected to photoelectric conversion by the CCD 15. The CCD 15 is electrically connected to the video processor 14 via a signal cable 17 so that upon application of a CCD drive signal from the video processor 14, a photoelectrically converted signal is read out of the CCD 15 and inputted to a video signal processing circuit (not shown) in the video processor 14. The video signal processing circuit produces a standard video signal by which the subject image is displayed on the display monitor 20.

The bending actuator mechanisms 37, 41 are each arranged such that a wire 32 made of a stainless steel is fixed at one end thereof by brazing to a rigid member, in turn fixed to the bending piece 23 at the distal end of the bendable portion 4, and is coupled at the other end thereof to a shape memory alloy wire (hereinafter abbreviated as an SMA wire) 36 having a shape memory function, such as a Ti-Ni alloy, via a wire joint member 34. Further, the SMA wire 36 and part of the wire 32 are inserted through a non-compressive (or non-contractile) member, for example, a coil sheath 38. The proximal ends of both the coil sheath 38 and the SMA wire 36 are fixed to a plug 40 which serves as a free end in the direction of length of the bending actuator mechanism against lengthwise stresses due to bending of the flexible tube portion 2. The distal end of the coil sheath 38 is fixed by brazing to the joint ring 42.

It is to be noted that the overall length of the wire 32 combined with the SMA wire 36 is longer than the bending actuator mechanisms 37, 41 to keep a slack so that when the bendable portion 4 is bent in one direction, the wires on the opposite side will not be too stretched. Also, an insulating tube 44 which doubles as a heat-resistant member is fitted inside the coil sheath 38 to hold electric insulation between the coil sheath 38 and the SMA wire 36. The insulating tube 44 further functions as a passage through which cooling air is to pass.

Figure 3A:
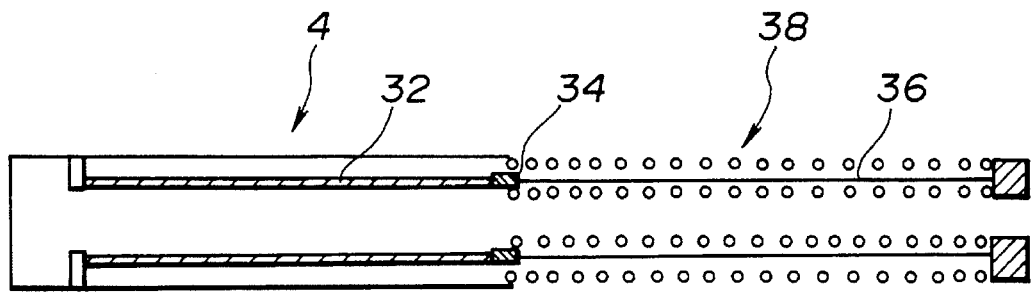
FIGS. 3a–3c are a set of explanatory views showing different conditions of a coil sheath.
Figure 3B:
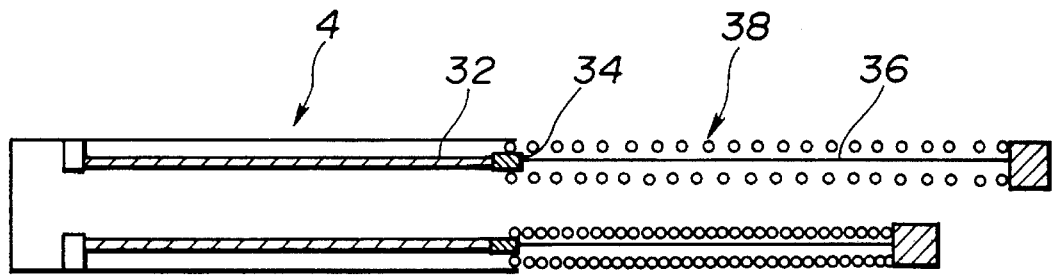
Figure 3C:
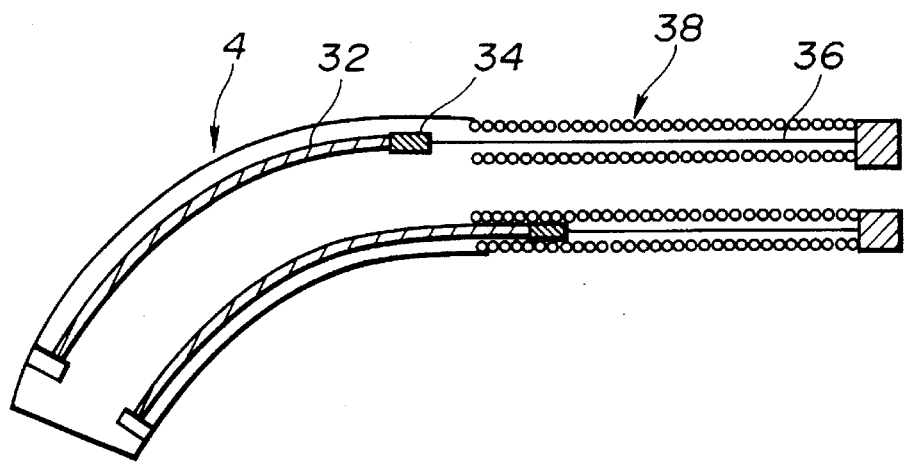

Although the combination of wire 32 and SMA wire 36 has been described above as being longer, the coil sheath 38 may be alternatively wound at such a coarse pitch that an additional length corresponding to the slack of the longer combination of wires is produced, as shown in FIG. 3a. By so doing, the SMA wire 36 is brought into a tightly stretched condition. Under this condition, when the SMA wire 36 on one side is heated to contract as shown in FIG. 3b, the coil sheath 38 is axially tensed on the heat-contracted side into the state of a densely coiled spring. When the heating is continued for further contraction, the wire 32 is pulled in an amount corresponding to the contracted length of the SMA wire 36 to thereby bend the bendable portion 4. At this time, the bending actuator mechanism on the side not heated (i.e., on the upper side in FIG. 3c) contracts the coil sheath 38 into the state of a densely coiled spring for providing a slack necessary to allow the bending. Accordingly, the SMA wire 36 is not required to have a certain slack in a normal condition and the slack length is set beforehand by winding the coil sheath 38 at a coarse pitch, with the result of easier assembling.

Figure 4:
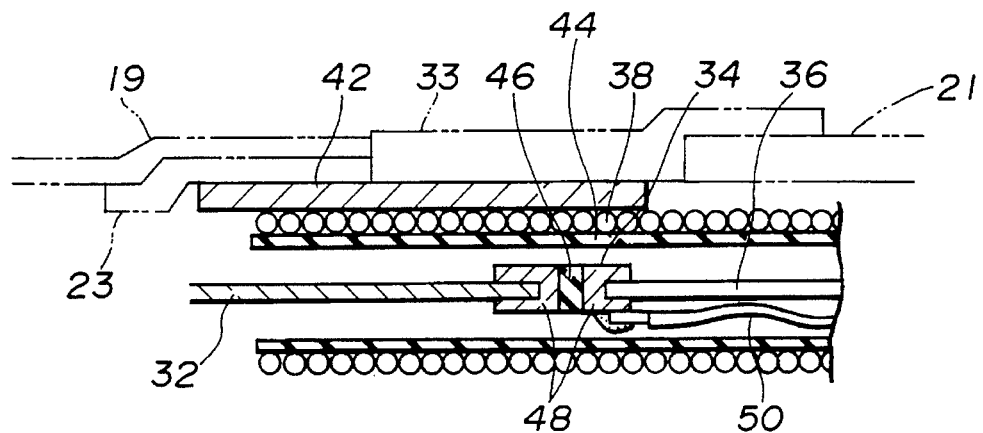

As shown in FIG. 4, the aforesaid wire joint member 34 comprises an insulating member 46 and a pair of metal members 48 bonded to opposite sides of the insulating member 46 in sandwiched relation. The rear end of the wire 32 is fixed to one of the metal members 48, whereas the SMA wire 36 and a lead wire 50 are both fixed to the other metal member 48, the lead wire 50 being electrically connected to the distal end of the SMA wire 36. Notice that the lead wire 50 is entirely covered with an insulating tube except for its connection part to the other metal member 48.

Figure 5A:
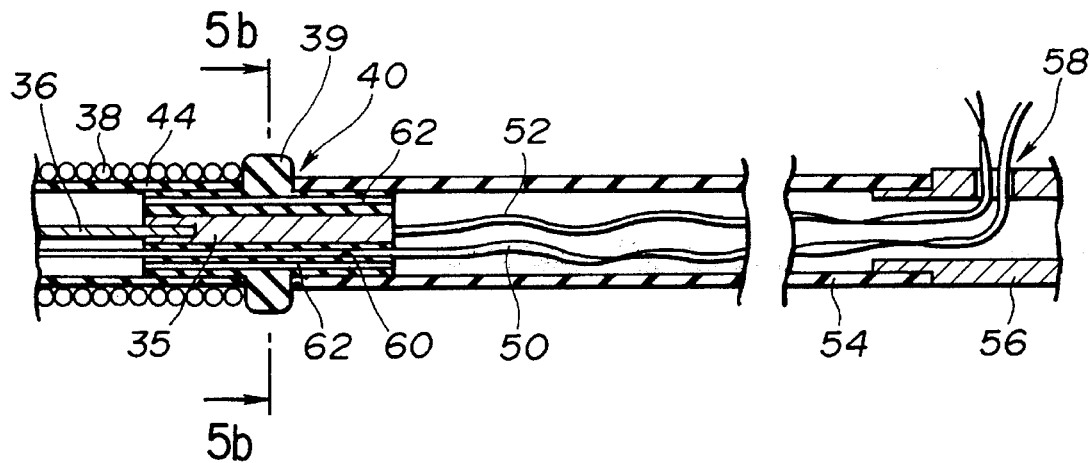
FIGS. 5a–5b are a set of enlarged views showing the configuration of a plug.
Figure 5B:
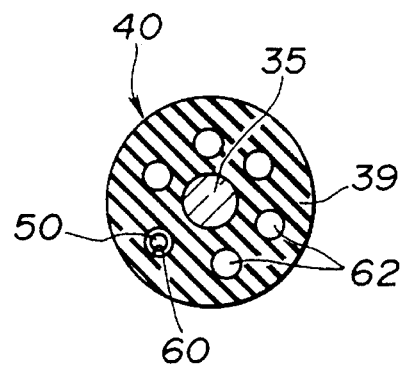

As shown in FIG. 5a, the plug 40 comprises an outer layer 39 formed of an insulating member and an inner layer 35 formed of a metal member. The rear end of the SMA wire 36 is fixed to one end of the inner layer 35 and a lead wire 52 is fixed to the other end of the inner layer 35, with the SMA wire 36 and the lead wire 52 being electrically connected to each other. As shown in FIG. 5b which is a sectional view taken along the line 5b—5b in FIG. 5a, the plug 40 has a lead wire insertion hole 60 and a plurality of ventilation holes 62 all of which holes are formed therethrough, and the lead wire 50 is inserted through the lead wire insertion hole 60.

The coil sheath 38 is connected to one end of the plug 40 and one end of a flexible air tube 54 is connected to the other end of the plug 40. A connector 56 is connected to the other end of the air tube 54 and is provided with a side hole 58 through which both the lead wires 50, 52 can be led out of the air tube 54. Also, the connector 56 can be connected to a solenoid valve described later. It is to be noted that a seal (not shown) is fitted in the side hole 58 to keep air tightness.

Figure 6:
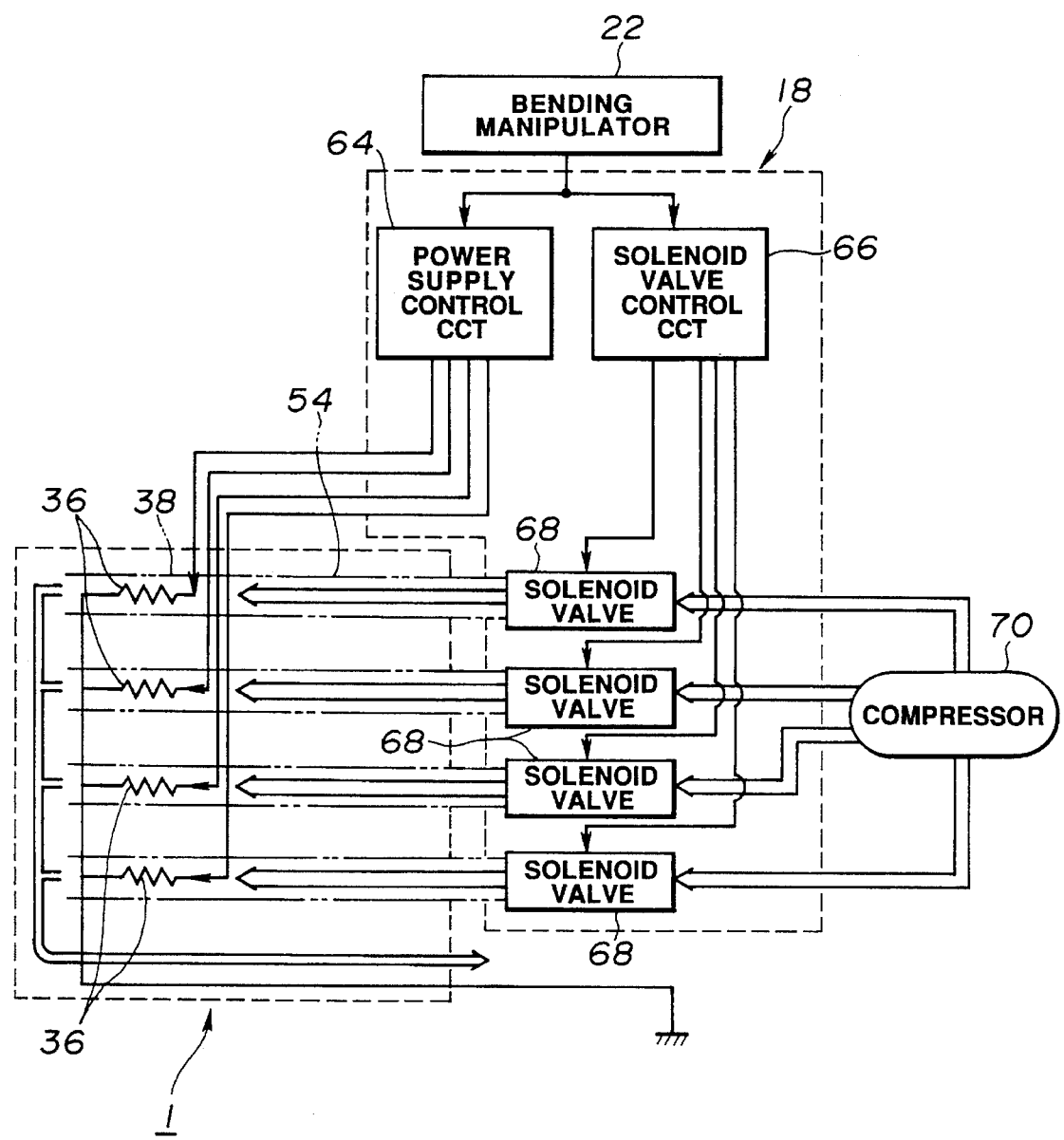

As shown in FIG. 6, the bending controller 18 comprises a power supply control circuit 64 for supplying a drive signal to the four SMA wires 36 to thereby control supply of the electric power and hence heating for control of a bending amount (i.e., a bending angle), four solenoid valves 68 (connected to the respective connectors 56), and a solenoid valve control circuit 66 for controlling opening/closing operations of the solenoid valves 68. The solenoid valves 68 are connected via respective fluid pipes or lines to a compressor 70 for supplying cooling air, so that the solenoid valve control circuit 66 may control cooling of the SMA wires 36 through control of the opening/closing operations of the associated solenoid valves 68.

Further, the power supply control circuit 64 controls a pulse width of the drive signal for each SMA wire 36 by using the PWM (pulse width modulation) method, for example, thereby making control of supply of the electric power and hence heating. There is also provided resistance value detecting means (not shown) which always detects a resistance value of the SMA wire 36 and feeds the detected value back to the power supply control circuit 64, whereby the bending control is made with high accuracy. The power supply control circuit 64 and the solenoid valve control circuit 66 can easily be operated and controlled by a joystick 22a, for example, which constitutes the bending manipulator 22 connected to the bending controller 18.

The control performed by the joystick 22a will now be described. In FIG. 6, the four SMA wires 36 are adapted for the bending directions of UP, DOWN, LEFT and RIGHT, respectively. Here, UP and DOWN stand for the bending directions opposite to each other vertically, while LEFT and RIGHT stand for the bending directions opposite to each other horizontally.

In FIG. 6, when the joystick 22a of the bending manipulator 22a is brought down in a certain direction, a signal from the joystick 22 is inputted to the power supply control circuit 64, whereupon the SMA wire 36 for the direction corresponding to the input signal is supplied with the electric power for heating. Simultaneously, the signal is also inputted to the solenoid valve control circuit, whereupon the solenoid valve 68, normally opened, for the direction corresponding to the input signal is controlled to be closed. By way of example, at the same time when the bending manipulator 22 sends a signal for instructing to heat the SMA wire 36 in the UP direction (i.e., at the uppermost position in FIG. 6) the solenoid valve 68 for the UP direction is controlled to be closed. Accordingly, the SMA wire 36 under heating is controlled such that it is prevented from being cooled to thereby increase the heating efficiency of the SMA wire 36 and achieve an improvement in the bending operability.

Notice that although the solenoid valve 38 has been described above as keeping it normally opened, the present invention is not limited to this embodiment and, as an alternative, the solenoid valve 38 may be normally closed. In this case, the control performed by the joystick 22a proceeds as follows. Upon the signal from the joystick 22a being inputted to the power supply control circuit 64, the SMA wire 36 for the direction corresponding to the input signal is supplied with the electric power for heating. Simultaneously, the signal is also inputted to the solenoid valve control circuit, whereupon the solenoid valve 68, normally opened, for a direction opposite to the direction corresponding to the input signal is controlled to be closed. By way of example, at the same time when the bending manipulator 22 sends a signal for instructing to heat the SMA wire 36 in the UP direction, the solenoid valve 68 for the DOWN direction opposite to the UP direction is controlled to be opened. Accordingly, the SMA wire 36 in opposite relation to the SMA wire 36 contracted under heating is forcibly cooled, but the other SMA wires 36 which require no cooling are controlled to be not cooled. In other words, since the SMA wire 36 for the direction to be contracted under heating through the control is heated and the SMA wire 36 for the opposite direction is forcibly cooled, it becomes possible to positively cool the SMA wire 36 for the opposite direction and thus achieve an improvement in the bending operability.

Figure 7:
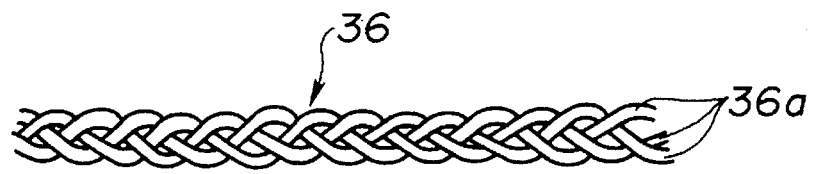
Figure 8A:
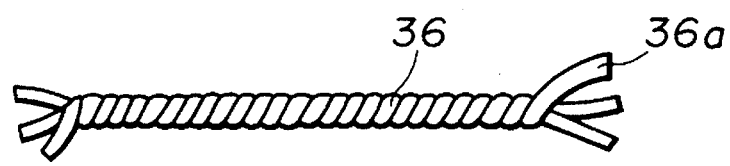
FIGS. 8a–8c are a set of side views showing another example of the structure of the SMA wire.
Figure 8B:
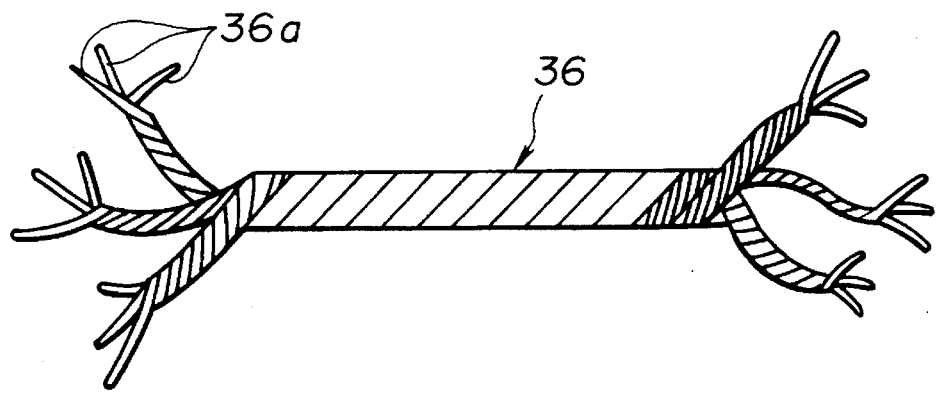
Figure 8C:
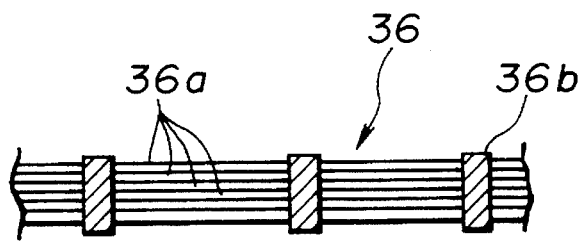

Although the SMA wire 36 may be in the form of a single wire, the structure comprising a plurality of strands, e.g., SMA wire strands 36a braided as shown in FIG. 7, is more preferable than the structure comprising a single wire in the point of providing a greater degree of flexibility. Alternatively, like modifications as shown in FIGS. 8a to 8c, the SMA wire 36 may be in the form of a rope prepared by twisting shape memory alloys together each being a single wire, or a large-diameter rope prepared by twisting or bundling a plurality of such twisted ropes together.

Figure 9:
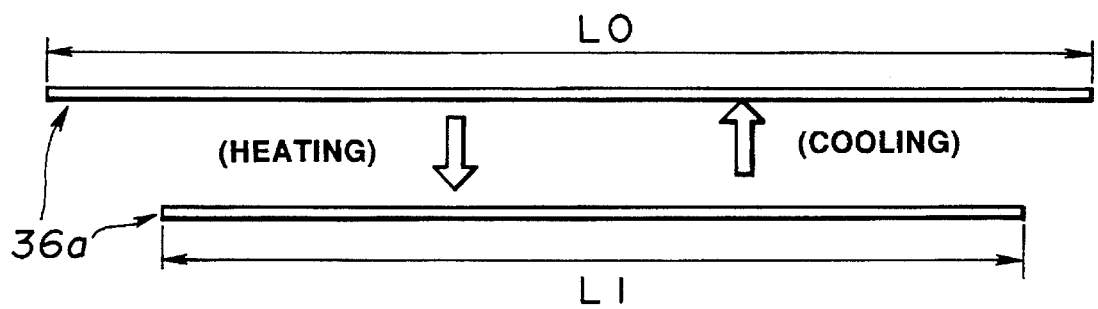

The SMA wire 36 shown in FIG. 7 has the structure comprising the SMA wire strands 36a braided together. Each of the SMA wire strands 36a memorizes, for example, a length L0 (see FIG. 9) obtained when it is cooled down below the temperature Mf at which transformation comes to an end (via the temperature Ms at which it starts) in the cooling mode, and a length L1 (L1<L0) obtained when it is heated up above the temperature Af (Mf<Af) at which transformation comes to an end (via the temperature As at which it starts) in the heating mode. This change in length of the SMA wire strand is reversible. (Note that the SMA wire strand exhibits temperature hysteresis.)

Accordingly, the SMA wire 36 comprising the SMA wire strands 36a braided together similarly changes its length reversibly dependent on a change in temperatures. In addition to the bending actuator mechanism, the endoscope 1 also incorporates the light guide 11 for illumination, signal lines for the CCD, and so forth. The SMA wire 36 thus prepared by braiding the SMA wire strands 36a together has such a benefit that while a traction force on the order of several kilograms is required to pull and bend the wire 32, a sufficient traction force can be provided as a whole of the SMA wire 36 even if the traction force for each SMA wire strand 36a is weak. Other benefits are in a larger degree of flexibility than the single SMA wire, a greater surface area to provide superior heat radiating characteristics, a higher cooling speed after stopping supply of the electric power and hence heating, and an improved response speed in the bending.

Additionally, even if any one of the SMA wire strands 36a is cut off, the remaining SMA wire strands 36a could still produce the traction force required.

Figure 10:
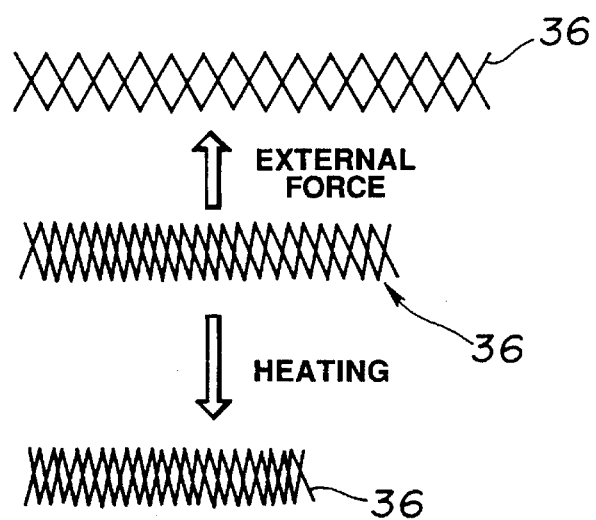

Moreover, with the SMA wire 36 comprising the SMA wire strands 36a braided together, as shown in FIG. 10, the SMA wire 36 has spring resiliency in itself so that it is easily extended by application of an external force under non-heating and is contracted under heating. Accordingly, the braided structure of the SMA wire 36 enables that the slack of the SMA wire 36 necessary on the side not supplied with the electric power can be provided by contraction characteristics due to the spring resiliency. The need of giving the SMA wire 36 with slack which is required when the SMA wire 36 has the form of a single wire, or winding the coil sheath 38 at a coarse pitch as shown in FIG. 3 is thus eliminated to facilitate assembling.

The SMA wire 36 comprising the SMA wire strands 36a twisted together into a rope as shown in FIG. 8a functions in a like manner to the above one having the braided structure. The SMA wire 36 prepared by twisting three ropes, each as shown in FIG. 8a, together into a single large-diameter rope as shown in FIG. 8b also has a similar function. Further, the SMA wire 36 may be prepared by bundling the plurality of SMA wire strands 36a together and tightening them by means of restriction members 36b, such as caulking metal chisels or resin tubes, fitted at appropriate intervals alongside thereof as shown in FIG. 8c. In short, the structure comprising a plurality of SMA wire strands is preferable to the structure comprising a single SMA wire.

Figure 11:
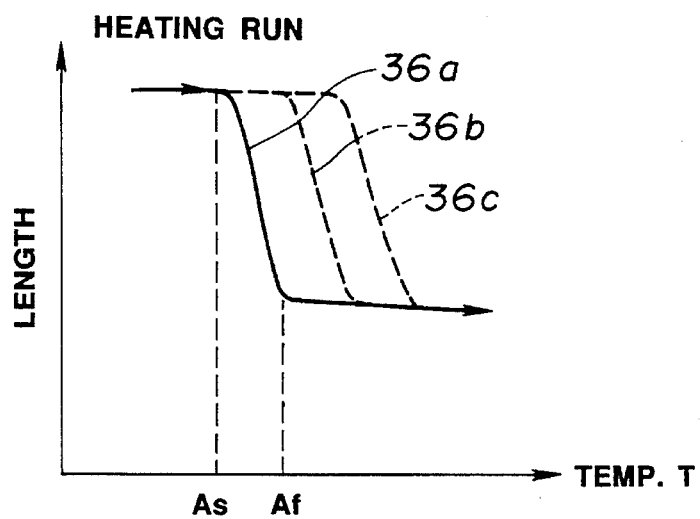
Figure 14:
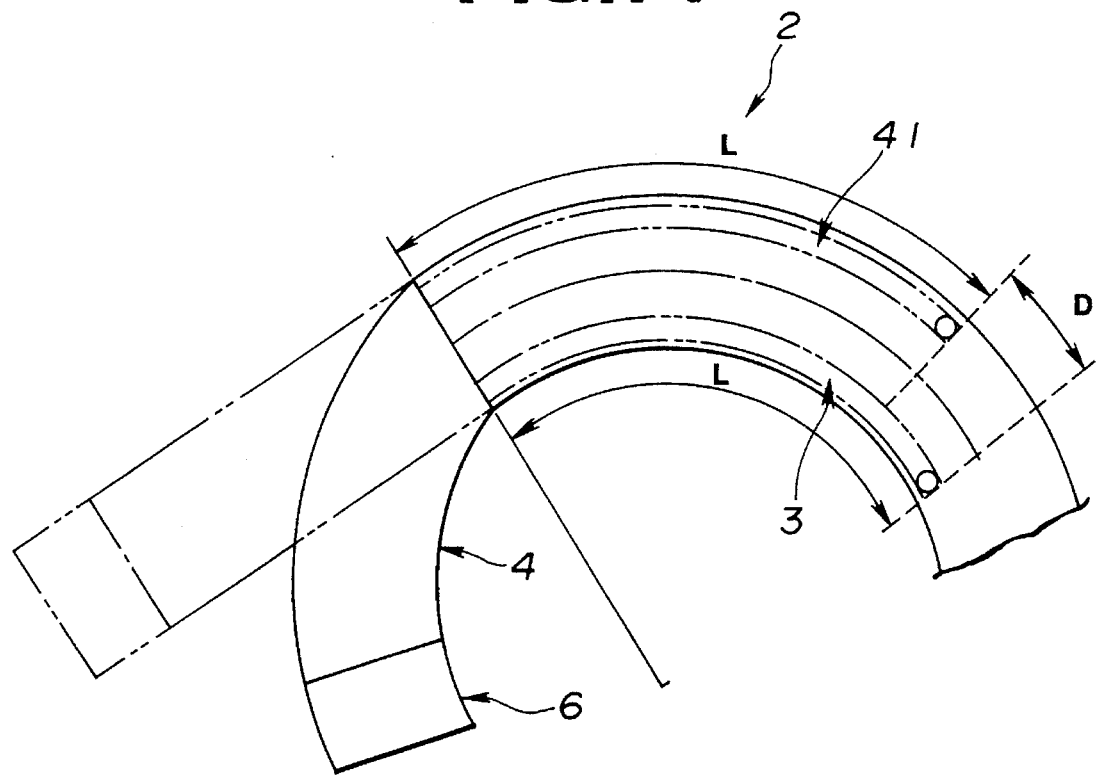

The plurality of SMA wire strands 36a jointly making up the SMA wire 36 have characteristics of the same transforming temperature (a solid line in FIG. 11 shows how each SMA wire strand 36a changes its length dependent on temperatures T under heating, for example). Because of the plural SMA wire strands 36a having the same temperature of transformation, it is possible to set a large amount of change in tension of the bending actuator mechanism caused by extension or contraction due to cooling or heating.

Figure 12:
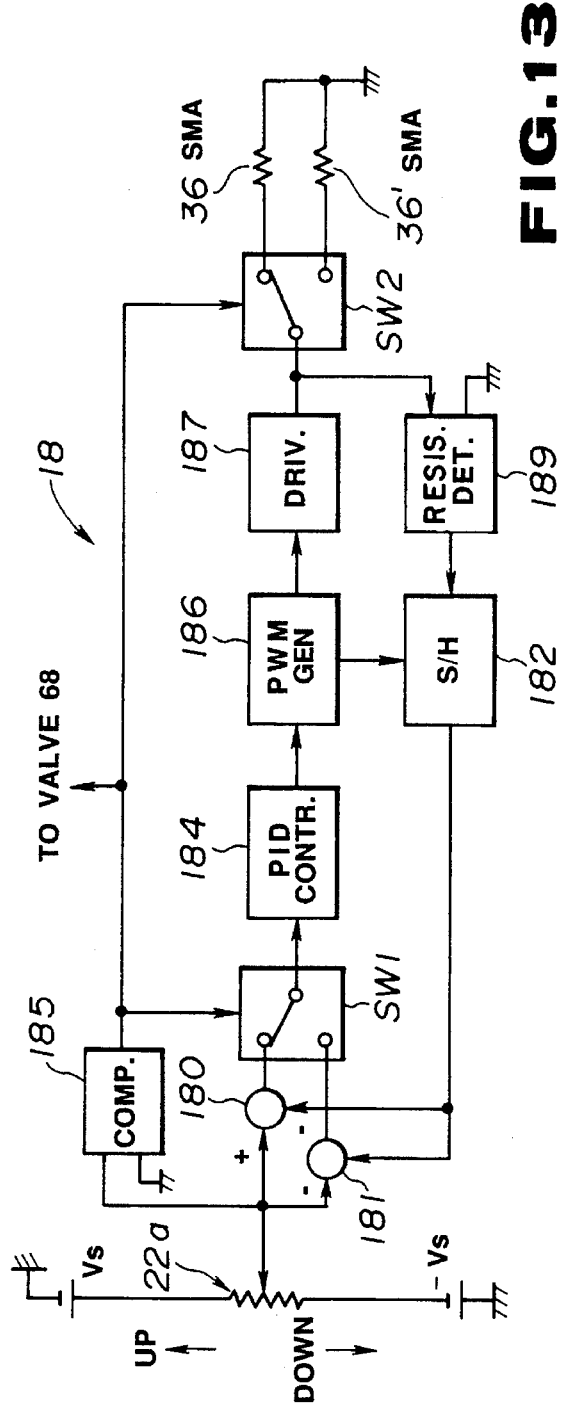

In this embodiment, the bending controller 18 arranged as shown in FIG. 12, for example, makes control such that the resistance value of the SMA wire 36 becomes a value corresponding to an inclination angle of the joystick 22a of the bending manipulator 22 when manually operated. The resistance value control by the bending controller 18 is performed in such a manner as to be able to set states of many different resistance values (i.e., states of many different lengths) within a temperature range of transformation where the axial length of the SMA wire 36 is reversibly changed in super-elastic fashion (the temperature range of transformation under heating being from As to Af in FIG. 11 and also substantially from T1 to T2 in FIG. 13).

Referring to FIG. 12, when the joystick 22a (indicated by an equivalent variable resistor; although only one variable resistor related to manipulation in the direction up and down, by way of example, is illustrated for the sake of brevity, the similar operation is carried out in the direction to the left and right as well) is manually operated, a bending angle signal corresponding to the resistance value set upon the manipulation of the joystick 22a, i.e., a signal having its voltage value varied dependent on the bending angle, is inputted to subtracters 180 and 181 where the input signal is subtracted from a detection signal corresponding to the resistance value which is held by a sampling/holding circuit 182. The joystick 22a produces a positive voltage value dependent on the tilting amount when the joystick is tilted upwardly, a negative voltage value dependent on the tilting amount when it is tilted downwardly, and a zero value when it is at a neutral position.

Outputs of the subtracters 180 and 181 are inputted to a PID controller 184 via a switch SW1. The output of the joystick 22a is also applied to a comparator 185 and compared with the voltage of zero for detecting in which one of the directions up and down the joystick 22a is tilted. The output resulted from the comparison is used to control switching operation of the switch SW1. When the output of the joystick 22a is positive, by way of example, the output of the subtracter 180 is led to the PID controller 182, as shown in FIG. 12.

Depending on the output of the subtracter 180 or 181, the PID controller 184 issues a control signal to the PWM generator 186 for controlling such a pulse width.

When the input to the PID controller 184 is positive, by way of example, the PID controller 184 issues a control signal to the PWM generator 186 for increasing the pulse width to thereby make feedback control so that the corresponding SMA wire 36 or 36' (36, 36' in FIG. 12 standing for the SMA wires to be heated for bending in the upward and downward directions, respectively) is further heated to make the input to the PID controller 184 become zero.

The PWM generator 186 operates to change the pulse width dependent on the control signal and output the changed pulse width to a driver 187, an output of the driver 187 being applied to the SMA wire 36 or 36' via a switch SW2. The switch SW2 is also controlled in its switching operation in response to the output of the comparator 185 as with the switch SW1.

On the other hand, a resistance value detector 189 detects the resistance value of the SMA wire 36 or 36' in the form of a voltage value and then outputs the detected value to the subtracters 180 and 181 via the sampling/holding circuit 182.

The subtracters 180 and 181 each determine the difference between the aforesaid bending angle signal and a signal corresponding to the resistance value provided from the sampling/holding circuit 182, and then outputs the determined difference to the PID controller 184 for feedback control. Through this feedback control, the voltage value corresponding to the resistance value of the SMA wire is controlled to become coincident with the voltage value produced upon manual operation of the bending manipulator 22. Notice that the output of the comparator 185 is also used for opening and closing control of the solenoid valve 68.

Figure 13:
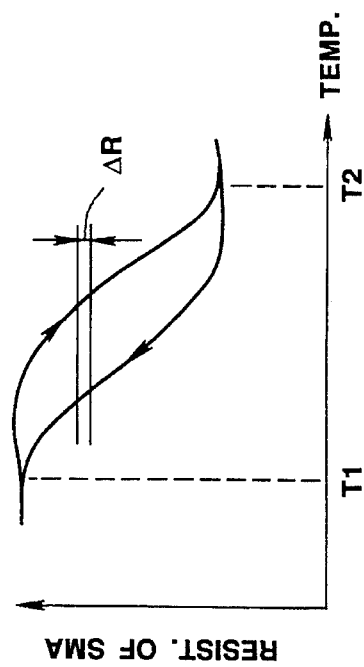

Through the above resistance value control based on feedback control, it is possible to make setting into states of many different resistance values (these resistance value states corresponding to lengths of the SMA wire 36 essentially in one-to-one relation) within the temperature range of transformation from T1 to T2 on the order of a resistance value error ΔR, by way of example, as shown in FIG. 13. Therefore, even when the SMA wire 36 is formed by using the SMA wire strands 36a with the same transforming temperature, the length of the SMA wire 36 can finely be set in a variable manner. As a result, this embodiment is able to eliminate the drawback of the prior art (Japanese Patent Laid-Open No. 61-197,770) that the similar fine control function cannot be achieved unless SMA wires having different temperatures of transformation from each other are used in a large number.

With the endoscope 1 of this embodiment, because of the bending actuator mechanisms 37, 41 being each constituted by the coil sheath 38 which is not compressive in the direction of length thereof, when the SMA wire 36 is contracted by being supplied with the electric power from the power supply control circuit 64 for heating, the overall length always remains the same in the portion of the non-compressive coil sheath 38 and thus the tensile force due to the contraction of the SMA wire 36 is all imposed on the bendable portion 4 to bend it. On the other hand, the solenoid valve 68 is opened by the solenoid valve control circuit 66 to supply cooling air from the compressor 70 to the SMA wire 36, thereby extending the SMA wire 36 under cooling.

Moreover, when bending the bendable portion 4 in a condition that the flexible tube portion 2 is being bent, since the coil sheaths 38, non-compressive in the direction of length thereof, of the bending actuator mechanisms 37, 41 are fixed to the respective plugs 40 each serving as a free end in the direction of length of the bending actuator mechanism against lengthwise stresses due to bending, the bending actuator mechanisms 37, 41 relatively move the plugs 40 (through an amount of movement indicated by D) without changing their overall length L. As a result, the tensile force due to contraction of the SMA wire 36 by heating with supply of the electric power or extension thereof by cooling is all imposed on the bendable portion 4. Stated otherwise, in any states of the flexible tube portion 2 being not only extended straight but also inserted to ducts or the like sharply curved, the bendable portion 4 can positively be bent by heating the SMA wire 36 with supply of the electric power or cooling the same. It is to be noted that two-dot-chain lines in FIG. 8 represent the state of the SMA wire before starting the bending operation.

According to the first embodiment of the present invention, as explained above, regardless of bent conditions of the flexible tube portion 2, the bendable portion 4 can be bent by using the bending manipulator 22 easily and accurately into any desired direction in a short period of time through the power supply control circuit 64 and the solenoid valve control circuit 66.

Also, since the flexible tube portion 2 and the bendable portion 4 are coupled by the joint ring 42 to each other and the wire 32 and the SMA wire 36 are coupled by the wire joint member 34 to each other, the working efficiency of assembly and maintenance of the endoscope 1 can be improved by constructing the joint ring 42 and the wire joint member 34 in a detachable manner.

Even in the case of modifying the foregoing first embodiment such that a major part of the SMA wire strands 36a jointly making up the SMA wire 36 is selected to have the same temperature of transformation and only a minor part of the SMA wire strands 36a is selected to have the different temperature of transformation from the one above, the modification also functions substantially in the same manner as the first embodiment.

Although the plurality of SMA wire strands 36a jointly making up the SMA wire 36 have been described as having the same temperature of transformation in the foregoing first embodiment, the SMA wire 36 may be prepared by other bundling SMA wire strands 36b, 36c which have different temperatures of transformation as indicated by dot lines in FIG. 11, together with the SMA wire strands 36a represented by the solid line in FIG. 11. The first embodiment thus prepared by using the SMA wire strands 36a, 36b, 36c which have different temperatures of transformation from one another can also control the bending amount in a like manner. In this modification, too, the first embodiment controls (i.e., control based on detection of the resistance value) the setting of the SMA wire 36 into any of plural different lengths within a temperature range of transformation of at least one SMA wire strand 36i (i=a or b or c).

Figure 15:
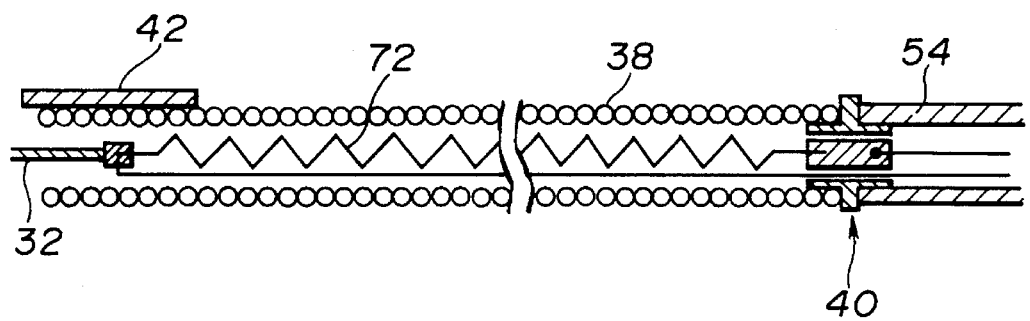

Although the SMA wire 36 has been employed in the above, this embodiment is not limited to the use of wire-like SMAs. Alternatively, for example, there may be used an SMA spring 72 in spiral form which has a dense pitch at high temperatures and a coarse pitch at low temperatures, as shown in FIG. 15, so that the amount of extension and contraction can be increased in comparison with the SMA wire 36 to cut down the length of the bending actuator mechanisms or to make the total bending amount greater.

Figure 16A:
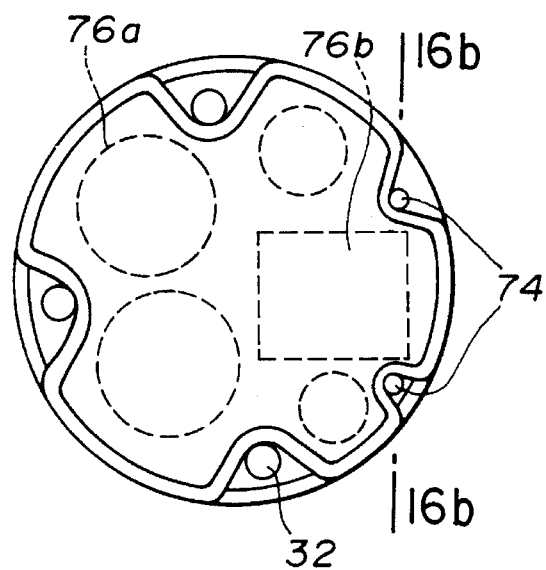
FIGS. 16a–16b are a set of structural views showing a modification of a fixing member at the distal end side of a bending wire.
Figure 16B:
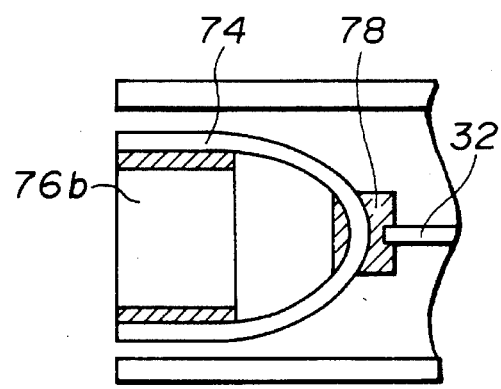

Moreover, one end of the wire 32 has been explained as being fixedly brazed to the rigid member 31 in turn fixed to the distal end of the bendable portion 4. In the case of several components 76a, 76b built in the distal end side of the bendable portion 4 as shown in FIG. 16a, however, it is possible to avoid an interference with the built-in component 76b by coupling the wire 32 to a U-shaped wire 74 using a joint member 78 (see FIG. 16b which shows a sectional view taken along the line 16b—16b in FIG. 16a).

Figure 17:
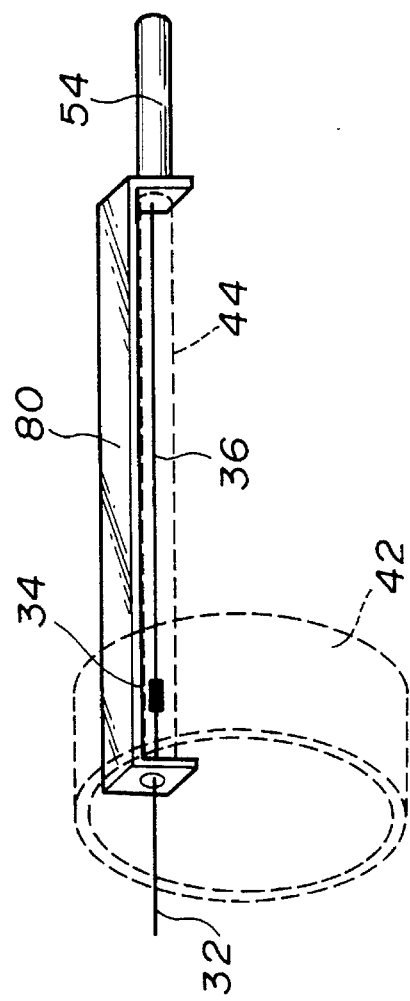

In addition, although the coil sheath 38 is used as a non-compressive member in the above description, this embodiment is not limited to use of the coil sheath and an elastic plate 80 may instead be employed which has the form of nearly U in section as shown in FIG. 17 such that it will not deform under a non-compressive force in the direction of length thereof and is likely to bend easily under a bending moment. Use of the elastic plate 80 results in a smaller wall thickness of the flexible tube portion than the case of using the coil sheath 38, thereby enabling a reduction in the diameter of the flexible tube portion.

Although the description above has been made in connection with the bending actuator mechanisms for the upward and downward directions, it is needless to say that similar bending actuator mechanisms are also provided for the leftward and rightward directions. These bending mechanisms can be operated independently of one another for each direction.

Further, although the shape memory alloy member is used as a mechanism member for bending the insert in the above explanation, this embodiment is not limited to the use of shape memory alloys and the mechanism member may be formed of shape memory resins or any other suitable actuators.

Additionally, the endoscope of this embodiment may be of the straight-viewing type or side-viewing type and may be in the form of an optical one using an image fiber (i.e., fiber scope) or an electronic one. The endoscope may also be used for medical purposes as well as for industrial purposes.

Figure 18:
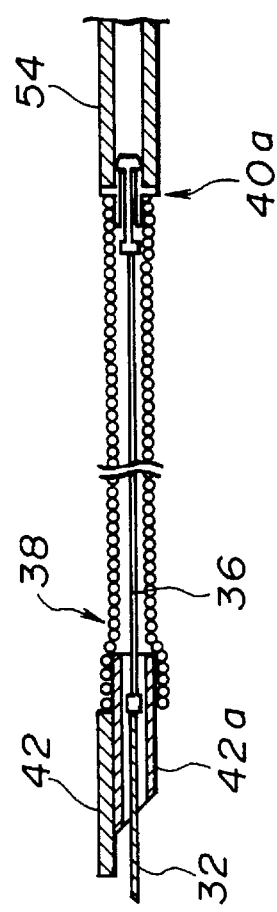

FIG. 18 shows the coil sheath 38 and part of the SMA wire which is inserted through the coil sheath 38 in a modification of the above first embodiment. This modification is almost the same as the first embodiment except for the joint manner. More specifically, while the distal end of the coil sheath 38 is fixed by brazing to the joint ring 42 in the first embodiment, a pipe 42a is brazed to the joint ring 42 and the distal end of the coil sheath 38 is fixedly press-fitted over the pipe 42a in the modification, as shown in FIG. 18.

Further, as shown in FIG. 19b, a plug 40a has the structure comprising an outer layer 51 and three pipes 51a, 51b and 51c arranged inside the outer layer 51. The proximal end portion of the SMA wire 36 is fixed such that, as shown in FIG. 19a, an insulating wire 53 is coupled at one end thereof to the SMA wire 36 and secured at the other end thereof in place by using an end caulking member 55. The end caulking member 55 has its distal end formed into a tapered shape, for example, and is disposed to locate substantially at the center of the pipe 51a. The distal end portion of the coil sheath 38 is fixed by brazing to the three pipes 51a, 51b and 51c.

In addition, the lead wires 50, 52 for supplying the electric power to the SMA wire 36 are respectively extended through the remaining two pipes, e.g., the pipes 51b, 51c.

The other construction is the same as the first embodiment and thus will not be described here.

This modification is intended to improve the manner of fixing the coil sheath 38 which is directly brazed to the joint ring 42 in the first embodiment. Specifically, since the coil sheath 38 is fixed by press-fitting it over the pipe 42a brazed to the joint ring 42, replacement, repair and other maintenance work of the SMA wire, which are required in the event of a breakage or the like of the SMA wire 36 and must be carried out by taking the SMA wire 36 out of the coil sheath 38, can easily be performed just by pulling the press-fitted coil sheath 38 rearwardly to withdraw it from the pipe 42a. This leads to an improvement in the repair service.

The other operation and advantageous effect are the same as those in the first embodiment.

FIG. 20 is a sectional view showing the distal end side of a flexible tube portion 2b in a probe device according to a second embodiment of the present invention.

As shown in FIG. 20, the flexible tube portion 2b has its distal end region arranged such that wires 81 and 83 having different lengths from each other are coupled by respective wire joint members 34 to the corresponding SMA wires 36 covered with coil sheaths 82, 84. Plugs 85 and 87 are relatively spaced in the direction of length thereof through the difference in length between the wires 81 and 83 so that the two SMA wires 36 have an equal length.

Bulged or larger-diameter joints 86 and 88 surrounding the respective wire joint members 34 each have a sufficient space to allow the wire joint member 34 to smoothly slide upon extension and contraction of the SMA wire 36, and are provided to be relatively offset in the direction of length thereof by a distance corresponding to the difference in length between the wires 81 and 83. The rest of the construction and operation are the same as those in the first embodiment.

With the flexible tube portion 2b thus constructed, since the bulged joints 86 and 88 each surrounding the wire joint member 34 and increasing the diameter of the coil sheath are shifted in position from each other, the percentage of cross-sectional areas of the coil sheaths 82, 84 occupying in a cross-sectional area of the flexible tube portion 2b can be made smaller to reduce the diameter of the flexible tube portion 2b. The other advantageous effects are the same as that in the first embodiment.

Figure 21:
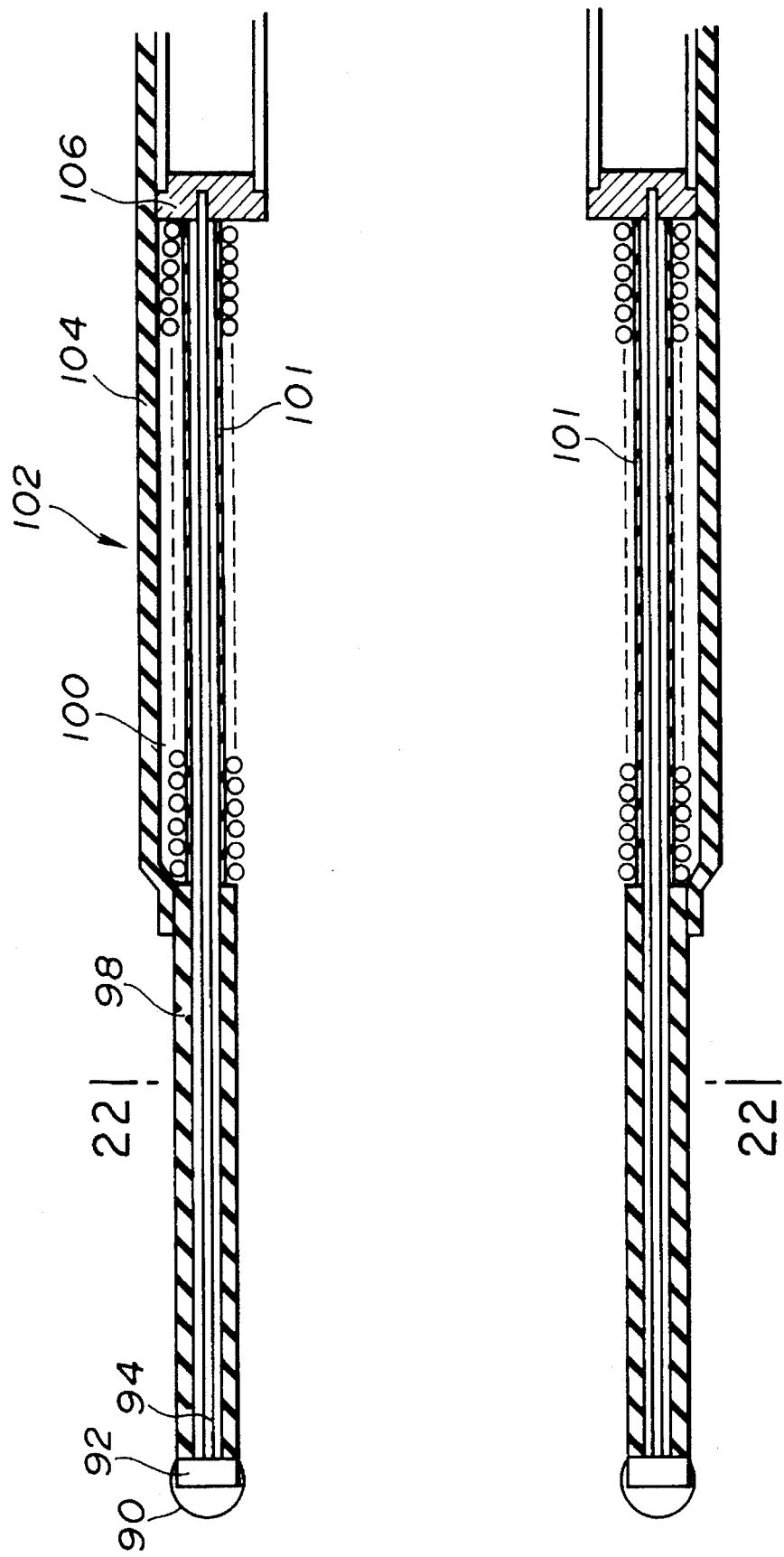
FIG. 21 is a sectional view showing the distal end side of a flexible tube in a third embodiment of the present invention.

FIG. 21 is a sectional view showing the distal end side of a flexible tube portion in a probe device according to a third embodiment of the present invention.

As shown in FIG. 21, a guide tube 102 inserted through an elongate endoscope (not shown) or an inspection probe (not shown) which has no members to be driven for bending, such as the aforesaid bending pieces, comprises a flexible tube portion 104, and a multi-lumen tube 98 provided to extend from the distal end of the flexible tube portion 104 and formed of a heat-resistant resin such as silicon or Teflon. The flexible tube portion 104 and the multi-lumen tube 98 are connected to each other by fixing the rear end of the latter to the distal end of the former by bonding, for example. The multi-lumen tube 98 has such characteristics that it is hard to compress in the direction of length thereof, but is pliable in the radial direction.

A rigid member 92 is provided at the distal end of the multi-lumen tube 98, while an SMA wire 94, inserted through the multi-lumen tube 98 and the distal end region of the flexible tube portion 104, and a lead wire (not shown) for supplying the electric power to the SMA wire 94 are both fixedly connected at one end thereof to the rigid member 92. Part of the SMA wire 94 is inserted through a non-compressive member, for example, a coil sheath 100. The other end of the SMA wire 94 and the proximal end of the coil sheath 100 are fixedly connected to a plug 106 serving as a free end in the direction of length thereof against lengthwise stresses. Further, a flexible tube 101 is inserted within the coil sheath.

The plug 106 has a plurality of lead wire insertion holes and a plurality of ventilation holes (all not shown) bored therethrough. The lead wires (not shown) are extended through the lead wire insertion holes, whereas cooling air can be supplied into lumens of the multi-lumen tube 98 via the ventilation holes and the tube 101. The distal end of the multi-lumen tube 98 is covered with a cover member 90 for protection.

Figure 22:
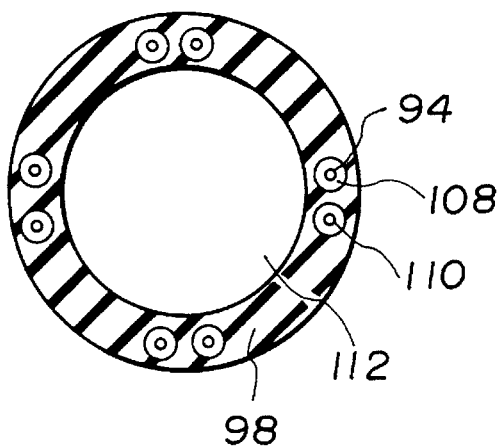
FIG. 22 is a sectional view taken along the line 22—22 in FIG. 21.

As shown in FIG. 22, the multi-lumen tube 98 has eight small-diameter lumens 108 positioned in the circumferential direction thereof and a single large-diameter lumen 112 defined at the center. Those eight small-diameter lumens 108 are separated into four sets, each comprising two lumens, arranged with angular intervals of 90° between every adjacent two sets. Of the two small-diameter lumens in each set, the SMA wire 94 is inserted through one lumen and the lead wire 110 for supplying the electric power to the SMA wire 94 is inserted through the other lumen. The rest of the construction and operation are the same as those in the first embodiment.

After inserting an elongate endoscope (not shown) or an inspection probe (not shown), which has no bending capability, through a central hole of the guide tube 102 thus constructed, observation or inspection can be performed by utilizing the bending mechanism of the guide tube 102. Further, since a bendable portion comprises the multi-lumen tube 98 made of a resin, the SMA wire 94 can be insulated electrically with ease, as a result of which the wire and the wire joint member required in the first embodiment to keep electrical insulation can be dispensed with. The other advantageous effect is the same as that in the first embodiment.

Figure 23:
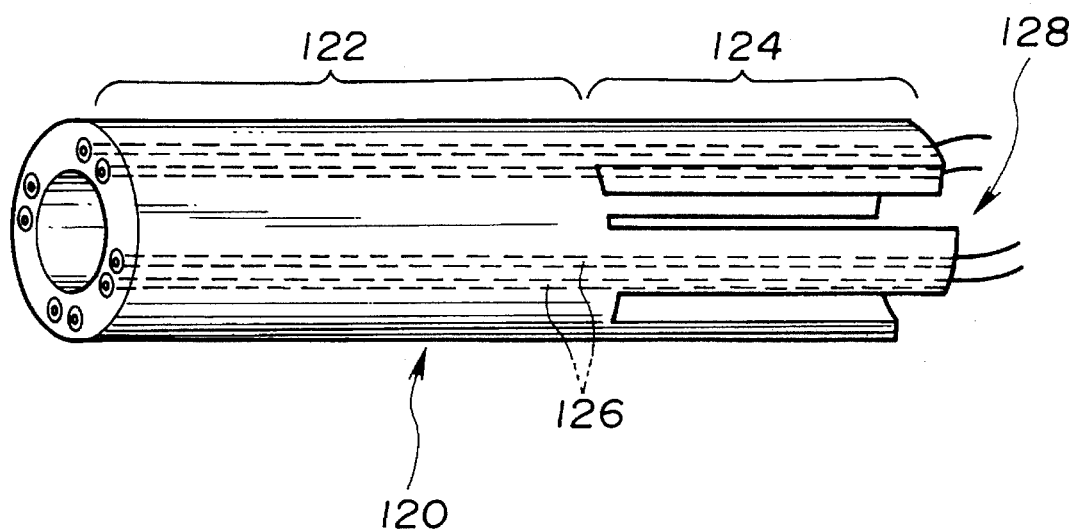
FIG. 23 is a perspective view of the distal end side of a flexible tube in a fourth embodiment of the present invention.

FIG. 23 is a perspective view showing the distal end side of a flexible tube portion according to a fourth embodiment of the present invention.

As shown in FIG. 23, the distal end region of the flexible tube portion comprises a multi-lumen tube 120 formed of a heat-resistant resin such as silicon or Teflon, for example. A cross-section of the distal end portion of the multi-lumen tube 120 has the same structure as shown in FIG. 22 of the third embodiment. In the proximal end side of the multi-lumen tube 120, there are provided four cut-outs 128 at such locations as leaving four sets of small-diameter lumens (not shown), each set being consisted of two lumens. With that structure, the multi-lumen tube 120 is made up by two components, i.e., a multi-lumen rod portion 124 having the cut-outs 128, and the remaining bendable portion 122. An SMA wire 126 is inserted through each set of two small-diameter lumens (not shown), while being turned back at the distal end of the multi-lumen tube 120, and is secured at the other end of the multi-lumen tube 120. The other construction is the same as that in the first embodiment.

In the fourth embodiment thus constructed, when the SMA wire 126 is supplied with the electric power for heating, it is contracted to the length determined by shape memory. On this occasion, because the SMA wire 126 is arranged nearly along the central axis of each rod segment of the multi-lumen rod portion 124, there occurs a stress only in the direction of the central axis, but no bending moment in the multi-lumen rod portion 124. Meanwhile, because the SMA wire 126 is located at a position offset from the central axis of the bendable portion 122, a contraction force of the SMA wire 126 is more likely converted into a bending action in the bendable portion 122. Accordingly, the amount of contraction of the SMA wire 126 is all converted into the bending action of the bendable portion 122. The rest of the operation is the same as that in the first embodiment.

With the fourth embodiment, the bendable portion and the bending actuator mechanism can be manufactured as a unitary part, thereby enabling simplification of the structure necessary for connection, insulation, etc. and thus to reduce the diameter of the multi-lumen tube. The other advantageous effects are the same as that in the first embodiment.

FIG. 24 shows a lengthwise section of a flexible tube portion according to a fifth embodiment of the present invention.

Since this flexible tube portion is almost the same as that in the first embodiment, only the difference therebetween will be explained below, while identical components to those in the first embodiment are denoted at the same reference numerals and will not be described here.

As shown in FIG. 24, the bendable portion 4 extending from the distal end of the flexible tube portion 2 is comprised of the plural bending pieces 23, and the wire 32 fixed to the rigid member 31, provided at the distal end of the bendable portion 4, is coupled by the wire joint member 34 to the distal end of an SMA wire 130 described later. The proximal end of the SMA wire 130 is coupled to the distal end of a wire 132 by a joint member 131. The proximal end of the wire 132 is connected to the distal end of a male screw 133, held in mesh with a hollow member 134 which is fixed to the proximal end side of the flexible tube portion 2 and has female threads tapped in the circumferential surface of its hollow space, so that a degree of tension of a bending transmission system comprising the wire 32, the SMA wire 130 and the wire 132 may be adjusted by rotating the male screw 133 at the proximal end side thereof. This bending transmission system is provided in four sets for bending the bendable portion 4 up and down as well as left and right. Thus, as shown in FIG. 25, the total four hollow members 134 are provided with angular intervals of 90° between every adjacent twos.

Figure 26A:
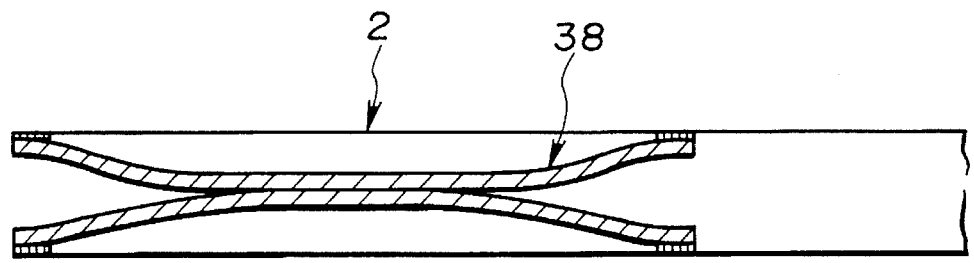
FIGS. 26a–26b are a set of explanatory views for explaining conditions of the coil sheath within a flexible tube in a fifth embodiment of the present invention.
Figure 26B:
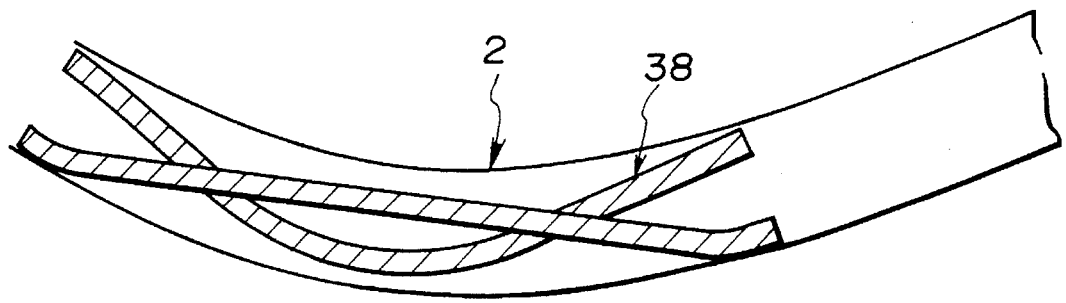

As shown in FIG. 26a, the coil sheath 38 is provided to have slack when the flexible tube portion 2 is in a straight condition. By so arranging, when the endoscope 1 is inserted through a meandered duct or pipe, the flexible tube portion 2 is curved as shown in FIG. 26b, whereupon the coil sheath 38 on the inner side with respect to the center of curvature has more slack, but the coil sheath 38 on the outer side is tightened with no slack. Even in such a case, the SMA wire 130 extended through each coil sheath 38 as a non-compressive member maintains its overall length without undergoing a stress. Further, with the SMA wire 130 being pliable, the SMA wire 130 can be extended and contracted while it is being curved following the shape of the coil sheath 38.

The other constructions, operations and advantages are the same as those in the first embodiment.

Figure 27:
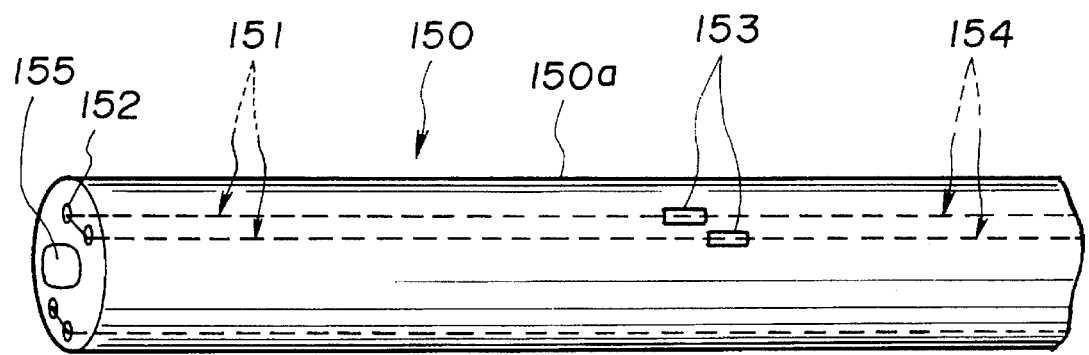
FIG. 27 is a perspective view showing the distal end side of a catheter in a sixth embodiment of the present invention.

FIG. 27 is a perspective view of the distal end side of a catheter according to a sixth embodiment of the present invention.

As shown in FIG. 27, a catheter 150 as a probe comprises a multi-lumen tube 150a made of silicon with a central lumen 155 being formed to insert a small-diameter scope, an appliance or the like (not shown), or to inject a medical fluid therethrough. Peripheral lumens 152 are grouped into pairs, each comprising two lumens, such that an SMA wire 151 is inserted through one of the paired lumens 152 and then reversely through the other lumen 152 after being turned back at the distal end of the catheter 150. Both ends of the SMA wire 151 are connected to lead wires 154 via caulking members 153 which are fixed in the lumens 152, respectively.

By supplying the electric power through the lead wires 154, the SMA wire 151 is heated for contraction. Since the caulking members 153 are fixed in the lumens 152, the positions of the caulking members 153 remain immobile, as a result of which the catheter 150 is bent.

In this modification, because of the SMA wire 151 being inserted through the lumens 152, friction is generated upon extension and contraction of the SMA wire 151, meaning that large extension and contraction forces are required to cause the SMA wire 151 to extend and contract. Therefore, the SMA wire 151 has the structure of a braid prepared by braiding a plurality of SMA wire strands together as shown in FIG. 7. Additionally, since the catheter 150 of the sixth embodiment is smaller in diameter than the endoscope of the first embodiment, the SMA wire 151 needs a higher degree of pliability and thus consists of very thin SMA wire strands.

Figure 28:
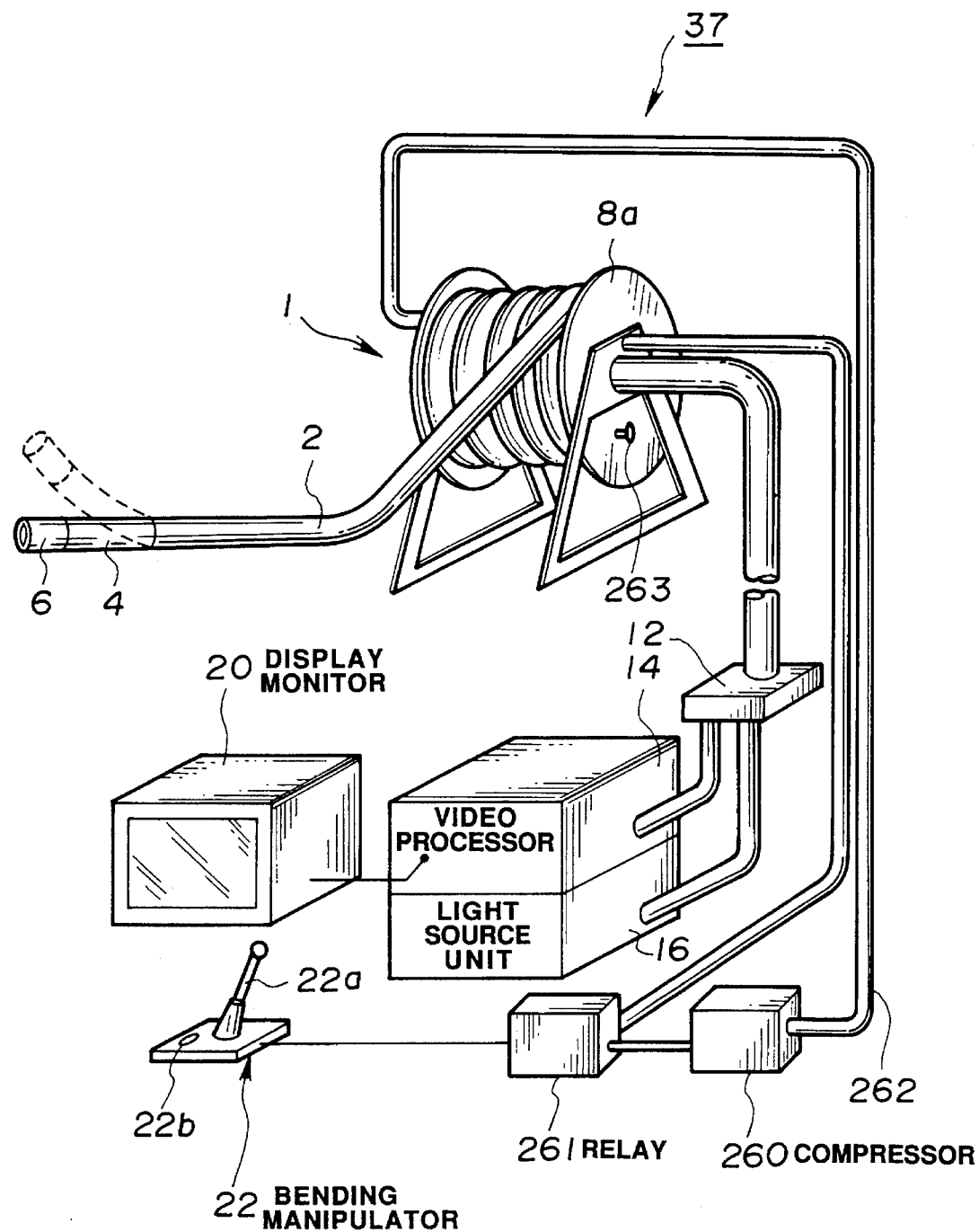

An endoscope device 37 for industrial purposes according to a seventh embodiment of the present invention, shown in FIG. 28, is almost the same as the endoscope device 27 according to the first embodiment except for that the controller 18 in the endoscope device 27 according to the first embodiment is removed away and some of the functions is to be effected by the controller 18 are installed in a drum 8a.

More specifically, as shown in FIG. 28, the endoscope device 37 for industrial purposes according to this embodiment comprises the drum 8a which incorporates therein the functions of the solenoid valves 68, the power supply control circuit 64 and the solenoid valve control circuit 66 all provided in the controller 18 of the first embodiment as shown in FIG. 6, a compressor 260 for supplying cooling air as a cooling fluid to the drum 8a via an exterior tube 262, and a relay 261 for supplying the electric power to the compressor 260, the solenoid valves, the power supply control circuit and the solenoid valve control circuit which are all provided in the drum 8a but not shown, as well as the bending manipulator 22.

The relay 261 is also capable of transmitting a signal from the bending manipulator 22 to the compressor 260 and the solenoid valves, the power supply control circuit and the solenoid valve control circuit which are all provided in the drum 8a but not shown. An exhaust plug 263 is further provided on the lateral side of the drum 8a so that the cooling air supplied to the interiors of the industrial-purposed endoscope 1 and the drum 8a may be discharged through the exhaust plug 263.

Figure 29A:
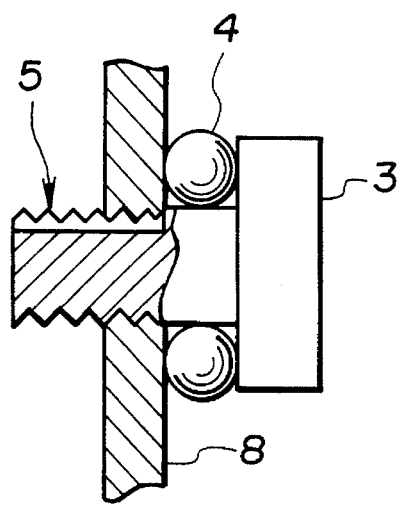
FIGS. 29a–29b are a set of explanatory views for explaining operation of an exhaust plug provided in a drum.
Figure 29B:
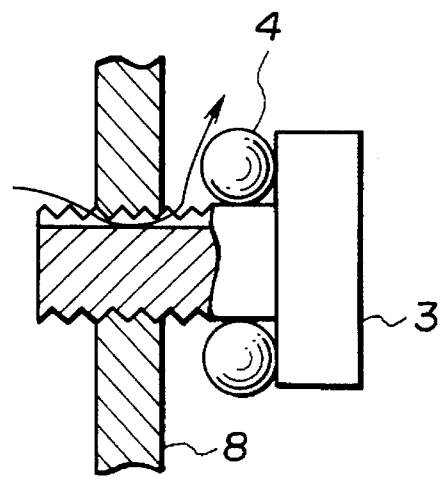

As shown in FIG. 29a, the exhaust plug 263 comprises a bolt formed with a groove extending in the axial direction, the bolt being held in mesh with an exhaust port defined through a lateral wall of the drum 8a. During periods of storage, the exhaust plug 163 is fastened to establish an air-tight sealing with the aid of an O-ring 264. During periods of use, the exhaust plug 263 is loosened to depart the O-ring 264 away from the lateral surface of the drum 8a, as shown in FIG. 29b, whereupon the cooling air is allowed to exhaust as indicated by an arrow.

The other construction is the same as that in the first embodiment.

With the thus-arranged endoscope device 37 for industrial purposes according to the seventh embodiment, the respective component units can be reduced in size as compared with the first embodiment. In addition, when an opening (not shown) for exhausting the supplied cooling air therethrough is provided in the proximal end portion of the insert of the industrial-purposed endoscope 1 in the first embodiment, there is a fear that the opening might be clogged with mud, slush or the like to prevent exhaust of the cooling air dependent on environment in which the industrial-purposed endoscope 1 is used. As opposed to that, by providing the exhaust plug 263, which is not to be touched during periods of the operation, on the lateral side of the drum 8a in this embodiment, the cooling air can be exhausted positively and, therefore, the SMA wires 36 can be cooled without increasing pressures in the industrial-purposed endoscope 1 and the drum 8a.

Figure 30A:
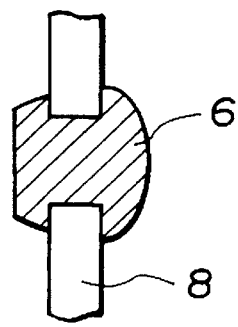
Figure 30B:
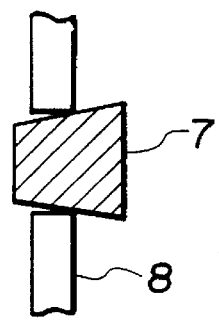

It is to be noted that, as shown in FIGS. 30a and 30b, a rubber-made plug 266 or 267 may be fitted into the exhaust port in place of the exhaust plug 263 during periods of storage.

The other operations and advantages are the same as those in the first embodiment.

Figure 31:
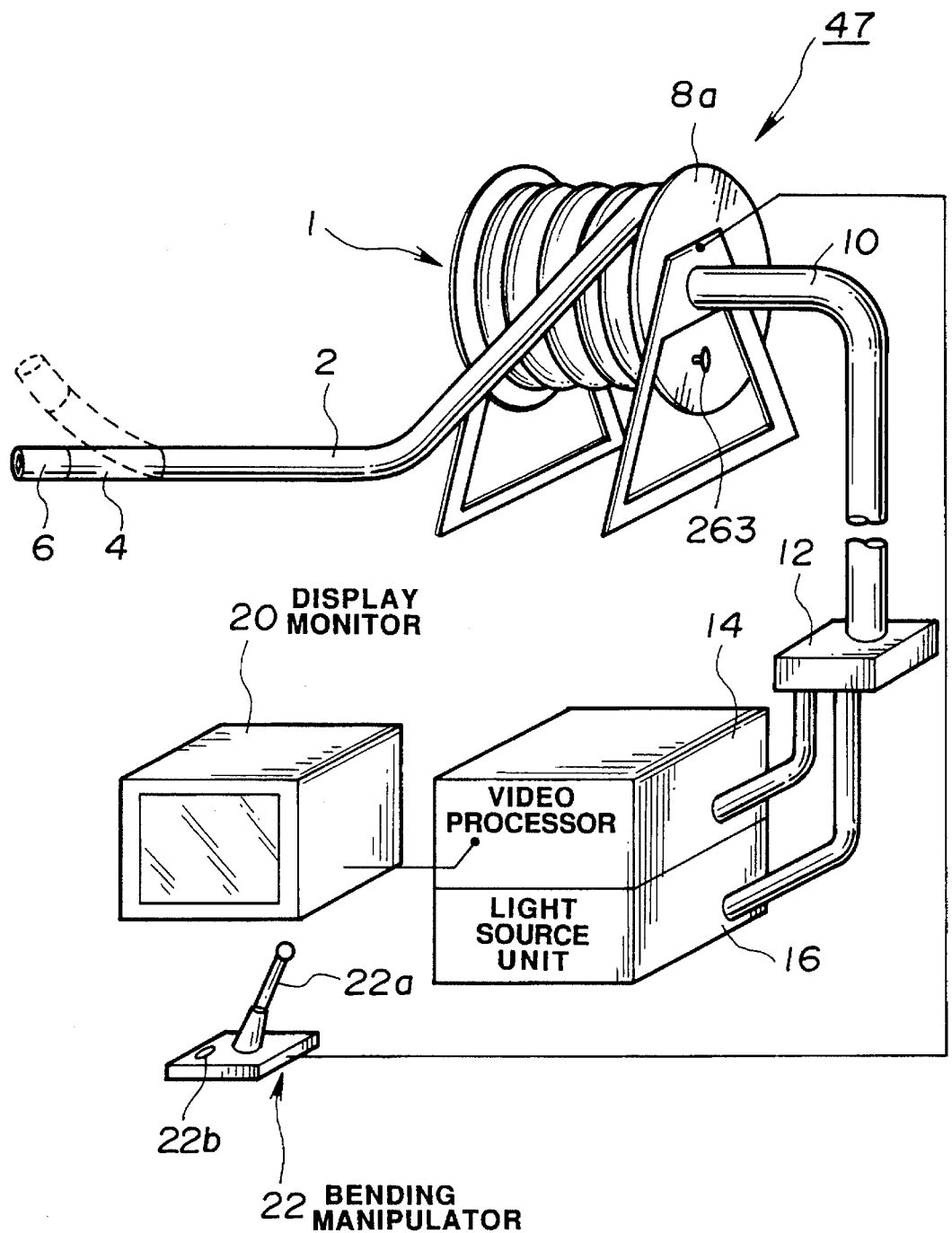
FIG. 31 is a diagram showing the entire configuration of an endoscope device for industrial purposes according to an eighth embodiment of the present invention.

FIG. 31 shows an endoscope device 47 for industrial purposes according to an eighth embodiment of the present invention.

The endoscope device 47 for industrial purposes according to the eighth embodiment is almost the same as the endoscope device 37 according to the seventh embodiment except that the functions of the compressor 260 and the relay 261 in the endoscope device 37 according to the seventh embodiment are also incorporated in a drum 8b. In other words, the functions of the controller 18 in the first embodiment are all incorporated in the drum 8b.

The other construction is the same as that in the seventh embodiment.

With the thus-arranged endoscope device 47 for industrial purposes according to the eighth embodiment, because of using the drum 8b which incorporates both the function of the controller 18 and the function of the drum 8 in the first embodiment together, the system can be constructed of a smaller number of components than in the first and seventh embodiments.

Figure 32:
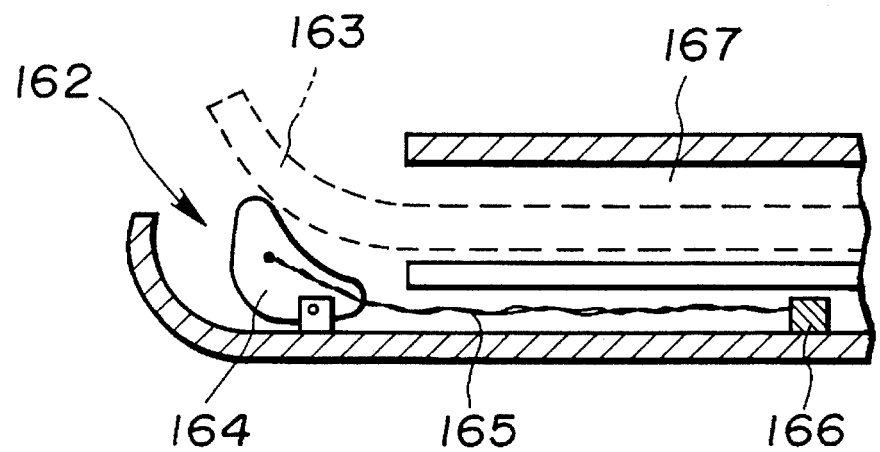
FIG. 32 is a sectional view of a forceps channel at the distal end portion of a side-viewing type endoscope according to a first application example of the SMA wire.

As an application example of the SMA wire shown in FIG. 7, there will now be described an embodiment for improving the operability of cannulation of a side-viewing type endoscope, by way of example. This side-viewing type endoscope has a forceps channel 167 defined therein as shown in FIG. 32 which is a sectional view taken in the direction of length thereof. A forceps 163 indicated by broken lines is inserted through the forceps channel 167.

At the distal end portion of the forceps channel 167, a forceps raising stage 162 in the form of a cam 164 is provided so as to raise the forceps 163 in the side-viewing direction. One end of an SMA wire 165, like that as shown in FIG. 7, is connected to part of the cam 164 and the other end of the SMA wire 165 is connected to a rigid member 166 fixed in the side-viewing type endoscope. By supplying the electric power via lead wires (not shown) to the SMA wire 165 for heating through the rigid member 166, the SMA wire is contracted to drive the forceps raising state 162.

In the prior art where an operating wire is used in place of the SMA wire 160, there arises a problem that a sufficient stroke cannot be taken dependent on bent conditions of the bendable portion of the side-viewing type endoscope. With this embodiment, however, use of the SMA wire 160 can always ensure operation to raise the forceps regardless of any bent conditions of the bendable portion of the side-viewing type endoscope. Because of the braided structure, the SMA wire 165 has pliability and also has a capability of extending and contracting sufficiently to raise the forceps.

A second application example of the SMA wire shown in FIG. 7 will be described next.

Figure 33:
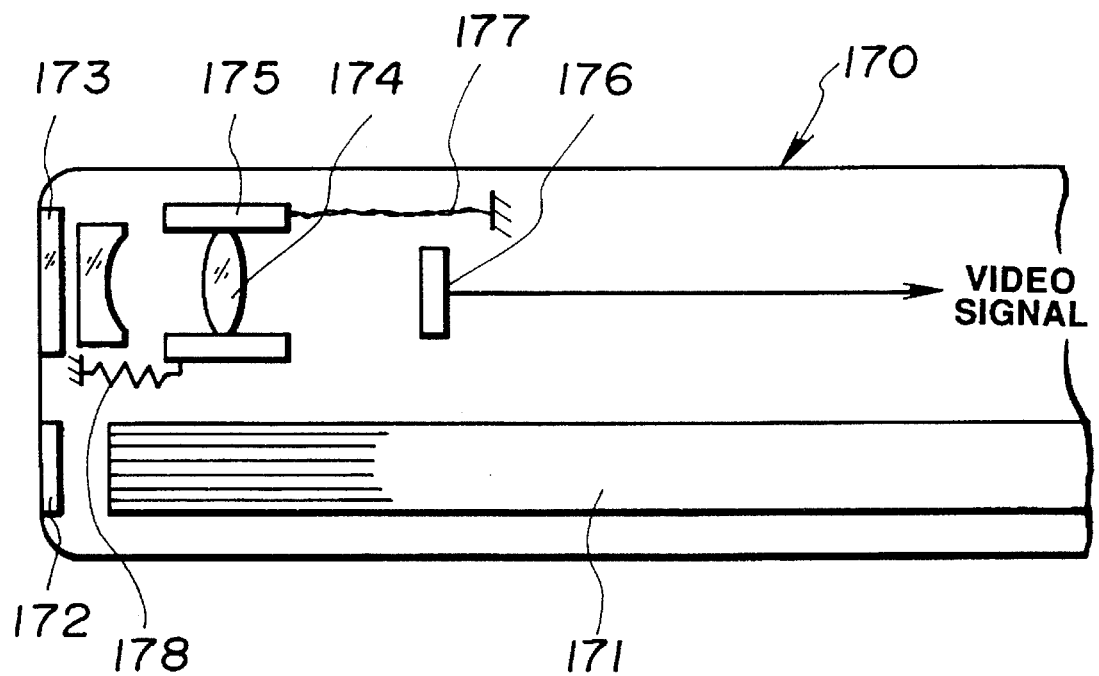
FIG. 33 is a sectional view of the distal end portion of an endoscope according to a second application example of the SMA wire.

FIG. 33 is a sectional view of the distal end portion of an endoscope according to the second application of the SMA wire.

As shown in FIG. 33, an endoscope 170 comprises a light guide 171 for transmitting a ray of illumination light emitted from a light source (not shown), and a solid state image sensor or detector (SID) 176 for sensing or picking up a subject image under observation. The ray of illumination light propagating through the light guide 171 is projected from an illumination window 172 at the distal end of the endoscope 170 for illuminating a subject (not shown). A ray of light reflected by the subject enters an optical system including an object lens 174 through an observation window 173 at the distal end of the endoscope 170, and is focused on the end face of the solid state image sensor 176.

The object lens 174 is provided with a focusing mechanism 175 to make the subject image focused precisely on the end face of the solid state image sensor 176. An SMA wire 177 having the structure as shown in FIG. 7 is connected to the focusing mechanism 175, and a biasing spring 178 is associated with the focusing mechanism 175 in opposite relation to the SMA wire 177.

With the above construction, by supplying the electric power via lead wires (not shown) to the SMA wire 177 for heating to contract the same at any time, the object lens 174 is moved in the predetermined direction to effect the focusing operation as desired.

Accordingly, the compact focusing mechanism can be realized by employing the SMA wire 177 which has the braided structure as shown in FIG. 7.

An endoscope device according to a ninth embodiment of the present invention, equipped with a unit for driving and controlling the bendable portion, will be described below.

Figure 34:
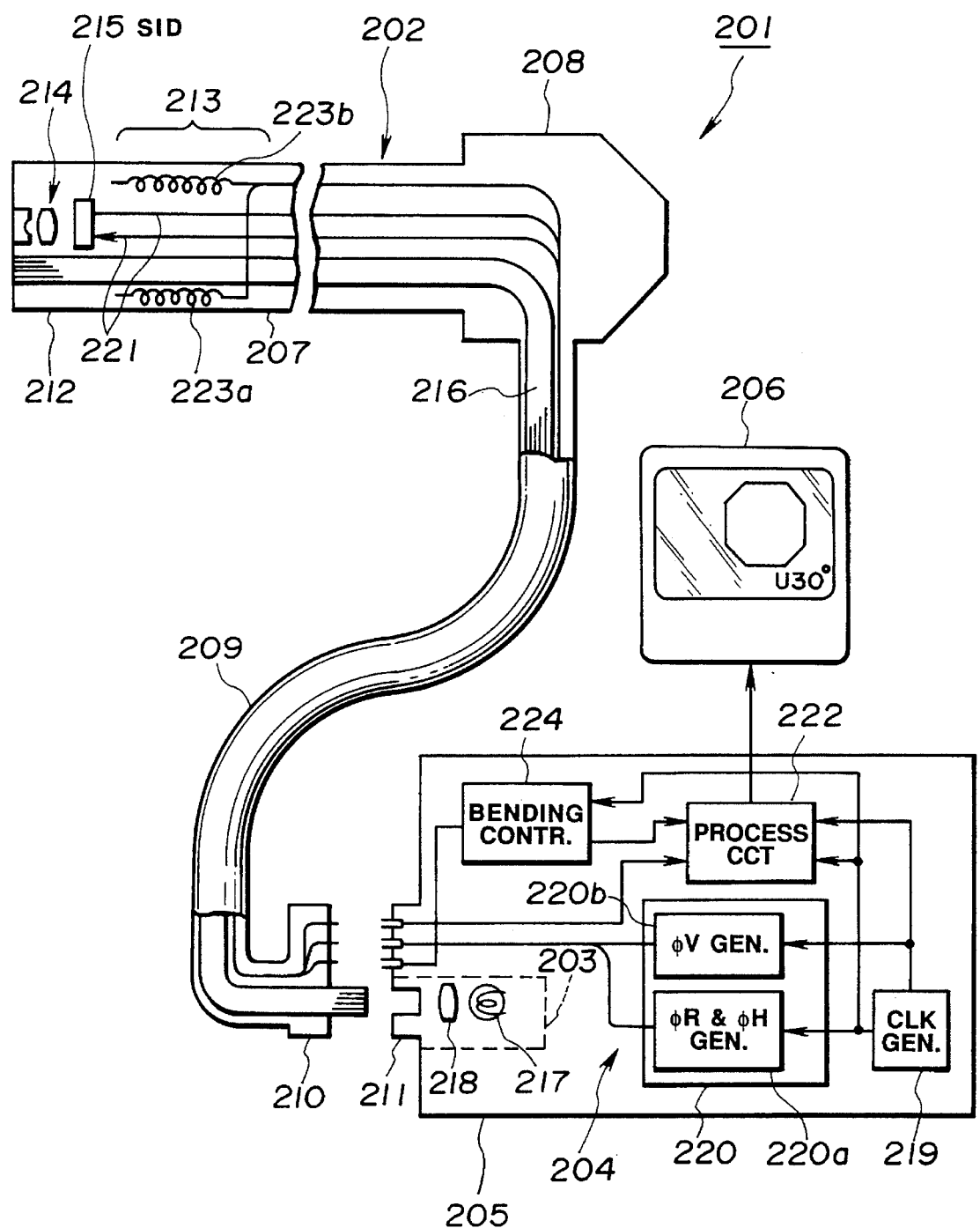

An endoscope device 201 shown in FIG. 34 comprises an electronic endoscope 202 for inspecting the interior of a living body or the like, a video processor 205 which incorporates therein a light source unit 203 for supplying a ray of illumination light to the electronic endoscope 202 and a signal processing circuit 204 for processing signals supplied to and received from image sensing means, and a monitor 206 connected to the video processor 205.

The electronic endoscope 202 comprises an elongate insert 207 having flexibility, a larger-diameter operating section 208 provided to continuously extend from the rear end of the insert 207, and a universal cord 209 laterally extending from the operating section 208. A connector 210 provided at the end of the universal cord 209 is detachably connected to a connector jack 211 provided on the video processor 205.

In the distal end side of the insert 207, there are provided a hard distal end portion 212 and a bendable portion 213 in this order from the distal end of the insert 207. The distal end portion 212 includes an object lens system 214, and the image sensing surface of a solid state image sensor (SID) 215 is disposed at the focus position of the object lens system 214.

A light guide 216 having its emergent end disposed in the distal end portion 212 of the insert 207 is extended through the insert 207, the operating section 208 and the universal cord 209, and has its incident end fixedly disposed in the connector 210. A ray of illumination light from a light source 217 provided in the light source unit 203 of the video processor 205 is condensed by a lens 218 to enter the incident end of the light guide 216.

When the ray of illumination light from the light source 217 is emitted from the emergent end of the light guide 216 and illuminated to a subject, an optical image of the subject is focused on the image sensing surface of the solid state image sensor 215.

On the other hand, the signal processing circuit 204 of the video processor 205 includes a clock signal generator 219 and a driver 220. When a clock signal generated from the clock signal generator 219 is inputted to the driver 220, the driver 220 creates drive signals for the solid state image sensor 215. The driver 220 is comprised of a reset and horizontal transfer pulse generator 220a which generates a reset pulse φR and a horizontal transfer pulse φH, and a vertical transfer pulse generator 220b which generates a vertical transfer pulse φV.

The vertical transfer pulse φV, reset pulse φR and horizontal transfer pulse φH are applied to the solid state image sensor 215 via a signal line 221.

When the above drive signals from the driver 220 are applied to the solid state image sensor 215, the optical image focused on the image sensing surface of the solid state image sensor 215 is subjected to photoelectric conversion and the resulting signal is inputted to a process circuit 222 of the signal processing circuit 204 provided in the video processor 205. The process circuit 222 takes in the input signal and outputs a video signal to the monitor 206.

Figure 35:
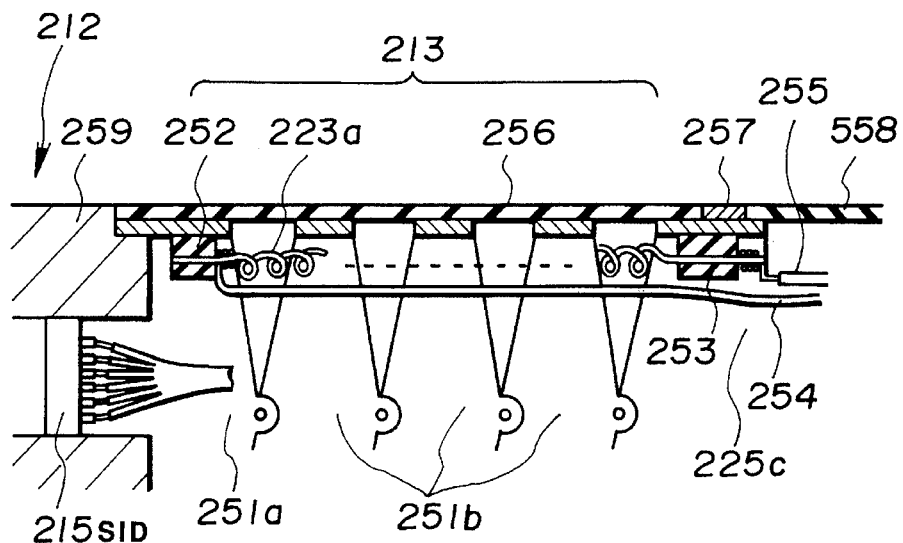

In the bendable portion 213 of the insert 207, a pair of shape memory alloys (SMAs) 223a, 223b in the form of coil springs are arranged in the inner circumferential surface of the bendable portion 213 at positions symmetrical with respect to the central axis thereof and also extended in the axial direction. Each of the SMAs 223a, 223b has the structure comprising a plurality of strands wound into a spiral or coiled shape as shown in FIG. 35, by way of example. In this embodiment, each SMA 223a (223b) has its front end fixed via an insulating member 252 to a foremost one 251a of the first stage among a plurality of bending pieces jointly making up the bendable portion 213, and its rear end fixed via an insulating member 253 to a rearmost bending piece 251c of the last stage of the bendable portion 213. The front and rear ends of the SMA 223a are conducted to one of the ends of lead wires 254, 255, respectively, and the other of the ends of the lead wires 254, 255 are conducted to a bending controller 224.

The bending pieces 251a, jointly making up the bendable portion 213 are covered along the outer circumference thereof with a flexible tube 256, the rear end of this tube 256 being connected via a ring 257 to a tube 258 covering the flexible tube portion. Notice that the SID 215 is fixed to a hard member 259 forming the distal end portion 212.

When the SMA 223a or 223b is heated in response to a control signal from the bending controller 224 in the signal processing circuit 204 of the video processor 205, the heated SMA 223a or 223b is transformed from a coarse-pitch coil into a dense-pitch coil, whereupon the bendable portion 213 is bent in the direction of causing the SMA 223a or 223b transformed into a dense-pitch coil to locate on the inner side of the bending.

Also, bending angle signal data of the bendable portion 213 detected by the bending controller 224 is inputted to the process circuit 222. As a result, the bending angle signal is superposed on the video signal indicative of the endoscope image to thereby display U30° in the lower side of the screen of the monitor 6 as shown in FIG. 34, for example, which stands for the bending angle of 30° in the upward direction.

Figure 36:
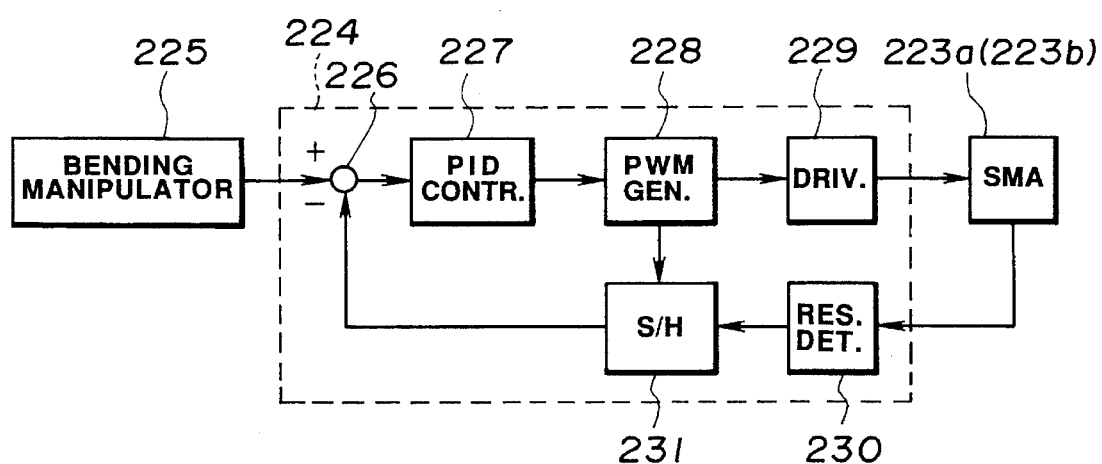

The configuration of the bending controller 224 is shown in FIG. 36.

When a joystick or other like control means of a bending manipulator 225 is manually operated, a bending angle signal outputted corresponding to a tilt angle of the joystick, i.e., a signal having its voltage value varied dependent on the bending angle, is inputted via an adder 226 to a PID controller 227 which issues a predetermined signal to a PWM generator 228 receiving the source oscillation from the clock signal generator 219. The PWM generator 228 operates to change a pulse width and output the changed pulse width to a driver 229, an output from the driver 229 being applied to the SMA 223a or 223b.

On the other hand, a resistance value detector 230 detects the resistance value of the SMA 223a or 223b in the form of a voltage value and then outputs the detected value to the adder 226 via a sampling/holding circuit 231. The adder 226 determines the difference between the aforesaid bending angle signal and a signal corresponding to the detected resistance value and provided from the sampling/holding circuit 231, and then outputs the determined difference to the PID controller 227 for feedback control. Through this feedback control, the voltage value corresponding to the resistance value of the SMA is controlled to become coincident with the voltage value produced upon manual operation of the bending manipulator 225.

Figure 37:
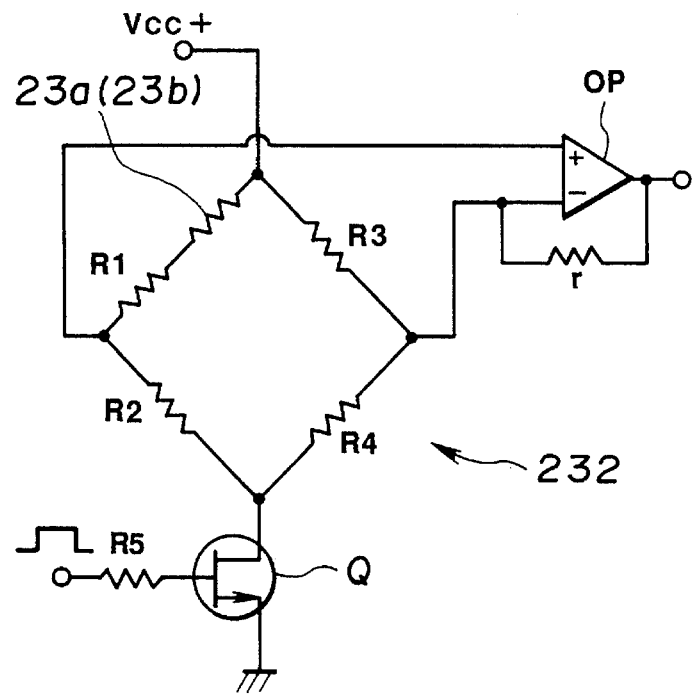

FIG. 37 shows the driver 229 and the resistance value detector 230 in detail.

A negative resistance element R1 and a dummy resistance element R2 are connected to the SMA 223a (or 223b) in series, the dummy resistance element R2 being connected at the other end to a drain of a field effect transistor (FET) Q. Further, resistors R3, R4 are connected to the SMA 223a (or 223b) and the resistance elements R1, R2 in parallel, thereby forming a bridge circuit 232.

Additionally, the output of the PWM generator 228 is applied to a gate of the field effect transistor Q via a resistor R5. On the other hand, a differential amplifier OP has a non-inverted input terminal connected to a junction between the negative resistance element R1 and the dummy resistance element R2, and also an inverted input terminal connected to a junction between the resistors R3 and R4. A resistor r for setting the gain is connected between the inverted input terminal and an output terminal of the differential amplifier OP.

Figure 38:
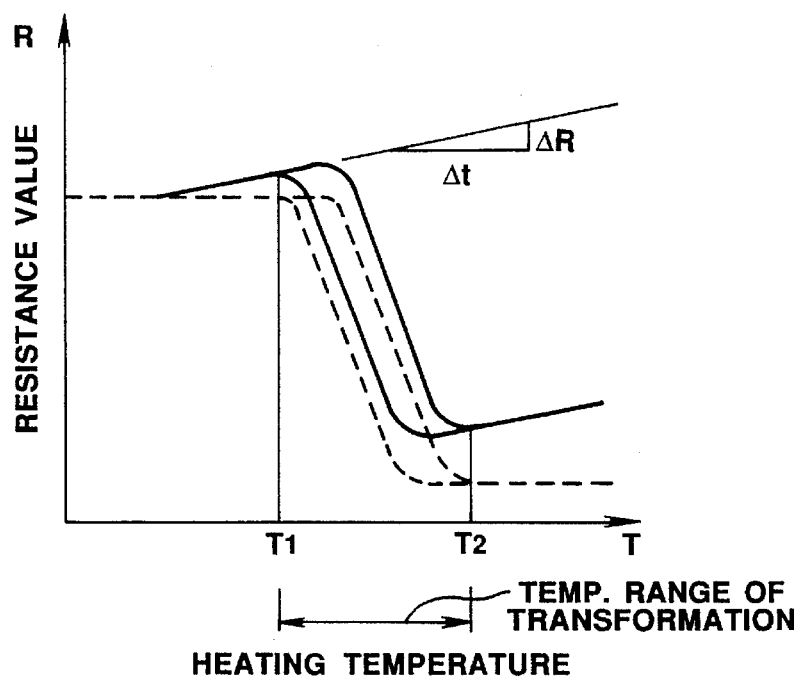

As indicated by solid lines in FIG. 38, the SMA 223a, 223b has a temperature coefficient $\Delta R/\Delta t$ other than a temperature range of transformation from T1 to T2 in which the SMA's structure is changed to vary the length of the bendable portion 213 in the lengthwise (axial) direction thereof. The negative resistance element R1 is selected to have a temperature coefficient of $-\Delta R/\Delta t$, namely, equal to an absolute value of the temperature coefficient $\Delta R/\Delta t$ of the SMA 223a, 223b.

Operation of the ninth embodiment will be described next.

When the solid state image sensor (SID) 215 provided in the distal end portion 212 of the endoscope is driven by the pulses φR, φH and φV generated from the reset and horizontal transfer pulse generator 220a and the vertical transfer pulse generator 220b, the optical image is converted into an electric signal and outputted to the process circuit 222 which produces the video signal.

The source oscillation from the clock signal generator 219 is inputted to the process circuit 222 so that the process circuit 222 creates a horizontal sync signal HD and a vertical sync signal from the source oscillation and then creates a standard video signal from those sync signals and the output signal of the solid state image sensor 215.

On the other hand, when the bendable portion 213 of the endoscope is intended to bend in a desired direction, the bending angle signal is outputted from the bending manipulator 225 to the bending controller 224.

Then, the adder 226 in the bending controller 224 determines a difference signal between the bending angle signal from the bending manipulator 225 and the signal indicating the current bending angle of the bendable portion 213 based on the resistance value of the SMA 223a (223b) which is detected by the resistance value detector 230. Pulses corresponding to the above difference signal are outputted from the PID controller 227 to the PWM generator 228.

The PWM generator 228 modulates the above pulses and outputs the modulated pulses to the driver 229.

As shown in FIG. 37, when the pulses outputted from the PWM generator 228 are applied via the resistor R5 to a gate of the field effect transistor Q in the driver 229, the field effect transistor Q is turned on to conduct the SMA 223a (223b) and the resistors R1, R2 which constitute the bridge circuit 232, thereby gradually heating the SMA 223a (223b).

Upon heating, the SMA 223a (223b) transforms from a condition of coarse-pitch coil as one memorized shape to a condition of dense-pitch coil as another memorized shape, so that the bendable portion 213 having the SMA 223a (223b) built therein is bent in a desired direction.

When the SMA 223a (223b) is heated, the resistance value R of the SMA 223a (223b) is drastically decreased in the temperature range of transformation from T1 to T2 as indicated by a solid line in FIG. 38, but is moderately increased in the other range at a positive temperature coefficient $\Delta R/\Delta t$. Meanwhile, the resistance value of the aforesaid negative resistance element R1 connected to the SMA 223a (223b) in series has the temperature coefficient of $-\Delta R/\Delta t$. As indicated by a broken line in FIG. 38, therefore, the detected resistance value becomes constant independently of the heating temperature T in the temperature range of transformation from T1 to T2.

The voltage in accordance with the resistance value characteristic indicated by the broken line in FIG. 38 is applied to the non-inverted input terminal of the differential amplifier OP which constitutes the resistance value detector 230 and is connected to the output side of the aforesaid bridge circuit, whereas the voltage corresponding to the resistance value of both the SMA 223a (223b) and the negative resistance element R1 under a condition where the bendable portion 213 is in a vertical position, by way of example, is obtained as a reference divided voltage from the junction between the resistors R3 and R4 and then applied to the inverted input terminal of the differential amplifier OP.

As a result, the current bending angle of the bendable portion 213 can be detected on the basis of the voltage outputted from differential amplifier OP. Also, since the output voltage of the differential amplifier OP due to the resistance characteristic of the negative resistance element R1 with respect to the heating temperature when the heating temperature T of the SMA 223a (223b) departs from the temperature range of transformation from T1 to T2, it is possible to easily determine the maximum or minimum bending angle of the bendable portion 213 in the temperature range of transformation from T1 to T2 of the SMA 223a (223b), with the result of improved controllability.

Then, a pulse corresponding to the resistance value, which is obtained by correcting the resistance value of the SMA 223a (223b) with the negative resistance element R1 and detected in the form of the output voltage of the differential amplifier OP, is outputted as the bending angle signal of the bendable portion 213 to the adder 226 via the sampling/holding circuit 231 for feedback control. Through this feedback control, the SMA 223a or 223b can be controlled into states of many different resistance values in the temperature range of transformation from T1 to T2, i.e., states of many different lengths, causing it to set a number of bending angles different from one another.

Figure 39:
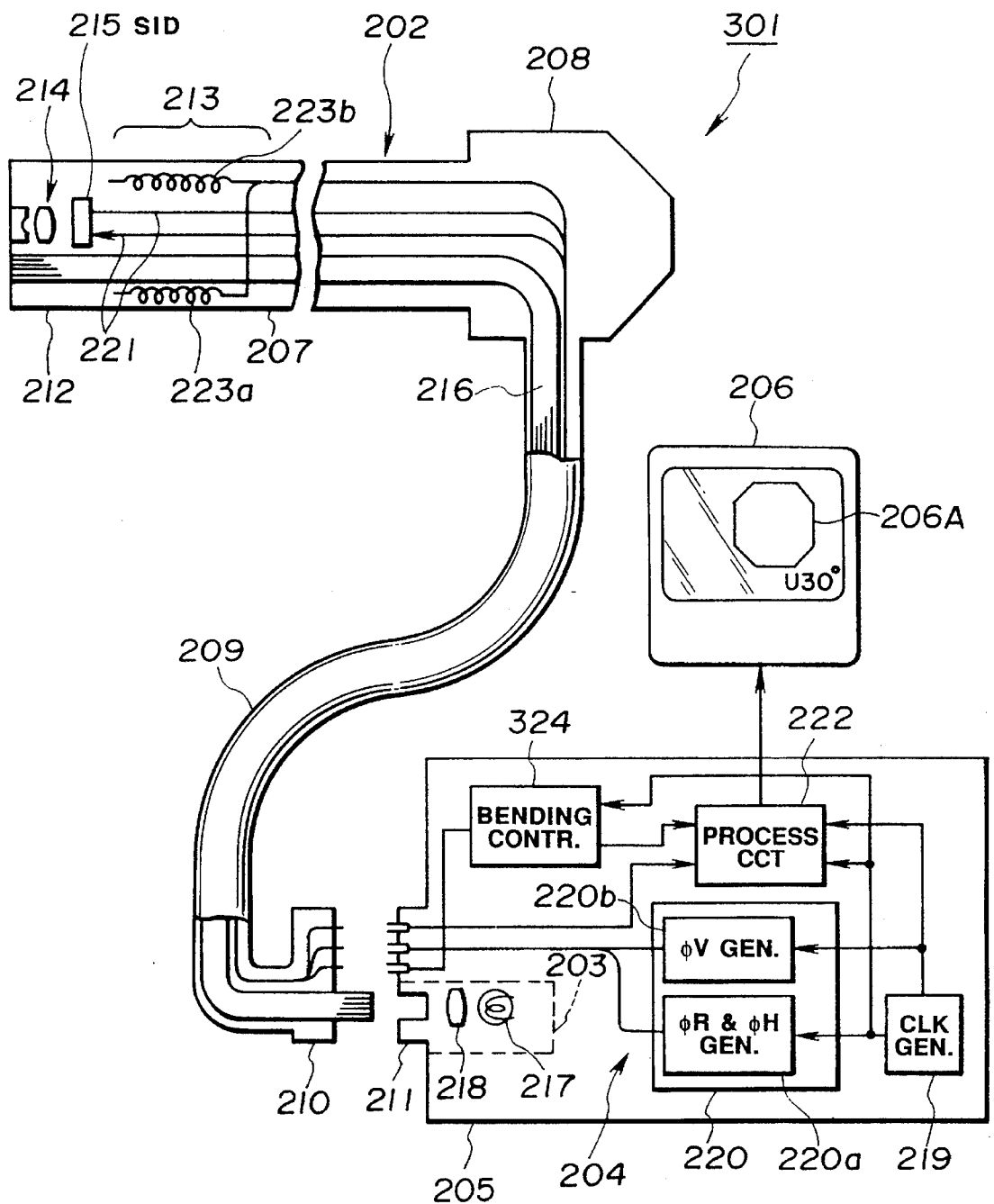
FIG. 39 is a diagram showing the entire configuration of an endoscope device according to a modification of the ninth embodiment.

There will next be described an endoscope device 301 in which bendable means is bent by pulse-controlled energization in synchronism with a sync signal. The endoscope device 301 shown in FIG. 39 is different from the endoscope device 201 in the configuration of a bending controller 324. Since the remaining is identical therebetween, the same components are denoted at the same reference numerals and will not be explained here.

Figure 40:
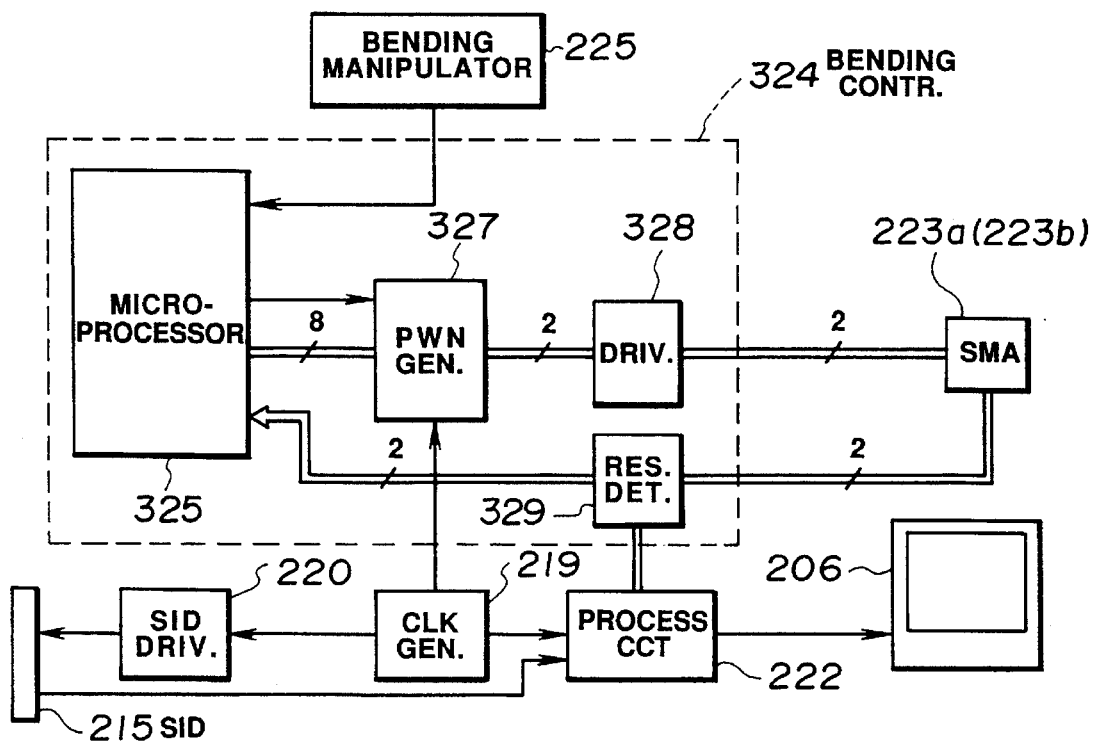
FIG. 40 is a block diagram showing the configuration of a bending controller in the modification.

The configuration of the bending controller 324 is shown in FIG. 40. The bending controller 324 includes a microprocessor 325, as shown in FIG. 40, which receives an analog signal from the bending manipulator 225 and an 8-bit digital signal dependent on the analog signal to a PWM generator 327. Based on a command and the digital control signal from the microprocessor 325, the PWM generator 327 outputs a pulse signal of desired cycle and pulse width.

PWM generator 327 receives the source oscillation from the clock signal generator 219. An output of the PWM generator 327 is applied to the SMA 223a or 223b via an (SMA) driver 328 so that the SMA 223a or 223b is heated. A resistance value detector 329 for detecting the resistance value of the SMA 223a or 223b feeds a detected signal back to the microprocessor 325, whereupon the microprocessor 325 outputs a control signal to the PWM generator 327 dependent on the difference between a manipulation input for bending and the feedback signal, thus making control to provide any desired bending angle corresponding to the manipulation input for bending.

The resistance value detector 329 for detecting the resistance value of the SMA 223a or 223b to determine its bending angle is arranged to, by way of example, measure the resistance value by using the bridge circuit or the like during periods of not supplying the PWM signal, read data of the bending angle by using the resistance value stored in a ROM or the like as an address, and output the bending angle data to the process circuit 222.

The source oscillation from the clock signal generator 219 is inputted to the process circuit 222 so that the process circuit 222 creates a horizontal sync signal HD and a vertical sync signal from the source oscillation. The source oscillation is also inputted to the SID driver 220 which applies a SID drive signal in synchronism with the source oscillation to the SID 215.

Figure 41:
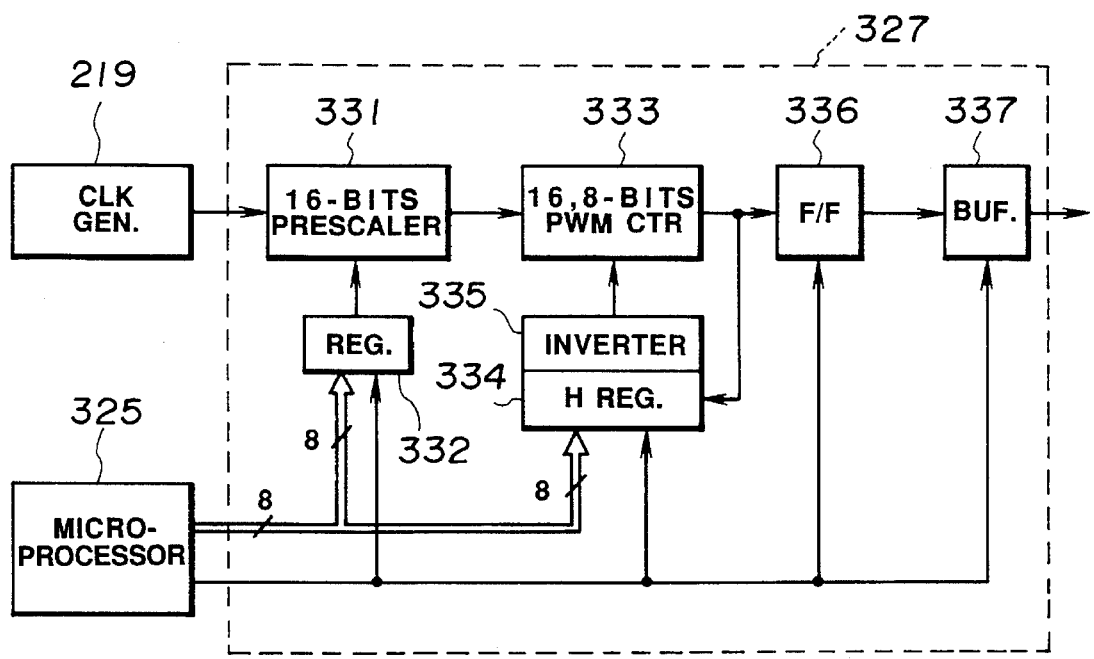
FIG. 41 is a block diagram showing the configuration of a PWM generator.
Figure 42:
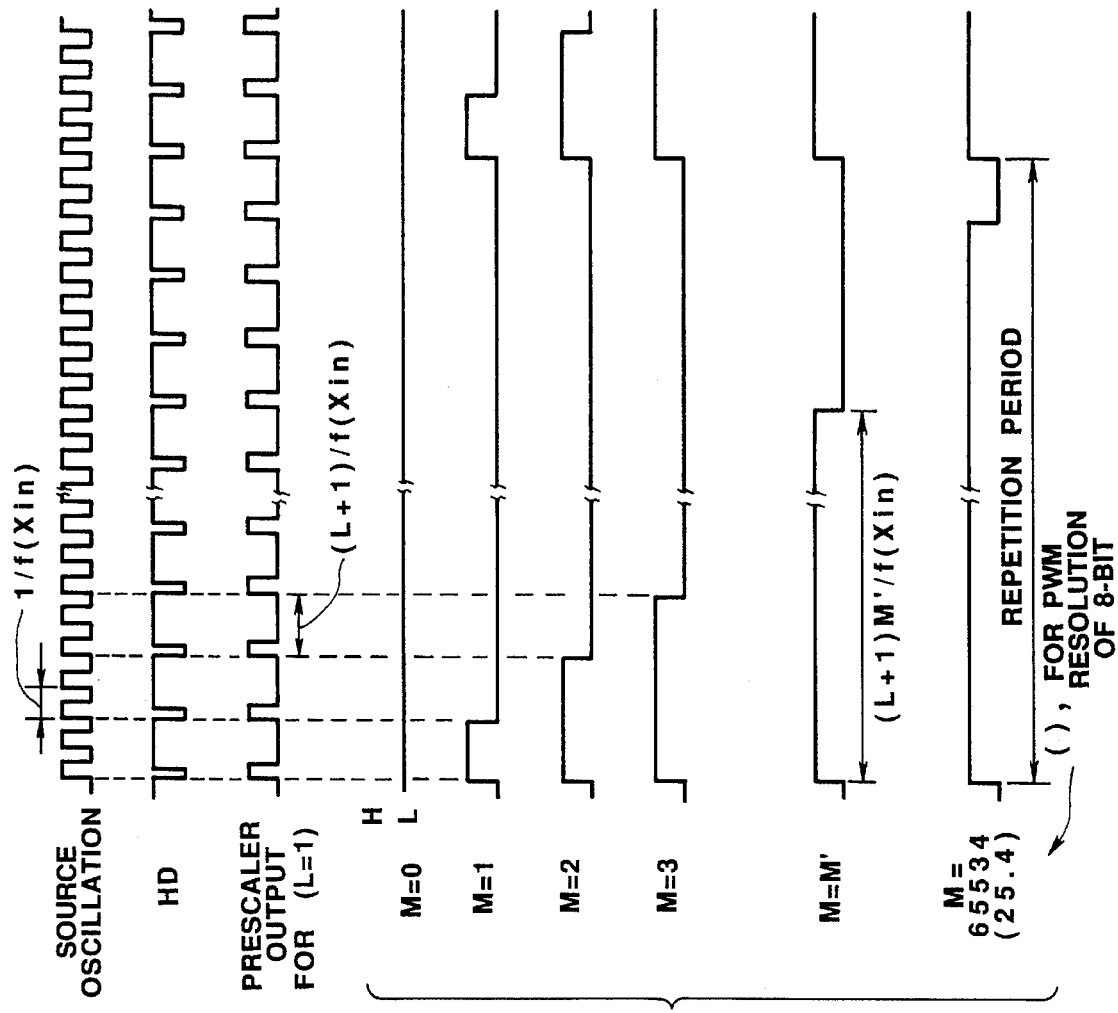
FIGS. 42a–42d are a set of time charts for explaining operation of the PWM generator.

The PWM generator 327 is configured as shown in FIG. 41 and operates as shown in FIG. 42.

The source oscillation from the clock signal generator 219, shown in FIG. 42a, is inputted to a prescaler 331 of 16-bit type, for example, which can divide the frequency with resolution of 16 bits and produces a prescaler output of the cycle inversely proportional to the frequency dividing ratio. The cycle of the prescaler output is determined in accordance with a preset data (parameter data) L which is outputted from the microprocessor 325 to a register 332 of 8-bit type, for example, for the purpose of cycle setting. As a result, the prescaler output of the cycle given by $(L+1)/f(Xin)$, as shown in FIG. 42c, is issued.

The prescaler output is selected such that its cycle is not only integer time the cycle $1/f(Xin)$ of the source oscillation, but also integer time the cycle of the horizontal sync signal HD created from the source oscillation as shown in FIG. 40b. In other words, because the horizontal sync signal HD has the cycle integer time that of the source oscillation, the prescaler output is set to be integer time that of the horizontal sync signal HD. (It should be noticed that the cycle of the prescaler output and the cycle of the horizontal sync signal are set equal to each other in FIG. 42.)

The prescaler output is applied to a PWM counter 333 of 16, 8-bit type, for example. Also applied to the PWM counter 333 is a parameter M, outputted from the microprocessor 325 for setting the pulse width, via an H register 334 and an inverter 335.

Based on the value of the parameter M of 8 bits, for example, PWM signals each having the pulse width of $(L+1)M/(Xin)$ are outputted from the PWM counter 333 via a flip-flop 336 and a buffer 337 as shown in FIG. 42d.

The PWM generator 327 is arranged such that the PWM signals rise and fall in synchronism with blanking pulses of the horizontal sync signal HD shown in FIG. 42b. Here, the (horizontal) blanking period is defined as including one blanking pulse, a front porch on the front edge side thereof and a back porch on the rear edge side thereof. Accordingly, this modification is featured in that the rising edge and the falling edge of each PWM signal are both within the blanking period of the horizontal sync signal.

Operation of this modification will now be described.

The SID 215 is driven by the pulses φR, φH and φV generated from the reset and horizontal transfer pulse generator 220a and the vertical transfer pulse generator 220b in the SID driver 220, whereupon an optical image of the subject is converted into an electric signal and outputted to the process circuit 222 which produces a video signal component. The source oscillation from the clock signal generator 219 is inputted to the process circuit 222 so that the process circuit 222 creates a horizontal sync signal HD and a vertical sync signal from the source oscillation and then creates a standard video signal from those sync signals and a signal resulted from processing the output signal of the SID 215.

On the other hand, the source oscillation from the clock signal generator 219 is also inputted to the PWM generator 327 in the bending controller 324 so that, in synchronism with the blanking pulses of the horizontal sync signal HD, the PWM generator 327 creates the PWM signal of the cycle integer times that of the horizontal sync signal HD.

Depending on the value of the parameter M outputted from the microprocessor 325, any one of the PWM signals shown in FIG. 42d is outputted from the PWM generator 327. More specifically, when the M value is small, the PWM generator outputs the PWM signal having a short pulse width and when the M value is large, it outputs the PWM signal of the long pulse width. The PWM signal thus outputted is supplied to the SMA 223a or 223b for heating and, consequently, the SMA 223a or 223b is controlled by the microprocessor 325 to take the bending angle instructed from the bending manipulator 225.

Since the PWM signal is arranged such that both the rising and falling edges occur within the blanking period of the horizontal sync signal HD for any M value, noises generated at the edges of drive pulses for driving the SMA 223a or 223b also occur within the blanking period of the horizontal sync signal HD. Accordingly, even if those noises mix into the video signal outputted from the process circuit 222, they would not affect the signal portion representative of the endoscope image, resulting in an endoscope image of high quality free from noises.

It will be apparent that although the PWM signal rises and falls within the blanking period of the horizontal sync signal HD in this embodiment, it may rise and fall within the vertical blanking period.

Additionally, the subject sensed by the SID 215 is displayed in an endoscope image display area 206A occupying part of the monitor screen of the monitor 206 in many cases as shown in FIG. 39, by way of example. In such a case, it is also conceivable to control the rising and falling edges for the drive pulses so as to locate within any period of the video signal other than the endoscope image display area 206A. Moreover, when displaying character data for indication of the bending angle and so forth at the same time, the drive pulses may be controlled such that their edges locate in the period except for the display area of those character data. As an alternative, since character data or the like are generally in the form of binary signals and are less affected by noises than is the video signal, the control may be performed without taking into consideration the period corresponding to the display area of those character data.

Furthermore, the edges of the drive pulses may be controlled to locate within any period excluding the period in which the signal actually read out from the SID 215 is present.

With this modification, in a combination of the endoscope having the image sensing means to produce the video signal and the bending mechanism for driving the SMA in the PWM method to bend it, the PWM signal is synchronized with the horizontal or vertical sync signal of the video signal and the edges of the PWM signal are controlled to locate within the blanking period of the sync signal, by way of example. Therefore, the noises generated at the edges of the PWM signal can be prevented from appearing in the image displayed on the monitor screen, making it possible to provide the image of high quality.

A catheter device as a probe device in which insulation means for securing safety is formed in the driver system of the bending actuator mechanism will be described below.

Figure 43:
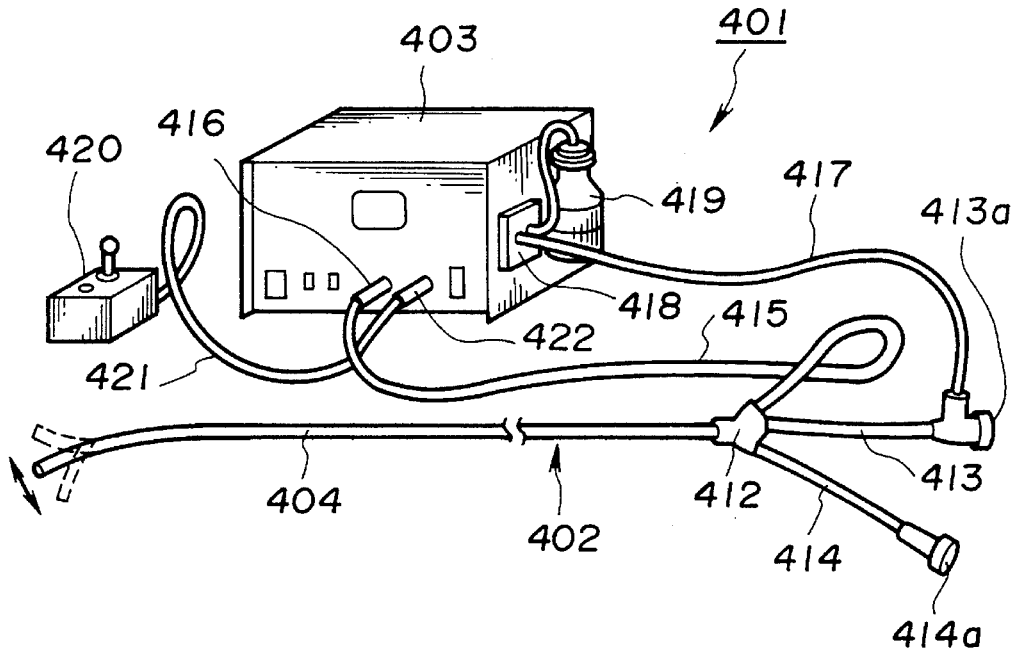
Figure 44:
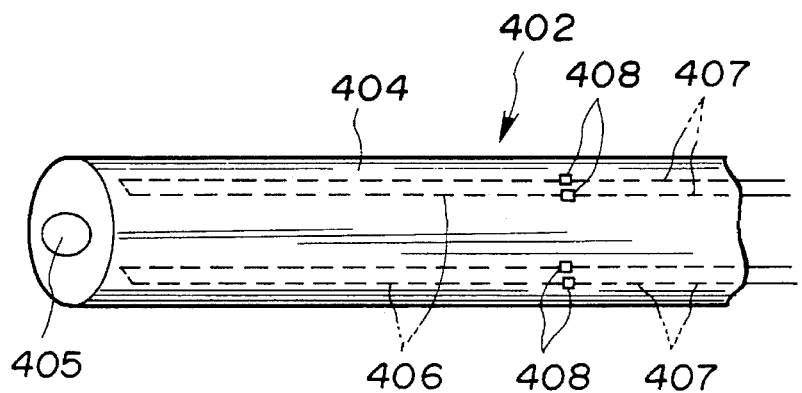

As shown in FIG. 43, a catheter device 401 according to a tenth embodiment of the present invention is constituted by connecting a bendable catheter 402 to a drive unit 403. An insert 404 of the catheter 402 comprises a flexible multi-lumen tube which is provided with a channel 405 defined for such purposes as inserting a thin scope, guide wire or the like, or delivering and sucking a solution therethrough, as shown in FIG. 44.

The insert 404 has a plurality of passages (lumens) for housing shape memory alloys therein, and two shape memory alloy wires (hereinafter referred to as SMA wires) 406 are disposed as bending actuators in those lumens, each of the SMA wires 406 being bent at the distal end side into a U-shape for turn-back. Both of the ends of the SMA wire 406 are connected at caulking portions 408 to lead wires 407 in turn connected to the drive unit 403 for supplying electric power. The distal end portion of the insert 404 is bent in a desired direction as indicated by the arrow by selectively supplying the electric power to the two SMA wires 406 to heat them for contraction.

Figure 45:
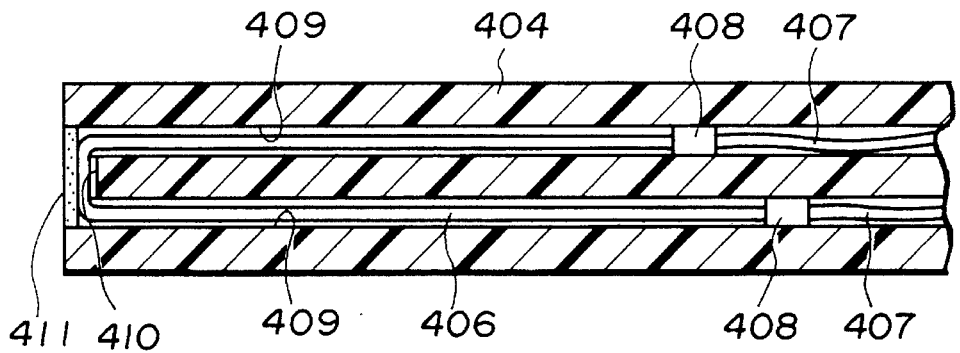

To put it in more detail, as shown in FIG. 45, the SMA wire 406 is turned back at the distal end side for insertion through two SMA wire housing lumens 409 in opposite directions. The distal end portion of the SMA wire 406 is arranged to pass through a groove 410 provided to extend between the two lumens 409, and the groove 410 is filled with a filler 411 for sealing off in such a manner as to fix the distal end portion of the SMA wire 406 in place and prevent it from being exposed to the exterior. Then, the SMA wire 406 is fixedly connected at the rear end side by the caulking portions 408 to the lead wires 407 for supplying the electric power therethrough. Axial contraction and extension of the SMA wire 406, disposed at a position offset from the central axis of the insert 404, permits the insert 404 to be bent as desired.

The SMA wire 406 can be formed of any suitable materials such as a Ti-Ni alloy or a Cu-Zn-Al alloy. Above all, the Ti-Ni alloy is more preferable.

The catheter 402 is branched at a branch portion 412 positioned closer to the drive until 403 into three parts; i.e., a near-side tube 413, a near-side tube 414 and a power supply cable 415. The power supply cable 415 is connected to a power supply connector 416 provided on the drive unit 403 so that the electric power for heating is supplied from the drive unit 403 to the SMA wire 406 in the catheter 402 via the power supply cable 415.

The two near-side tubes 413 and 414 are both communicated with the channel 405 of the insert 404, allowing a guide wire, fiberscope or the like to be inserted from respective mouthpieces 413a, 414a to extend up to the distal end of the insert 404 therethrough.

Further, the near-side tube 413 is provided with a water feed tube 417 extending laterally from beside the mouthpiece 413a and formed of silicon or the like. Cooling water can be supplied from the drive unit 403 through the water feed tube 417 for lowering the surface temperature of the SMA wire 406 and the catheter 402. To this end, though not shown, an elastic member or the like is provided inside the mouthpiece 413a to provide the water-tight structure which can prevent the cooling water from leaking through the mouthpiece 413a even under a condition where a fiberscope or the like is inserted. When no fiberscope or the like is inserted through the near-side tube 413, a cap is fitted over the mouthpiece 413a to keep the water-tight condition.

The water feed tube 417 is connected to a flat type pump 418 provided on the lateral surface of the drive unit 403, and a bottle 419 containing a physiological saline solution therein for cooling is connected to the pump 418. The pump 418 intermittently squeezes the water feed tube 417 to push the physiological saline solution out of the bottle 419 so that the solution is supplied as cooling water from the pump 418 through the near-side tube 413 and then into the catheter 402. As a result, the SMA wire 406 heated by being supplied with the electric power is effectively cooled.

Also connected to the drive unit 403 is a manipulation input circuit 420, comprising a joystick or the like to instruct bending operation of the distal end portion of the catheter 402, via a signal cable 421 and a connector 422. Notice that the manipulation input circuit 420 may also be constituted by a track ball, mouse, button switch, slide switch or the like other than the joystick.

Figure 46:
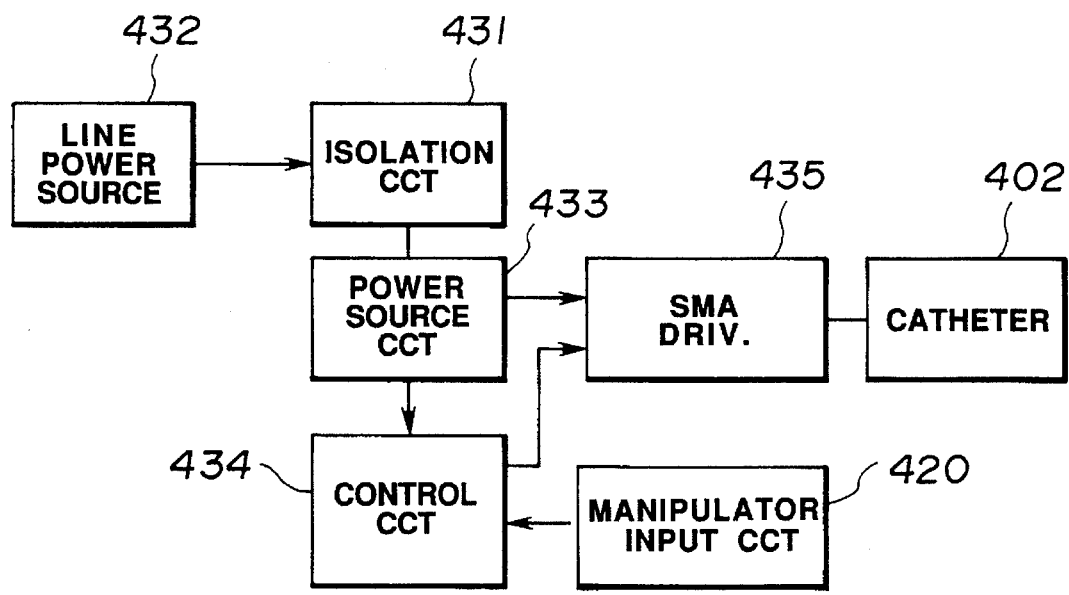

The configuration of the drive unit 403 will be next explained with reference to FIGS. 46 and 47.

The drive unit 403 includes an isolation circuit 431 comprising an isolation transformer or the like, and an external line power source 432 is directly connected to the primary side of the isolation circuit 431. The secondary side of the isolation circuit 431 is connected to a power source circuit 433 for supplying the driving electric power to the SMA wire 406, so that the electric power from the line power source 432 is supplied to the power source circuit 433 via the isolation circuit 431.

Here, the primary side of the isolation circuit 431 (i.e., the same side of the isolation circuit 431 as the line power source 432) will be referred to as a primary circuit, and the secondary side thereof (i.e., the same side of thereof as the power source circuit 433) will be referred to as a secondary circuit. The power source circuit 433 is connected to a control circuit 434 for controlling the amount of electric power supplied to the SMA wire 406, and also to an SMA driver 435 for supplying the electric power to the SMA wire 406 for heating. The power source circuit 433 comprises a switching regulator and so forth and converts an AC voltage of 100 V from the line power source 433 into a DC voltage of +15 V, followed by supplying the DC voltage to both the control circuit 434 and the SMA driver 435.

The manipulation input circuit 420 is connected to the control circuit 434 which supplies the electric power to the SMA driver 435 in accordance with an instruction from the manipulation input circuit 420. The SMA driver 435 supplies the power supply to the SMA wire 406 for heating based on the output of the control circuit 434, whereupon the SMA wire 406 is contracted under supply of the electric power and hence heating.

As shown in FIG. 47, the control circuit 434 includes a triangular wave generator 436, and a triangular wave signal produced from the generator 436 is supplied to a negative input terminal of a comparator 437. It should be understood that since two SMA wires 406 are here disposed in the catheter 402, two lines of the identical circuits are provided in this embodiment.

Meanwhile, a predetermined voltage instructed from the joystick 420a is supplied to a positive input terminal of the comparator 437. The comparator 437 compares the above triangular wave signal and the voltage applied to the positive input terminal to thereby produce a pulse width modulation (PWM) signal. An output of the comparator 437 is branched into twos, one of which is applied to one input terminal of an AND circuit 439 via a monostable multivibrator 438 and the other of which is directly applied to the other input terminal of the AND circuit 439.

The monostable multivibrator 438 and the AND circuit 439 serve to set a maximum duty ratio for the PWM signal outputted from the comparator 437. In the case of such a flexible tube that a single SMA wire 406 is disposed in the catheter 402 to make the flexible tube bendable in one direction, by way of example, the catheter can be formed to be small in its diameter and, therefore, the heat produced by the SMA wire 406 is likely to be held. For this reason, the maximum duty ratio of the output from the comparator 437 is set to 0.13.

Further, in the case of such a flexible tube that two SMA wires 406 are disposed in the catheter 402 to make the flexible tube bendable in two directions as shown in FIG. 44, the catheter is increased in its diameter as compared with the case of using a single SMA wire and, therefore, the heat produced by the SMA wires 406 is less likely to be held. For this reason, the maximum duty ratio of the output from the comparator 437 is set to 0.15. In this way, the maximum duty ratio of the signal supplied to the SMA wire 406 is set to 0.13–0.15 dependent on the catheter diameter. If only the output of the monostable multivibrator 438 is used in the above process, the maximum duty ratio may exceed the setting value due to variations. Accordingly, the AND circuit 439 is provided to set a maximum value by using an output therefrom.

An output terminal of the AND circuit 439 is connected to the SMA driver 435. The SMA driver 435 comprises a resistor 440, an FET 441 and an isolation transformer 442. The output of the AND circuit 439 is applied to a gate terminal of the FET 441 via the resistor 440. The DC voltage of +15 V is supplied to a source terminal of the FET 441 via the primary side of the isolation transformer 442, and a drain terminal of the FET 441 is grounded.

The secondary side of the isolation transformer 442 is connected to the SMA wire 406 in the catheter 402 via the power supply cable 415 and the power supply lead wires 407.

In other words, the PWM signal outputted from the control circuit 434 is subjected to power amplification in the SMA driver 435 and then supplied to the SMA wire 406 for heating. In this connection, the power source circuit 433 which belongs to the secondary circuit and part of the circuit in the catheter 402 (hereinafter referred to as a patient circuit) are electrically separated from each other by the isolation transformer 442 in the SMA driver 435.

Figure 48:
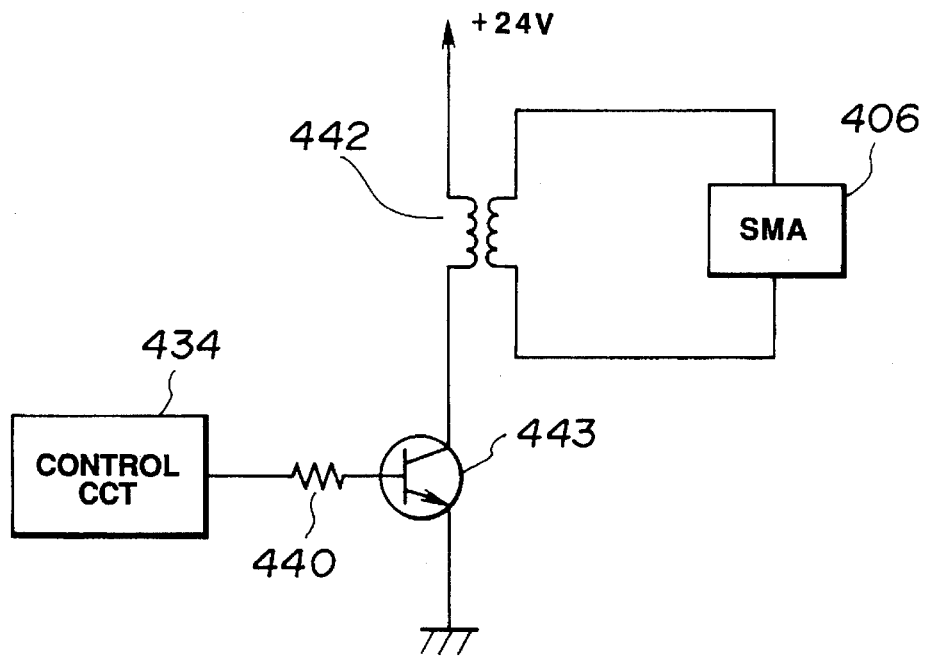

Notice that the SMA driver 435 may comprise a transistor 443, as shown in FIG. 48, in place of the FET 441. In this case, although the DC voltage to be supplied is changed to +24 V, the remaining is constituted in the same manner as the above. Alternatively, other switching elements such as a relay or photo-MOS relay may also be used to constitute the SMA driver 435.

Operation of the catheter device 401 thus constructed will now be described.

The insert 404 of the catheter 402 is inserted to a body cavity or the like to make observation and treatment at an objective location. On this occasion, by manually operating the manipulation input circuit 420, the SMA wires 406 in the catheter 402 are selectively supplied with electric power for contraction under heating so that the distal end side of the insert 404 is bent as desired.

In response to an instruction from the manipulation input circuit 420, the SMA driver 435 outputs the PWM signal and supplies it to the desired SMA wire 406. The SMA wire 406 is contracted in the axial direction under heating by being supplied with the electric power. Because the SMA wire 406 is disposed at a position offset from the central axis of the insert 404 and is fixed at its both ends in the insert 404, the distal end portion of the catheter 402 is pulled toward the operator side upon contraction of the SMA wire 406, thereby bending the distal end side of the insert 404.

In this embodiment, the manipulation input circuit 420 issues the on/off instruction for controlling whether or not to supply the electric power to the SMA wire 406. However, it is also possible to set the voltage outputted from the manipulation input circuit 420 variable, and change the duty ratio of the PWM signal for controlling the amount of electric power supplied to the SMA wire 406.

When reducing the bending angle of the insert 404, the pump 418 associated with the drive unit 403 is operated to supply the cooling water from the bottle 419 into the catheter 402 via the water feed tube 417 and the near-side tube 413. As a result, the SMA wire 406 is cooled for extension and the insert 404 is bent in the direction of returning to the original straight condition.

As mentioned before, the patient circuit in the catheter 402, including the SMA wires 406, is electrically separated from the power source circuit 433, the control circuit 344 and the SMA driver 435, all of which belong to the secondary circuit, by the isolation transformer 442 in the SMA driver 435. Therefore, even if there occurs any abnormality such as a short circuit in the control circuit 434, the SMA driver 435, etc., a large current will not flow into the patient circuit.

Consequently, even if any abnormality is caused in the secondary circuit of the drive unit 403, it is possible to prevent a large current from flowing into the patient circuit in the catheter 402, such as the SMA wires 406, and thus prevent such a drawback that the operator or the patient will receive an electric shock.

There will be described below an eleventh embodiment of the present invention in which shape memory alloy wires are arranged as bending actuators inside a small-diameter insert of an endoscope.

Figure 49:
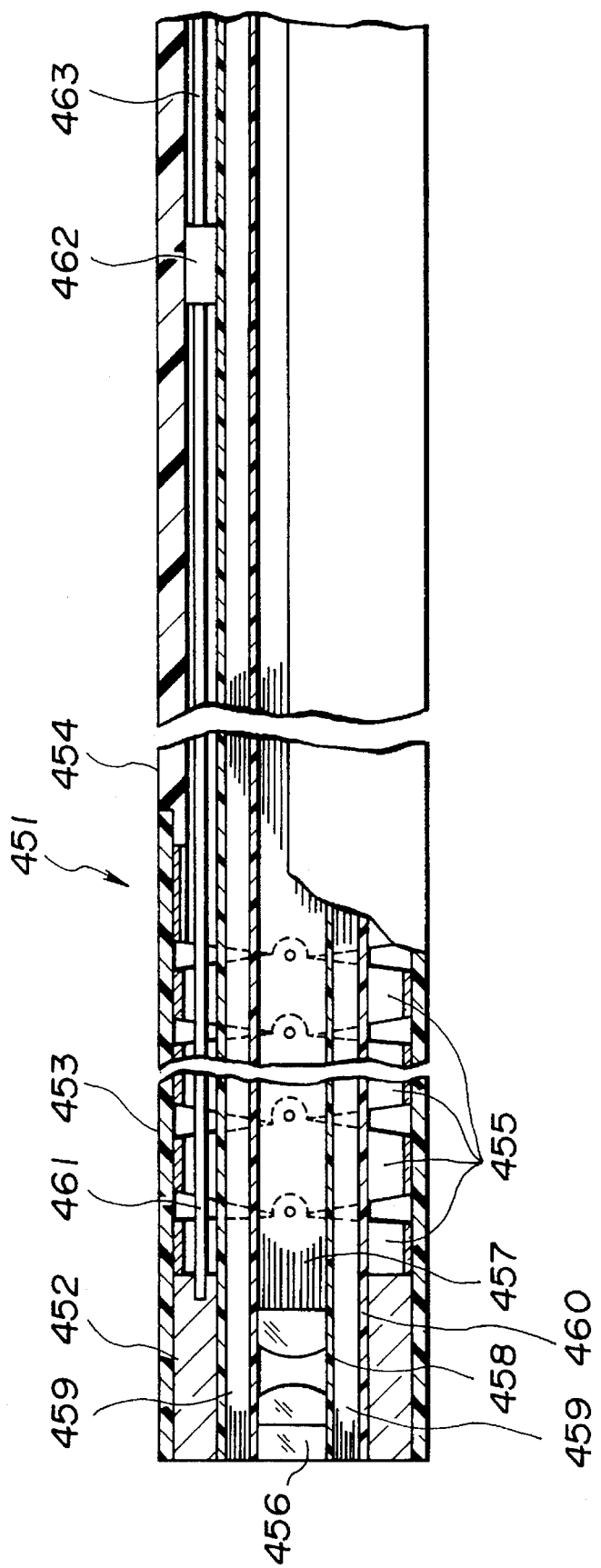

As shown in FIG. 49, the endoscope used in this embodiment is constituted by a small-diameter fiber scope. An insert 451 of the endoscope comprises a hard distal end portion 452, a bendable portion 453 provided to continuously extend from the rear end of the distal end portion 452 and having a plurality of bending pieces 455 and a flexible tube portion 454 provided to continuously extend from the rear end of the bendable portion 453, these portions being disposed in this order from the distal end side. The distal end portion 452 includes an object optical system 456 for focusing an image of a subject, and the front end face of an image guide fiber 457 is arranged at the focus position of the object optical system 456.

The image guide fiber 457 is inserted through the insert 451 and has its rear end extending up to an eyepiece portion (not shown). The object optical system 456 and the image guide fiber 457 are covered with a protective tube 458, and light guide fibers 459 are provided outside the protective tube 458. The outer circumference of the light guide fibers 459 are also covered with a protective tube 460. The light guide fibers 459 are extended through the insert 451 and connected to a light source unit (not shown) so that a ray of illumination light from the light source unit passes through the optical guide fibers 459 and is irradiated from the distal end face of the insert 451.

SMA wires 461 covered with respective tubes are disposed in the insert 451 and have their distal ends fixed in the distal end portion 452. Each of the SMA wires 461 is extended through the insert 451 and fixed at the distal end side by a caulking portion 462. The caulking portion 462 serves to interconnect the SMA wire 461 and a power supply lead wire 463, which is in turn connected to a bending drive unit, for supplying the electric power to the SMA wire 461 for heating.

It is to be noted that in place of using the SMA wire 461 covered with the tube, an SMA lumen formed of a silicon tube may be provided in the insert 451 and a wire-like shape memory alloy may be arranged to extend through the lumen.

Figure 50:
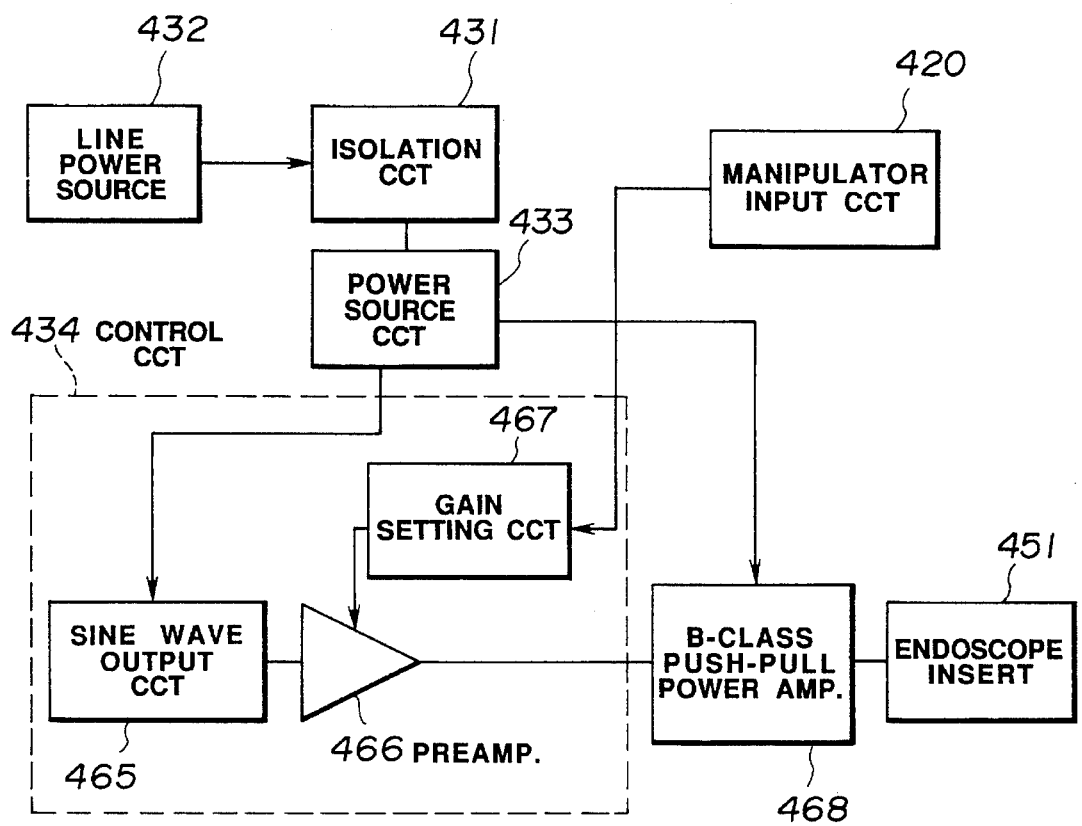

The bending drive unit for supplying the electric power to the SMA wire 461 for heating is constituted as shown in FIG. 50.

The control circuit 434 includes a sine wave generator 465 producing a sine wave signal which is inputted to a preamplifier 466. A gain setting circuit 467 for setting an amplification degree in response to an instruction from the manipulation input circuit 420 is connected to the preamplifier 466 and amplifies the sine wave signal with the set amplification degree, followed by supplying the amplified signal to a B-class push-pull power amplifier 468 which serves as a shape memory alloy driver. The B-class push-pull power amplifier 468 amplifies power of the input sine wave signal and supplies the electric power to the SMA wires 461 in the endoscope insert 451 so that the SMA wires 461 are heated for contraction.

The remaining is constituted in the same manner as the tenth embodiment.

Figure 51:
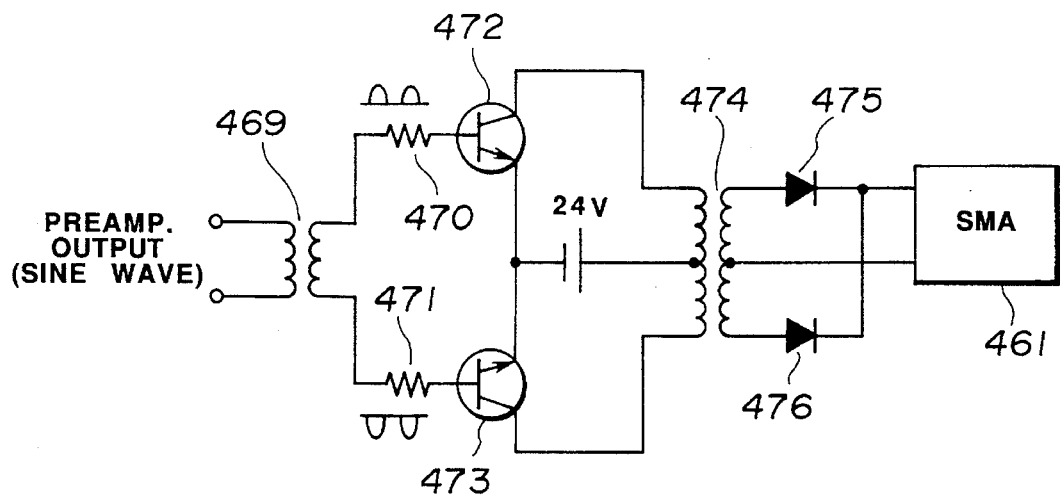

As shown in FIG. 51, the B-class push-pull power amplifier 468 includes a transformer 469 on the input side to which an output signal from the preamplifier 466 is applied. The input sine wave signal is divided into positive half waves and negative half waves which are supplied to bases of transistors 472, 473 via resistors 470, 471, respectively. Collectors of the transistors 472, 473 are connected to the primary side of an isolation transformer 474, and a DC voltage of +24 V is supplied between emitters of the transistors 472, 473 and a center tap of the isolation transformer 474 on the primary side. Both terminals of the isolation transformer 474 on the secondary side are connected to one end of the SMA wire 461 in the endoscope insert 451 via diodes 475, 476 and the power supply lead wire 463, whereas the other end of the SMA wire 461 is connected to a center tap of the isolation transformer 474 on the secondary side.

Stated in other words, the sine wave signal outputted from a preamplifier 466 is amplified in its power by the B-class push-pull power amplifier 468 and then supplied to the SMA wire 461 for heating. In this power supply system, however, the power source circuit 433 as the secondary circuit and the patient circuit including the SMA wire 461 in the endoscope insert 451 are electrically separated from each other by the isolation transformer 474 in the B-class push-pull power amplifier 468.

As with the tenth embodiment, the endoscope insert 451 is inserted to a body cavity or the like to make observation and treatment at an objective location. On this occasion, by manually operating the manipulation input circuit 420, the SMA wires 461 in the endoscope insert 451 are selectively supplied with electric power for contraction under heating so that the bendable portion 443 is bent as desired.

In response to an instruction from the manipulation input circuit 420, the amplification degree of the preamplifier 466 is set by the gain setting circuit 467. Specifically, the sine wave signal from the sine wave generator 465 is amplified by the preamplifier 466 and, at this time, the amplitude of the sine wave signal outputted from the preamplifier 466 is changed in accordance with the value set by the gain setting circuit 467. The amount of electric power supplied to the SMA wire 461 is thereby controlled so as to change the bent condition of the bendable portion 453. The output signal from the preamplifier 466 is amplified in its power by the B-class push-pull power amplifier 468 and then supplied to the SMA wire 461. The SMA wire 461 is contracted in the axial direction under heating by being supplied with the electric power. Because the SMA wire 461 is disposed outside the light guide fibers 459 in the endoscope insert 451 and is fixed at both ends in the endoscope insert 451, the distal end portion 452 is pulled toward the operator side upon contraction of the MA wire 461, thereby turning the bending pieces 455 to bend the bendable portion 453.

As mentioned before, the patient circuit in the endoscope insert 451, including the SMA wires 461, is electrically separated from the power source circuit 433, the control circuit 344 and the B-class push-pull power amplifier 468, all of which belong to the secondary circuit, by the isolation transformer 474 in the B-class push-pull power amplifier 468. Therefore, even if there occurs any abnormality such as a short circuit in the control circuit 434, the B-class push-pull power amplifier 468, etc., a large current will not flow into the patient circuit.

Consequently, even if any abnormality is caused in the secondary circuit of the bending drive unit, it is possible to prevent a large current from flowing into the patient circuit in the endoscope insert 451, such as the SMA wires 461, and thus prevent such a possible danger that the operator or the patient will receive an electric shock, as with the tenth embodiment.

With the tenth and eleventh embodiments, as explained above, since the electric power is supplied to shape memory alloys without directly connecting an electric circuit in the flexible tube portion, including the shape memory alloys, and a shape memory alloy driver to each other, there can be resulted an advantage of enabling to prevent such a possible danger that the operator or the patient will receive an electric shock upon the occurrence of any abnormality in the driver, etc.

FIG. 52 shows the structure of a flexible tube for use in a probe device according to a twelfth embodiment of the present invention. This embodiment is intended to permit bending in four directions, i.e., up and down as well as left and right, by using three angle wires and three SMA wires. Of an endoscope 601 provided with a bending mechanism for a flexible tube according to this embodiment, FIG. 52 schematically shows the construction of part of the endoscope 601, i.e., a bendable portion 602 thereof to which a distal end portion 604 is attached.

As shown in FIG. 52, an object lens 606, an illumination lens 608 and a forceps channel 610 are disposed in the distal end portion 604 provided in the distal end side of the bendable portion 602. The bendable portion 602 comprises a plurality of bending pieces 612 coupled to each other. First to third cylindrical wire receivers 620, 622, 624 (see FIGS. 54a and 54b), which can respectively hold first to third angle wires 614, 616, 618 (described later) therein, are attached by brazing, for example, onto the inner circumferential surface of the bending piece 612 at such positions as dividing the inner circumference into equal three parts.

Figure 53A:
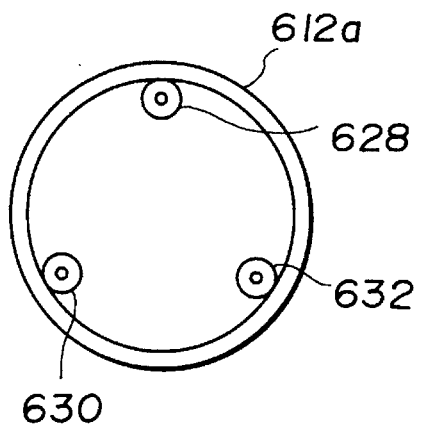
FIG. 53a is a front view showing a piece at the foremost end in FIG. 52.
Figure 53B:
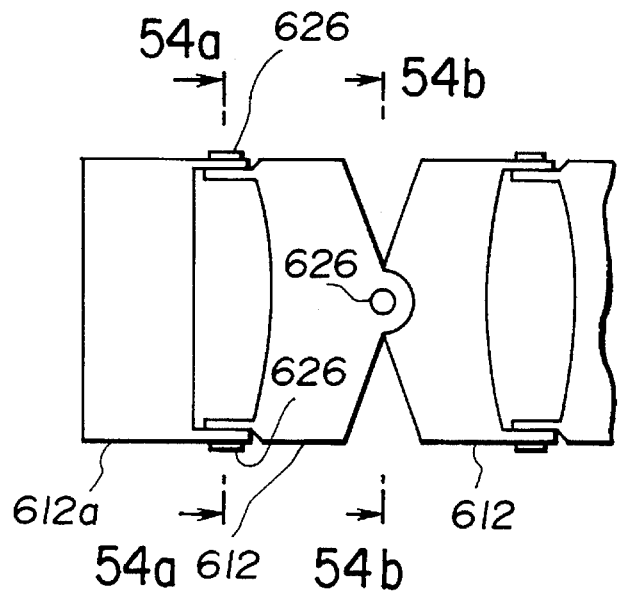
FIG. 53b is a view showing a joint condition between the piece at the foremost end and a next piece adjacent thereto.
Figure 54A:
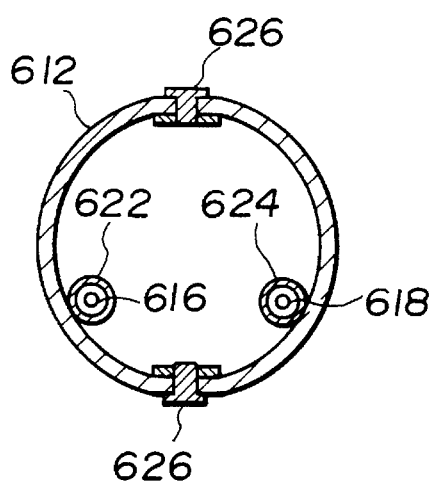
FIGS. 54a and 54b are sectional views taken along the lines 54a—54a and 54b—54b in FIG. 53b, respectively.
Figure 54B:
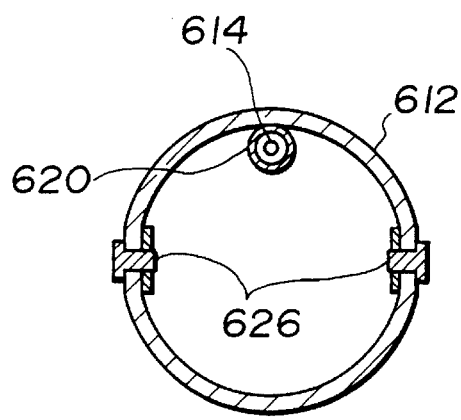

More specifically, as regards to a pair of bending pieces 612 provided on the side near the distal end portion 604, by way of example, a cross-section taken along the line 54a—54a in FIG. 53b is shown in FIG. 54a and a cross-section taken along the line 54b—54b in FIG. 53b is shown in FIG. 54b. The bending piece 612 at a location shown in FIG. 54a (i.e., the bending piece coupled to the foremost bending piece 612a adjacent the distal end portion 604) is provided on the inner circumferential surface thereof with the second and third wire receivers 622, 624 through which the second and third angle wires 616, 618 can be inserted, respectively. Further, the bending piece 612 at a location shown in FIG. 54b (i.e., the bending piece coupled to the bending piece 612 shown in FIG. 54a) is provided on the inner circumferential surface thereof with the first wire receiver 620 through which the first angle wire 614 can be inserted. Such a combination is repeatedly installed for every adjacent twos of the plural bending pieces 612.

The bending pieces 612 are coupled between adjacent twos by a pair of rivets 626 in a rotatable manner. More specifically, as shown in FIG. 54a, the bending piece 612 adjacent the foremost bending piece 612a is provided with the pair of rivets 626 on the symmetrical axis with respect to the second and third wire receivers 622, 624, so that it is coupled by the pair of rivets 626 to the foremost bending piece 612a rotatably (e.g., in the directions to the left and right on the drawing). Further, the bending piece 612 shown in FIG. 54b is provided with the pair of rivets 626 positioned on a line perpendicular to the line connecting between the pair of rivets 626 which are provided on the bending piece 612 shown in FIG. 54a, so that it is coupled by the pair of rivets 626 to the bending piece 612 shown in FIG. 54a rotatably (e.g., in the directions up and down on the drawing). Such a combination is repeatedly installed for every adjacent twos of the plural bending pieces 612.

Moreover, as shown in FIG. 53a, onto the inner circumferential surface of the foremost bending piece 612a at such positions as dividing the inner circumference into equal three parts, there are attached by brazing, for example, first to third fixing portions 628, 630, 632, which can respectively fix the first to third angle wires 614, 616, 618 (see FIG. 52) in places. Thus, the distal ends of the first to third angle wires 614, 616, 618 extending through the first to third wire receivers 620, 622, 624 in the plurality of bending pieces 612 are fixed to the first to third fixing portions 628, 630, 632, respectively.

In addition, as shown in FIG. 52, first to third SMA wires 658, 660, 662 are provided as actuators for respectively tracting the first to third angle wires 614, 616, 618. Each of those SMA wires 658, 660, 662 are formed of a two-directional SMA such as a Ni-Ti alloy and has such characteristics that its length is contracted when heated to above the transforming point thereof, and extended to restore the original length when cooled down below the transforming point. First to third voltage control circuits 664, 666, 668 are provided as drivers for extending or contracting the first to third SMA wires 658, 660, 662, respectively (see FIG. 56).

As shown in FIG. 52, the first to third angle wires 614, 616, 618 are fixedly connected to the distal ends of the first to third SMA wires 658, 660, 662 via first to third connectors 670, 672, 674 disposed in a pliable portion 603, respectively. The rear ends of the first to third SMA wires 658, 660, 662 are each connected to corresponding one of the first to third lead wires 682, 684, 686 via fourth to sixth connectors 676, 678, 680 fixedly disposed in the pliable portion 603. Moreover, fourth to sixth lead wires 688, 690, 692 are connected to the first to third connectors 670, 672, 674, respectively.

Figure 56:
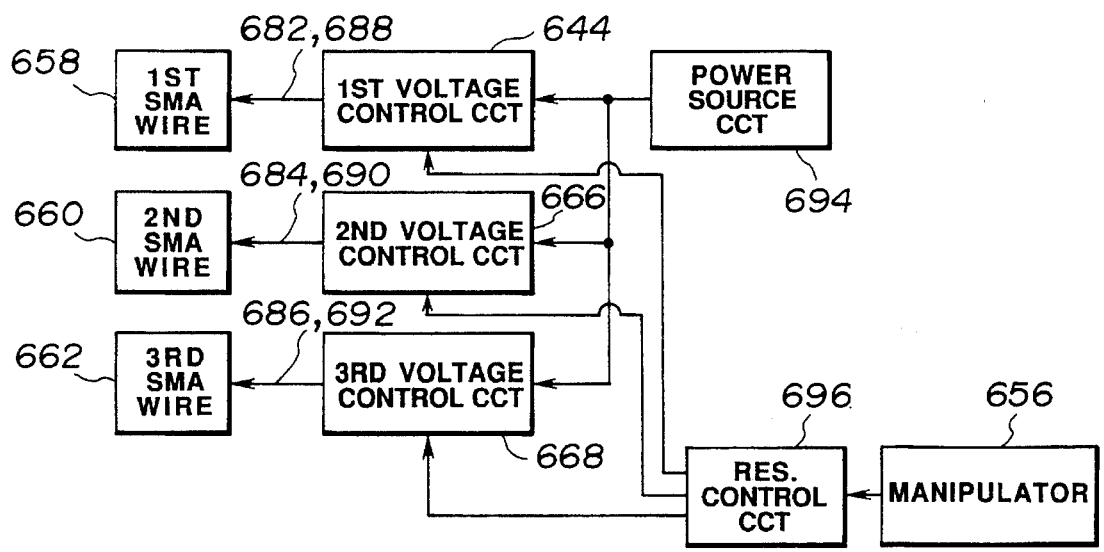

In addition, as shown in FIGS. 52 and 56, the first and fourth lead wires 682, 688 are electrically connected to the first voltage control circuit 664, the second and fifth lead wires 684, 690 are electrically connected to the second voltage control circuit 666, and further the third and sixth lead wires 686, 692 are electrically connected to the third voltage control circuit 668. A power source circuit 694 and a resistance control circuit 696 are both electrically connected to each of the first to third voltage control circuits 664, 666, 668. The resistance control circuit 696 is arranged such that in response to a manipulation signal transmitted from a manipulator 656 such as a joystick, it can selectively control the amount of voltage supplied to the first to third voltage control circuits 664, 666, 668.

Figure 55:
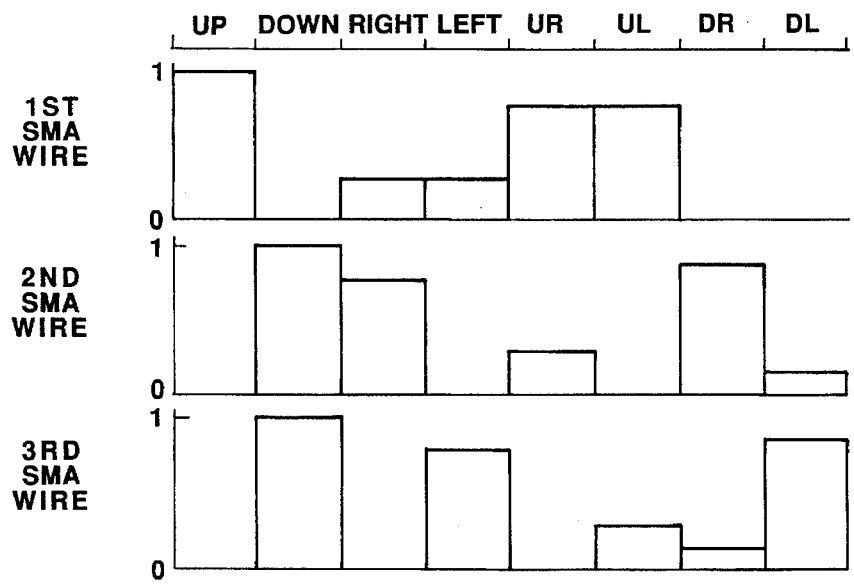

Operation of the bending mechanism of the flexible tube according to this embodiment will now be next explained with reference to FIGS. 55 and 56.

When bending the bendable portion 602 in the downward (DOWN) direction, the resistance control circuit 696 is driven through the manipulator 656. Then, the first voltage control circuit 664 is controlled to cut off the electric power supplied to the first SMA wires 658 (i.e., cut off the voltage applied to the first SMA wire 658 via the first and fourth lead wires 682, 688), whereas the second and third voltage control circuits 666, 668 are controlled such that a voltage is applied with the same value from the power source circuit 694 to the second and third SMA wires 660, 662. The second and third SMA wires 660, 662 are thereby heated for contraction of their length. As a result, the second and third angle wires 616, 618 are pulled evenly so as to bend the bendable portion 602 in the downward direction.

When bending the bendable portion 602 in the rightward (RIGHT) direction, the third voltage control circuit 664 is controlled through the resistance control circuit 696 to cut off the electric power supplied to the third SMA wire 658, whereas the first and second voltage control circuits 664, 666 are controlled such that a voltage is applied with the same value from the power source circuit 694 to the first and second SMA wires 658, 660. The first and second SMA wires 658, 660 are thereby heated for contraction of their length. As a result, the first and second angle wires 614, 616 are pulled evenly so as to bend the bendable portion 602 in the downward direction.

When bending the bendable portion 602 in the leftward (LEFT) direction, the second voltage control circuit 666 is controlled through the resistance control circuit 696 to cut off the electric power supplied to the second SMA wire 660, whereas the first and third voltage control circuits 664, 668 are controlled such that a voltage is applied with the same value from the power source circuit 694 to the first and third SMA wires 658, 662. The first and third SMA wires 658, 662 are thereby heated for contraction of their length. As a result, the first and third angle wires 614, 618 are pulled evenly so as to bend the bendable portion 602 in the leftward direction.

When bending the bendable portion 602 in the direction midway between up and right, i.e., in the UR direction, the third voltage control circuit 668 is controlled through the resistance control circuit 696 to cut off the electric power supplied to the third SMA wire 658, whereas the first and second voltage control circuits 664, 666 are controlled such that voltages of different values from each other are applied from the power source circuit 694 to the first and second SMA wires 658, 660. At this time, as shown in FIG. 51, the voltage of a larger value is applied to the first SMA wire 658 and the voltage of a smaller value is applied to the second SMA wire 660. As a result, the first SMA wire 658 is contracted to a large extent and the second SMA wire 660 is contracted to a small extent. The resultant tensile force produced by the first and second SMA wires 658, 660 causes the bendable portion 602 in the UR direction.

It will be seen from FIG. 51 that when bending the bendable portion 602 in the direction midway between up and left, i.e., in the UL direction, this can be effected by controlling the second and third SMA wires 660 and 662 in an exchanged manner with respect to those in the above control of bending the bendable portion 602 in the UR direction. Additionally, when bending the bendable portion 602 in the direction midway between down and right, i.e., in the DR direction, or in the direction midway between down and left, i.e., in the DL direction, these can be effected by controlling respective voltages applied to the first to third SMA wires 658–662 as shown in a time chart of FIG. 51.

While the above explanation has been made with reference to the bending operations in the typical directions, the bendable portion 602 can be bent by changing a ratio of the voltage values applied to the first to third SMA wires 658–662. Further, by changing the amount of electric power supplied to each SMA wire (e.g., the voltage value, pulse width or duty ratio) while keeping the above ratio constant, the bending amount (i.e., the bending angle) can be changed as desired.

Figure 57:
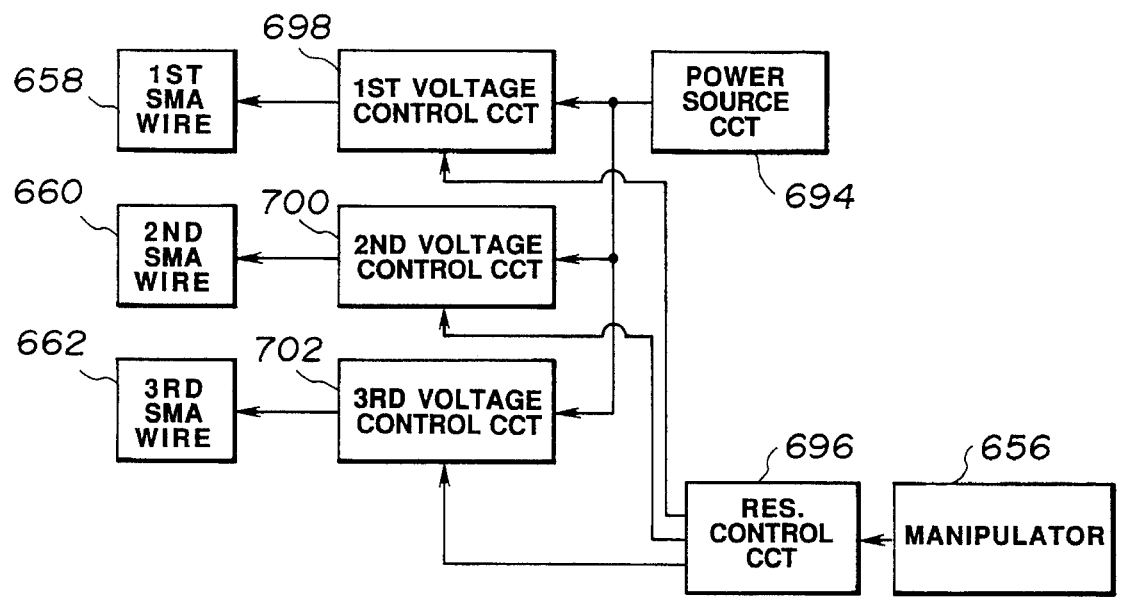

As a modification of the driver used in this embodiment, a driver as shown in FIG. 57 can also be employed. More specifically, in this modification, there are provided first to third PWM control circuits 698, 700, 702 in place of first to third voltage control circuits 664, 666, 668. The driver of this modification controls the amounts of electric power supplied to the first to third SMA wires 658, 660, 662 for heating through the pulse width modulation (PWM) technique.

It is needless to say that the present invention is not limited to the aforementioned embodiment and can also be applied to, for example, the case of bending a catheter, appliance or the like other than an endoscope.

Figure 58:
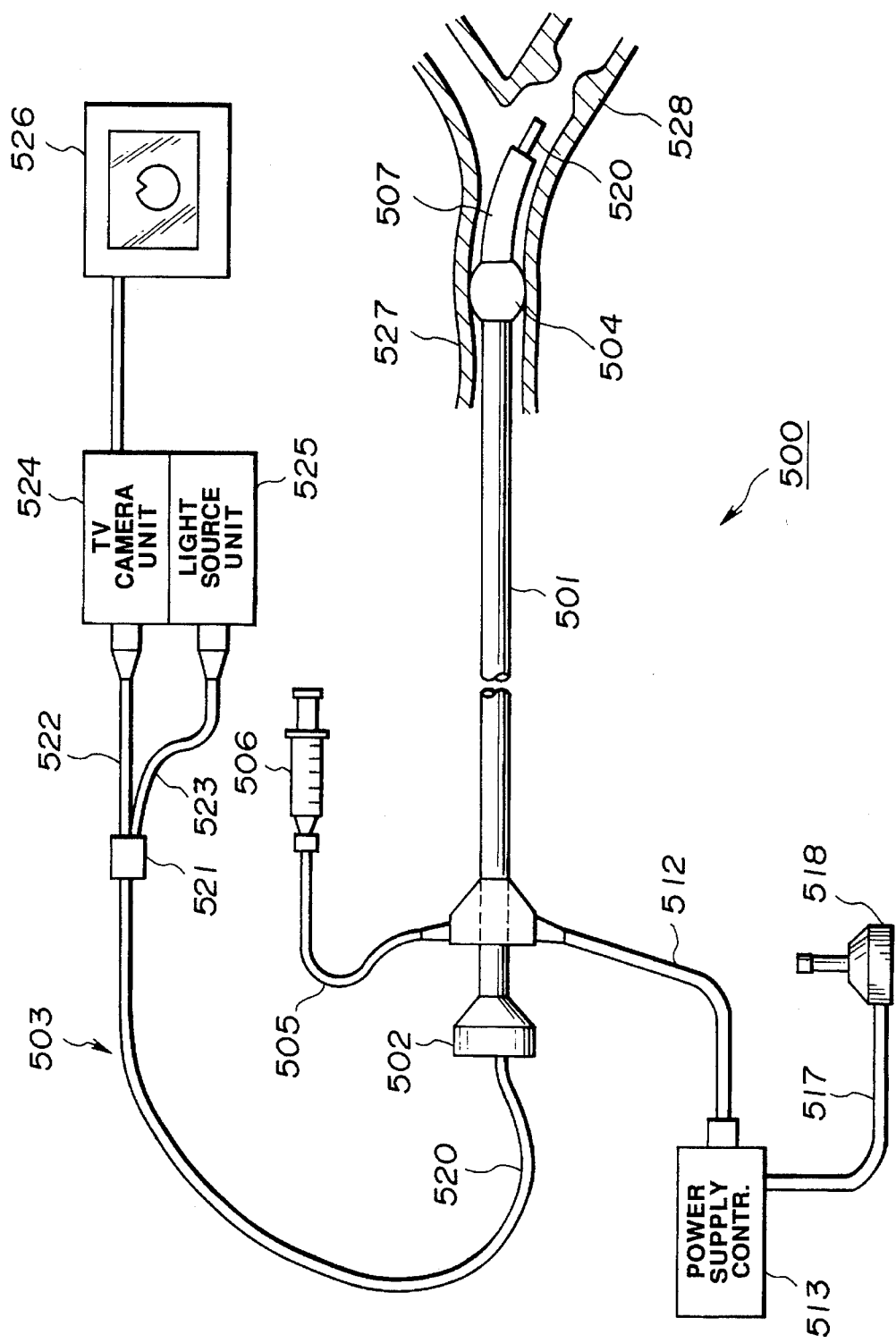

An intravascular endoscope device for inspecting the interior of blood vessels will be described below. FIG. 58 shows an intravascular endoscope device 500 according to a thirteenth embodiment of the present invention, which device comprises a tube-like catheter 501 to be inserted to a blood vessel 527, and an endoscope 503 to be inserted to the catheter 501 through an insertion guide 502 provided at the rear end of the catheter 501.

The catheter 501 is formed of, by way of example, a multi-lumen tube having flexibility and a balloon 504 is fitted over the distal end portion of the catheter 501. The balloon 504 serves to expand the blood vessel 527, and a fluid such as a physiological saline solution can be supplied from a syringe 506 which is connected to the rear end portion of the catheter 501 via a tube 505.

Figure 59:
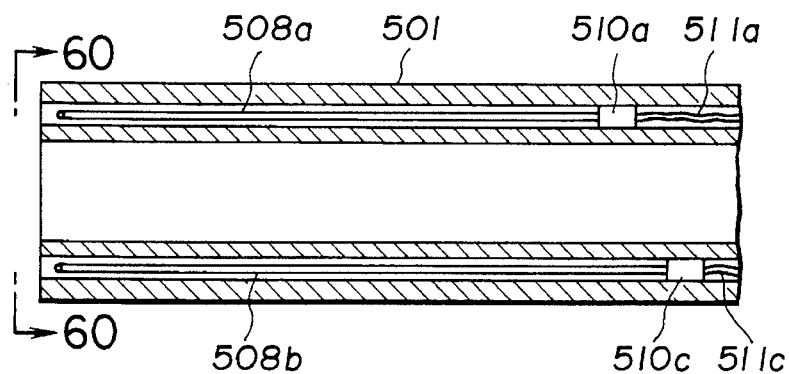

The catheter 501 includes a bendable portion 507 provided in the distal end side forwardly of the balloon 504 and, as shown in FIG. 59, bending actuator wires 508a, 508b are inserted through the bendable portion 7 to extend in the axial direction of the catheter 501. These bending actuator wires 508a, 508b are each formed of a two-directional shape memory alloy, by way of example, and can be contracted in the axial direction when heated to predetermined temperatures (e.g., from 60° to 90° C.).

Figure 60:
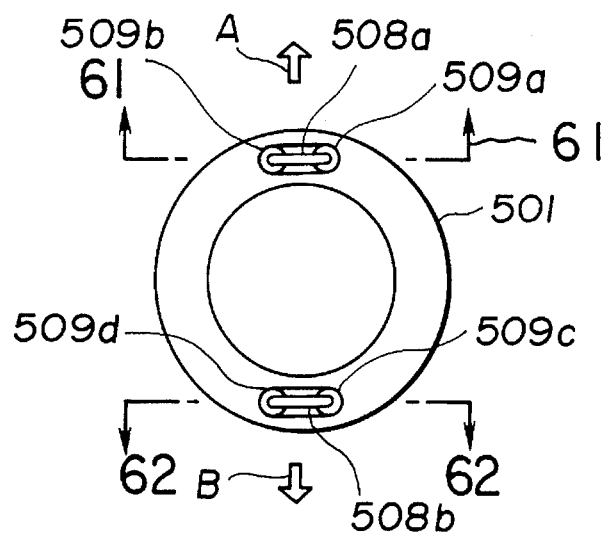

As shown in FIG. 60, the bending actuator wires 508a, 508b are disposed at positions angularly spaced by 180° from each other in the circumferential direction of the catheter 501. Accordingly, when the bending actuator wire 508a is contracted, the distal end portion of the catheter 501 is bent in the direction of arrow A, and when the bending actuator wire 508b is contracted, the distal end portion of the catheter 501 is bent in the direction of arrow B. The bending actuator wires 508a, 508b are bent at their distal ends into a U-shape for turn-back, as shown in FIGS. 61 and 62, and extended through wire insertion holes 509a, 509b, 509c, and 509d bored inside the catheter 501, respectively.

Further, the respective ends of the bending actuator wires 508a, 508b are connected to lead wires 511a, 511b, 511c, 511d via caulking members 510a, 510b, 510c, and 510d. Those lead wires 511a, 511b, 511c, 511d are connected to a power supply controller 513 (see FIG. 58) in turn connected to the rear end portion of the catheter 501 via a cable 512. The power supply controller 513 supplies the electric power to the bending actuator wires 508a, 508b for heating.

Figure 63:
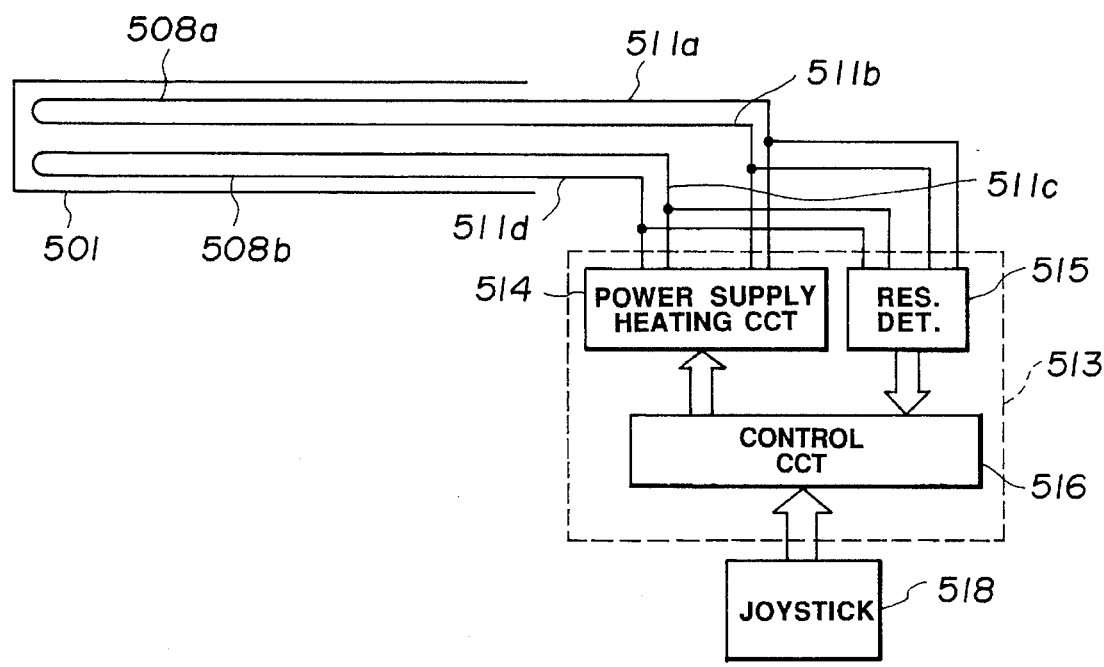

The power supply controller 513 comprises, as shown in FIG. 63, a power supply and heating circuit 514 for supplying the electric power to the bending actuator wires 508a, 508b via the lead wires 511a, 511b, 511c, 511d to heat the wires, a resistance value detector 515 for detecting respective resistance values of the bending actuator wires 508a, 508b, and a control circuit 516 for controlling output currents of the power supply and heating circuit 514 in accordance with the respective resistance values of the bending actuator wires 508a, 508b detected by the resistance value detector 515. A joystick 518 is connected to the power supply controller 513 via a cable 517 and produces an output to bend the bendable portion 507 when manually operated.

Figure 61:
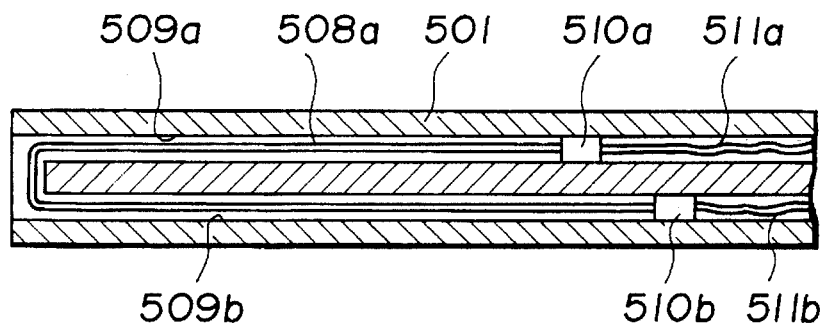
Figure 62:
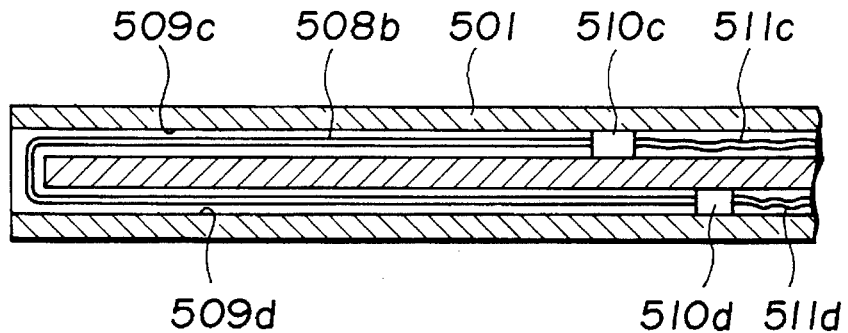
Figure 64:
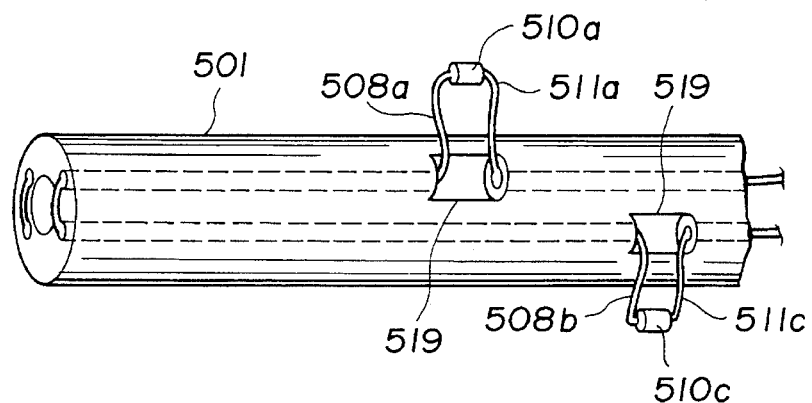

As shown in FIGS. 59, 61 and 62, the caulking members 510a, 510b, 510c, 510d provided at the respective ends of the bending actuator wires 508a, 508b are arranged at positions shifted from one another in the axial direction of the catheter 501 to be out of overlapping therebetween. Further, the caulking members 510a, 510b, 510c, 510d are fixed to the catheter 501 by using resin or the like to serve as stationary portions of the bending actuator wires 508a, 508b. The bending actuator wires 508a, 508b and the lead wires 511a, 511b, 511c, 511d are interconnected as follows, by way of example. As shown in FIG. 64, side holes 519 are bored in the outer circumferential wall of the catheter 501, and the respective ends of the bending actuator wires 508a, 508b and the lead wires 511a, 511b, 511c, 511d are fixed in places by the caulking members 510a, 510b, 510c, 510d through caulking made at locations corresponding to the side holes 519. After that, by pulling the lead wires 511a, 511b, 511c, 511d toward the proximal end side of the catheter, the caulking members 510a, 510b, 510c, 510d are accommodated in the respective side holes 519, followed which the side holes 519 are filled with resin or the like.

On the other hand, the endoscope 503 comprises an endoscope insert 520 in the form of a thin tube having flexibility, and an endoscope body 521 provided at the rear end of the endoscope insert 520. Connected to the endoscope body 521 are TV camera unit 524 and a light source unit 525 via respective universal cords 522, 523. A TV monitor 526 is connected to the TV camera unit 524 so that the operator can observe the interior of the blood vessel 527 on the screen of the TV monitor 526.

When the intravascular endoscope device 500 thus constructed is used to make a diagnosis of a thrombus area 528 in the blood vessel 527, for example, the catheter 501 is first inserted to the blood vessel 527 and the balloon 504 is then so expanded as to fix the catheter 501 in the blood vessel 527. Thereafter, the endoscope 503 is inserted to the catheter 501 through the insertion guide 502 provided at the rear end of the catheter 501 to such an extent that the distal end portion of the endoscope 503 is projected from the distal end of the catheter 501. By manually operating the joystick 518 under that condition, the power supply controller 513 supplies the electric power to the bending actuator wire 508a for heating, by way of example, whereupon the bending actuator wire 508a is contracted in the axial direction to bend the distal end portion of the catheter 501 (i.e., the bendable portion 507) in a predetermined direction, as set forth before. Consequently, the distal end of the endoscope 503 can be directed toward the location to be diagnosed.

In the intravascular endoscope device 500 thus constructed, since the stationary portions of the bending actuator wires 508a, 508b (i.e., the caulking members 510a, 510b, 510c, 510d) are arranged at positions shifted from one another in the axial direction of the catheter 501, the stationary portions of the bending actuator wires 508a, 508b are kept from overlapping therebetween in the same cross-sectional plane radially of the catheter 501. This enables to prevent the catheter 501 from increasing in its diameter.

Figure 65:
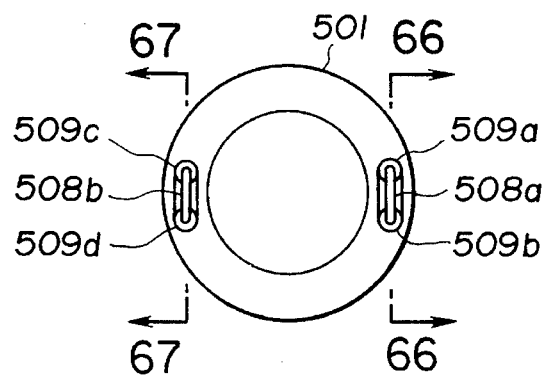
Figure 66:
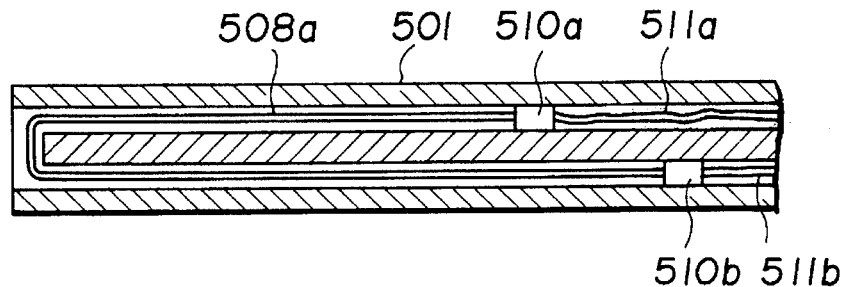
Figure 67:
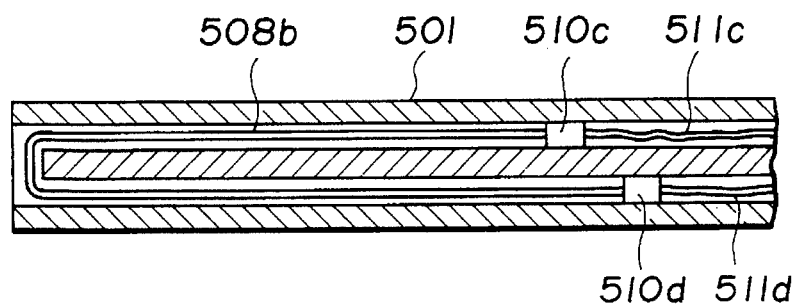

In the above embodiment, the lengths of the bending actuator wires 508a, 508b are made different to shift the positions of their stationary portions (i.e., the caulking members 510a, 510b, 510c, 510d) from one another in the axial direction of the catheter 501. However, the bending actuator wires 508a, 508b can also have the same length with such an arrangement that, as shown in FIGS. 65 to 67, the caulking members 510a, 510b for interconnecting the bending actuator wire 508a and the lead wires 511a, 511b are positioned to have a large spacing therebetween, whereas the caulking members 510c, 510d for interconnecting the bending actuator wire 508b and the lead wires 511c, 511d are positioned to lie between the caulking members 510a and 510b. This arrangement enables the bendable portion 507 to bend by the same angle in both the directions of arrows A, B with the same amount of electric power supplied.

Figure 68:
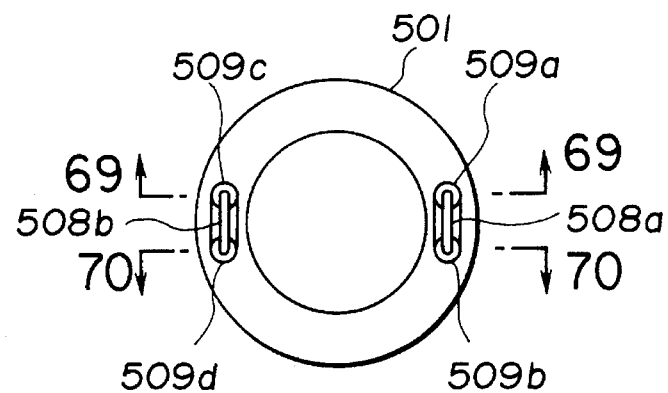
Figure 69:
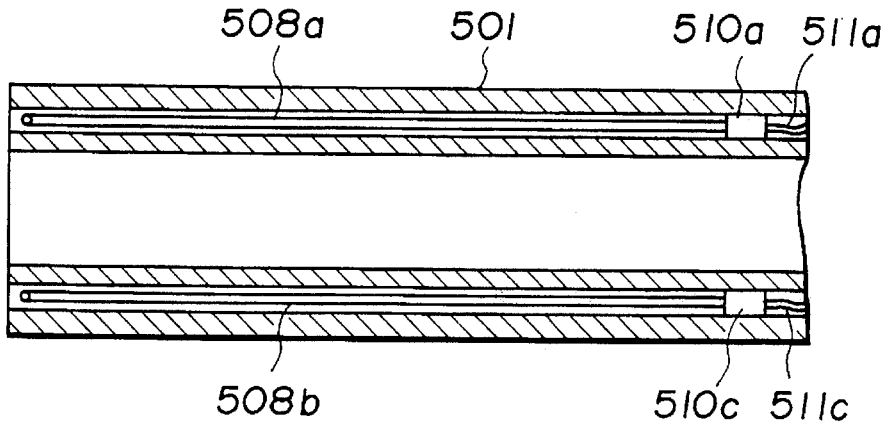
Figure 70:
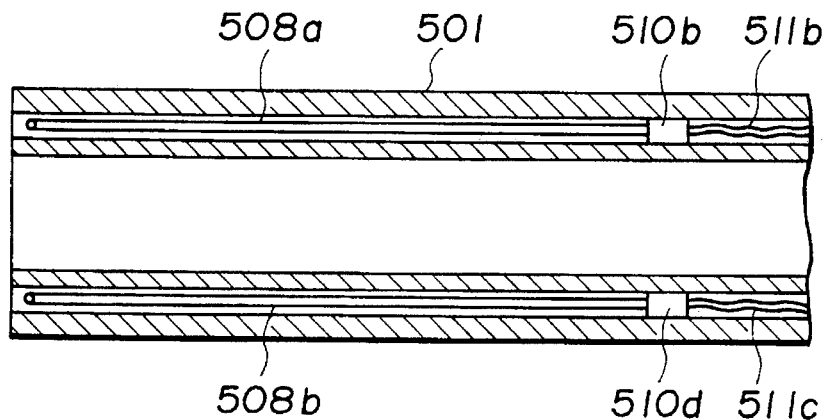

Alternatively, by arranging the caulking members 510a, 510c provided at one end of the bending actuator wires 508a, 508b in the same axial position along the catheter 501 and also arranging the caulking members 510b, 510d provided at the other end of the bending actuator wires 508a, 508b in the same axial position along the catheter 501 as shown in FIGS. 68 to 70, the length necessary for the stationary portions of the bending actuator wires can be shortened, although the outer diameter of the catheter 501 is somewhat increased. Thus, this arrangement enables to cut down the length of the hard portion of the catheter.

Figure 71:
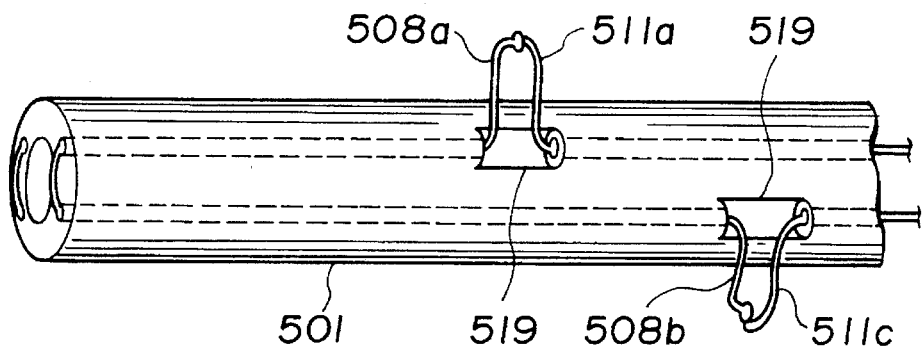
FIG. 71 is a perspective view showing the distal end of a catheter according to a sixteenth embodiment of the present invention.

Additionally, while the bending actuator wires 508a, 508b and the lead wires 511a, 511b, 511c, 511d are interconnected by means of the caulking members 510a, 510b, 510c, 510d in the above embodiment, it is also possible to interconnect the bending actuator wires 508a, 508b and the lead wires 511a, 511b, 511c, 511d by welding, as shown in FIG. 71.

Seventeenth to nineteenth embodiments of the present invention will be described below with reference to FIGS. 72 to 74.

Figure 72:
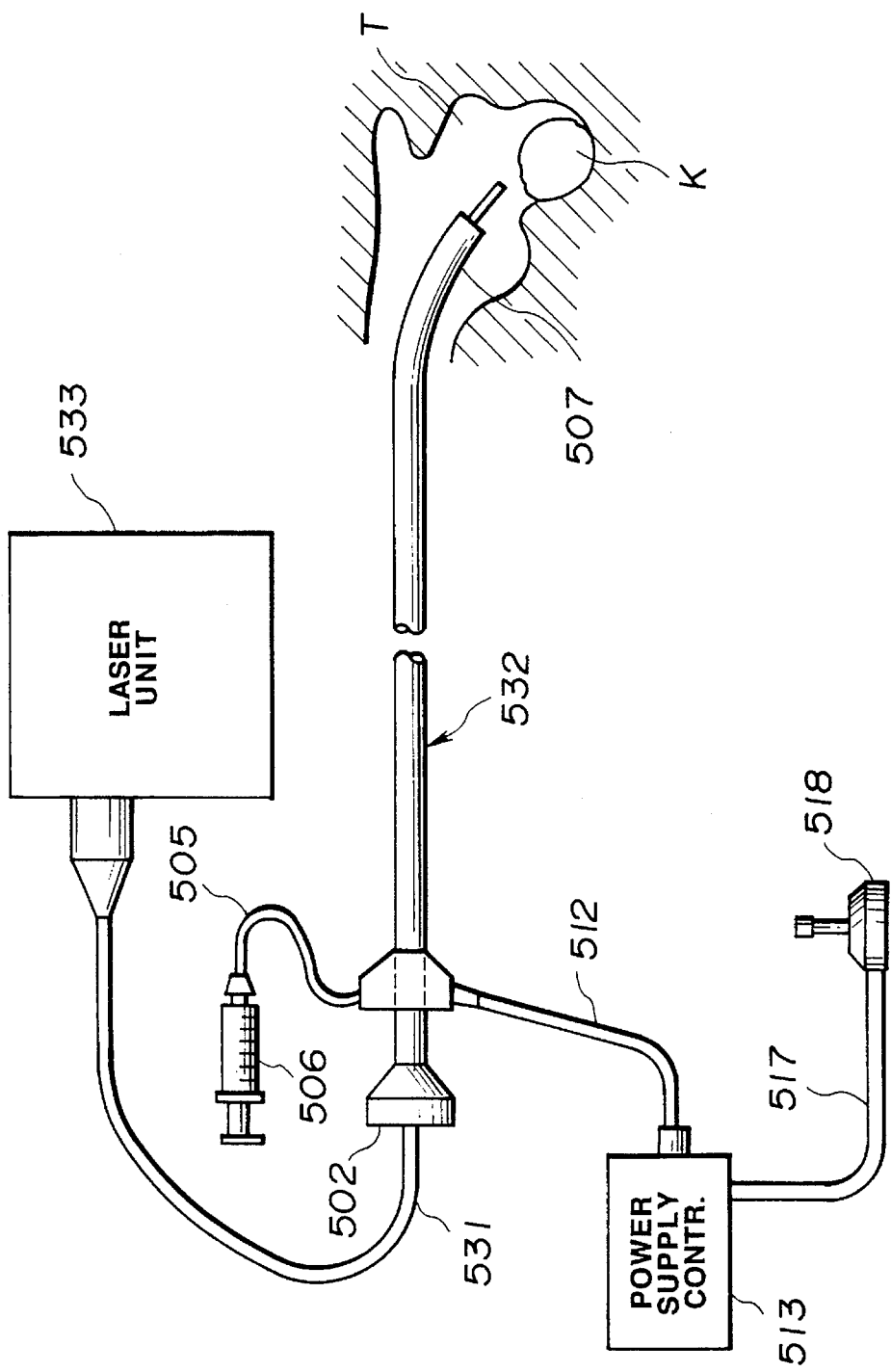
FIG. 72 is a diagram showing the configuration of a laser probe according to a seventeenth embodiment of the present invention.

FIG. 72 shows an embodiment in which the present invention is applied to a catheter 532 for a laser probe 531 adapted to crush a calculus K or in a body cavity T. This catheter 532 is the same as the catheter 501 shown in FIG. 58 except that the balloon 504 provided around the distal end portion of the latter catheter 501 is removed away. The laser probe 531 can be inserted to the catheter 532 through the insertion guide 502 provided at the rear end of the catheter 532, and a laser unit 533 as a laser beam source is connected to the rear end of the laser probe 531.

Figure 73:
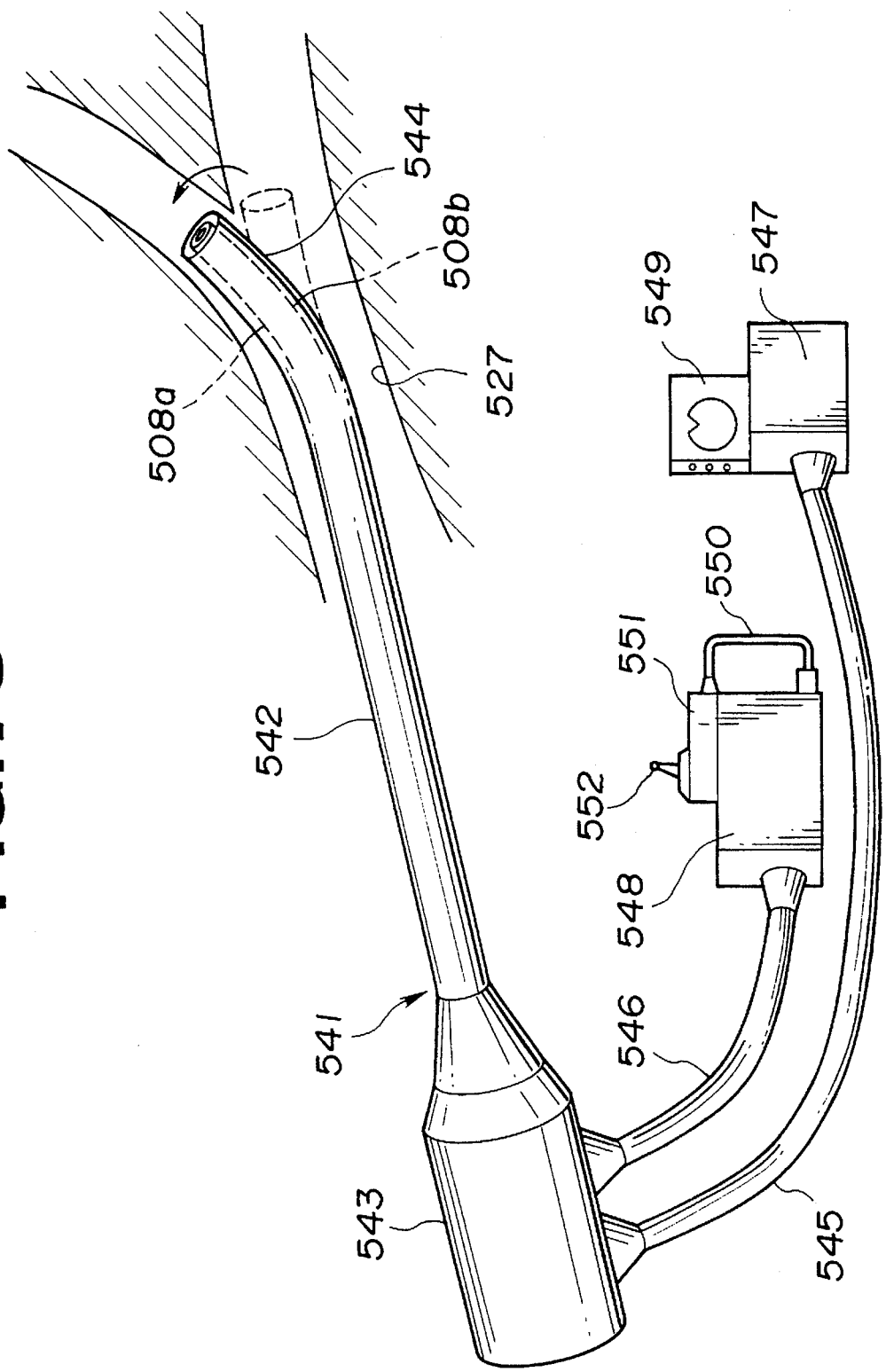
FIG. 73 is a diagram showing the configuration of an endoscope for blood vessels according to an eighteenth embodiment of the present invention.

FIG. 73 shows an embodiment in which the present invention is applied to an intravascular endoscope 541. More specifically, this intravascular endoscope 541 comprises an insert 542 to be inserted to the blood vessel 527, and an operating section 543 provided at the rear end of the insert 542. A bendable portion 544 having the same arrangement as the bendable portion 507 shown in FIGS. 58 to 63 is provided in the distal end portion of the insert 542. Further, a TV camera unit 547 and a light source unit 548 are connected to the operating section 543 via respective universal cords 545, 546 and a TV monitor 549 is connected to the TV camera unit 547. In addition, a power supply controller 551 is connected to the light source unit 548 via a cable 550. A joystick 552 as a manipulator is connected to the power supply controller 551 and produces an output to bend the bendable portion 544 when manually operated.

FIG. 74 shows an embodiment in which the present invention is applied to a laser probe 561. More specifically, this laser probe 561 comprises an insert 562 in the form of a thin tube having flexibility, and a probe body 563 provided at the rear end of the insert 562. A bendable portion 564 having the same arrangement as the bendable portion 507 shown in FIGS. 58 to 63 is provided in the distal end portion of the insert 562. Connected to the probe body 563 are a laser unit 564 and also a power supply controller 566 via a cable 565. Further, a joystick 567 as a manipulator is connected to the power supply controller 566 and produces an output to bend the bendable portion 564 when manually operated.

With the thirteenth to nineteenth embodiment as set forth above, each probe device comprises a flexible probe insert body to be inserted to tracts or cavities, a plurality of bending actuator members each formed of a shape memory alloy buried in the distal end portion of the probe insert body to extend in the axial direction thereof, and stationary portions provided at least one end of the bending actuator members and fixed to the probe insert body in such a manner that their positions are shifted from one another axially of the probe insert body to be out of overlapping therebetween. Accordingly, the stationary portions of the bending actuator members are kept from overlapping with one another in the axial direction of the probe insert body, making it possible to reduce an outer diameter of the probe insert body.

It should be understood that parts of the foregoing embodiments can be combined together to constitute other different embodiments which also fall in the scope of the present invention.

What is claimed is:

1. A bending tube for use with an endoscope comprising:

an elongate tube having flexibility including a plurality of ring-like bending pieces extending in the lengthwise direction of said tube, wherein every two adjacent pieces are pivotally coupled to each other in a rotatable manner;

a non-compressive member arranged to extend in the lengthwise direction of said tube, having a distal end thereof fixed to said tube with a predetermined space from a tip of said tube and the proximal end thereof as a free end in the lengthwise direction of said tube, and not being contractile in the lengthwise direction of said tube;

an operating member having a shape memory member arranged to extend in the lengthwise direction of said tube, having one end thereof attached to near the distal end of said tube and the other end thereof attached to said proximal end of said non-compressive member, and having a length variable in the longitudinal direction upon heating at least a part thereof; and an electric cable electrically connected with at least said shape memory member to transmit a drive signal for heating said shape memory member.

2. A bending actuator for use with an endoscope, comprising:

an elongate tube having flexibility;

a bending member arranged in the distal end portion of said tube to extend in the lengthwise direction of said tube and holding said distal end portion in a bendable manner wherein said bending member comprises a plurality of ring-like bending pieces accommodated in said tube to extend in the lengthwise direction of said tube, wherein every two adjacent pieces are pivotally coupled to each other in a rotatable manner;

a bending drive member attached to near the distal end of said bending member with at least one end of said bending drive member being restricted in its position, for bending said bending member;

a shape memory member constituting at least a portion of said bending drive member and formed by bundling together a plurality of wire-like shape memory materials having shape-memory characteristics including substantially the same contractile characteristic at an equal transformation temperature each having a length that spans from the position of one end to the other end thereof, and which is reversibly changed upon heating and cooling;

an electric cable electrically connected with said shape memory member to transmit a drive signal for heating said shape memory member; and a non-compressive member having a tubular structure through which a fluid for cooling said shape memory member is to be passed, said non-compressive member arranged to extend in a lengthwise direction of said tube for accommodating at least part of said bending drive member, said non-compressive member having the distal end thereof fixed to said tube and the proximal end thereof as a free end in the lengthwise direction of said tube, said proximal end being coupled to a proximal end of said shape memory member, and not being contractile in the lengthwise direction of said tube.

3. A bending actuator according to claim 2, wherein the proximal end side of said non-compressive member includes a valve and is connected to fluid supply means for supplying said fluid.

4. A bending actuator comprising:

a flexible elongated tube;

a bendable bending member connected to a distal end portion of said tube through a joint ring;

a coil sheath having a distal end joined to an inner peripheral surface of said joint ring, said coil sheath arranged in said tube in a lengthwise direction and having a proximal end that is free and independent of said elongated tube;

a plug arranged at another end of said coil sheath;

an operation wire having one end connected to a distal end side of said bending member and having another end extended within said coil sheath;

a shape memory member arranged in said coil sheath, one end of said shape memory member joined to another end of said operation wire and another end connected to said plug, said shape memory member being able to be contractile and transformed in a lengthwise direction; and an electric cable electrically connected to said shape memory member through said plug.

5. The bending actuator according to claim 4, further comprising an insulating tube arranged on an inner peripheral surface of said coil sheath.

6. The bending actuator according to claim 4, further comprising a guide tube whose end is joined to said plug, for guiding said electric cable.

7. The bending actuator according to claim 6, wherein said plug has a channel joining said coil sheath to said guide tube, and said guide tube is a tube for supplying air and supplies air into said coil sheath in the channel of said plug to cool said shape memory member.

8. The bending actuator according to claim 4, wherein said plug is formed of insulating members and has a core member electrically connecting said shape memory member and said electric cable in an inner part of said plug.

9. The bending actuator according to claim 4, wherein said operation wire and said shape memory member are connected through a wire joined member, and said wire joined member is formed of electric conductors and includes insulating material insulating a part between said operation wire and said shape memory member.

10. The bending actuator according to claim 9, wherein said wire joined member forms an electrode electrically connecting said one end of said shape memory member.

11. The bending actuator according to claim 10, wherein said plug includes a channel joining said coil sheath, an electric wire is arranged in said coil sheath through said channel, and one end of said electric wire is electrically connected to said electrode of said wire joined member.

12. The bending actuator according to claim 4, wherein said operation wire consists of a plurality of wire strands and said shape memory member is connected to each of said wire strands to be bendable in any direction.

13. The bending actuator according to claim 12, including a plurality of said shape memory members, each said shape memory member having substantially the same elastic characteristic amount.

14. The bending actuator according to claim 4, wherein said coil sheath is constructed of a non-contractible material.

15. The bending actuator according to claim 4, wherein said shape memory member is formed to be a wire member by binding a plurality of wire shape memory materials each having a length from one end to another end which reversibly changes by heating/cooling said shape memory member.

* * * * *